(12) United States Patent
Nusbaum et al.

(10) Patent No.: US 10,134,302 B2
(45) Date of Patent: Nov. 20, 2018

(54) MOBILE COMPUTING WEIGHT, DIET, NUTRITION, AND EXERCISE MANAGEMENT SYSTEM WITH ENHANCED FEEDBACK AND GOAL ACHIEVING FUNCTIONALITY

(71) Applicant: SmarTEN LLC, McLean, VA (US)

(72) Inventors: Mark E. Nusbaum, McLean, VA (US); Vincent Pera, Jr., Cranston, RI (US); Jan E. Rhoads, Grapevine, TX (US); Jennifer L. Nusbaum, Herndon, VA (US)

(73) Assignee: SmarTEN LLC, McLean, VA (US)

( * ) Notice: Subject to any disclaimer, the term of this patent is extended or adjusted under 35 U.S.C. 154(b) by 0 days.

(21) Appl. No.: 15/650,951

(22) Filed: Jul. 16, 2017

(65) Prior Publication Data
US 2017/0323582 A1    Nov. 9, 2017

Related U.S. Application Data

(63) Continuation of application No. 15/361,383, filed on Nov. 26, 2016, now Pat. No. 9,728,102, which is a (Continued)

(51) Int. Cl.
*A61B 5/00* (2006.01)
*G09B 19/00* (2006.01)
(Continued)

(52) U.S. Cl.
CPC ...... *G09B 19/0092* (2013.01); *A63B 24/0062* (2013.01); *G06F 19/00* (2013.01);
(Continued)

(58) Field of Classification Search
CPC ............ G09B 19/0092; A63B 24/0062; G06F 19/3475
See application file for complete search history.

(56) References Cited

U.S. PATENT DOCUMENTS 7,809,565 B2    10/2010   Coifman
8,690,578 B1     4/2014   Nusbaum et al.
(Continued)

OTHER PUBLICATIONS

Byford, Sam, The Verge—Samsung S Health Launched: Control Your Weight and Blood Sugar with the Galaxy S III, http://www.theverge.com/2012/7/2/3131468/samsung-s-health-weight-blood-sugar-galaxy-s-iii, Jul. 2, 2012, 4 pp.
(Continued)

*Primary Examiner* — John R Downey

(57) ABSTRACT

An illustrative mobile computing device executing weight, nutrition, health, behavior and exercise application software serves as a simulated combination personal trainer and dietician/nutritionist for the user using comprehensive databases storing personalized health, nutrition and exercise information. A mobile computing device, such as a smartphone, executing such software monitors, tracks and/or adjusts caloric intake, energy expenditure taking into account nutritional information and behavioral factors. The mobile computing device receives food consumption, exercise-related, behavior and other input using speech input and the device's GPS subsystem to ease data entry burden on users and to promote continued long-term usage. The system rewards user goal achievement in an automatic, seamless manner, through, for example, downloading music, books, or other media. In illustrative implementations, the system assists users to make healthy food and exercise choices by using a comprehensive color code system to identify good choices, bad choices and those in between.

19 Claims, 41 Drawing Sheets

Related U.S. Application Data continuation of application No. 15/175,296, filed on Jun. 7, 2016, now Pat. No. 9,514,655, which is a continuation of application No. 15/047,817, filed on Feb. 19, 2016, now Pat. No. 9,378,657, which is a continuation of application No. 14/242,106, filed on Apr. 1, 2014, now Pat. No. 9,280,640, which is a continuation of application No. 13/733,588, filed on Jan. 3, 2013, now Pat. No. 8,690,578.

(51) Int. Cl.
  *G06F 19/00*   (2018.01)
  *A63B 24/00*   (2006.01)
  *G09B 5/12*    (2006.01)

(52) U.S. Cl.
  CPC ...... *G06F 19/3475* (2013.01); *G06F 19/3481* (2013.01); *G09B 5/125* (2013.01); *G09B 19/00* (2013.01); *A63B 2024/0071* (2013.01); *A63B 2220/12* (2013.01); *A63B 2220/17* (2013.01); *A63B 2220/20* (2013.01); *A63B 2220/807* (2013.01); *A63B 2225/50* (2013.01); *A63B 2230/04* (2013.01); *A63B 2230/75* (2013.01)

(56) References Cited

U.S. PATENT DOCUMENTS

| | | | |
|---|---|---|---|
| 9,280,640 B2 | 3/2016 | Nusbaum et al. | |
| 9,378,657 B1 | 6/2016 | Nusbaum et al. | |
| 9,514,655 B1 | 12/2016 | Nusbaum et al. | |
| 2004/0162702 A1* | 8/2004 | Pandipati | G01G 19/4146 702/173 |
| 2005/0021361 A1* | 1/2005 | Huang | G01G 19/4146 705/2 |
| 2005/0054381 A1 | 3/2005 | Lee et al. | |
| 2005/0113650 A1* | 5/2005 | Pacione | A61B 5/411 600/300 |
| 2005/0118996 A1 | 6/2005 | Lee et al. | |
| 2005/0143138 A1 | 6/2005 | Lee et al. | |
| 2006/0064037 A1* | 3/2006 | Shalon | A61B 5/0006 600/586 |
| 2006/0064447 A1* | 3/2006 | Malkov | G06F 15/16 708/200 |
| 2006/0106744 A1 | 5/2006 | Kim et al. | |
| 2006/0129432 A1 | 6/2006 | Choi et al. | |
| 2006/0168137 A1 | 7/2006 | Lim et al. | |
| 2006/0235280 A1* | 10/2006 | Vonk | G06F 19/3481 600/300 |
| 2007/0173703 A1* | 7/2007 | Lee | G01G 19/4146 600/300 |
| 2007/0173726 A1 | 7/2007 | Kim et al. | |
| 2007/0179356 A1* | 8/2007 | Wessel | A61B 5/14532 600/300 |
| 2007/0191689 A1* | 8/2007 | Elitok | G06F 19/3475 600/300 |
| 2007/0276591 A1 | 11/2007 | Lea et al. | |
| 2008/0096726 A1* | 4/2008 | Riley | A63B 24/0006 482/8 |
| 2009/0076903 A1* | 3/2009 | Schwarzberg | G06F 19/3475 705/14.19 |
| 2009/0118100 A1* | 5/2009 | Oliver | A63B 24/0062 482/8 |
| 2009/0182240 A1 | 7/2009 | Jang et al. | |
| 2009/0240113 A1* | 9/2009 | Heckerman | A61B 5/0002 600/300 |
| 2009/0326981 A1* | 12/2009 | Karkanias | G06Q 10/10 705/3 |
| 2010/0003647 A1* | 1/2010 | Brown | G09B 19/0092 434/127 |
| 2010/0042438 A1* | 2/2010 | Moore | G06F 19/18 705/3 |
| 2010/0049471 A1* | 2/2010 | Gage | G06F 19/00 702/173 |
| 2010/0088118 A1 | 4/2010 | Jang et al. | |
| 2010/0121156 A1 | 5/2010 | Yoo | |
| 2010/0173269 A1* | 7/2010 | Puri | G09B 19/0092 434/127 |
| 2011/0047108 A1* | 2/2011 | Chakrabarty | G06F 19/3456 706/14 |
| 2011/0054269 A1 | 3/2011 | Lee et al. | |
| 2011/0066451 A1 | 3/2011 | Jang et al. | |
| 2011/0071365 A1 | 3/2011 | Lee et al. | |
| 2011/0159469 A1 | 6/2011 | Hwang et al. | |
| 2011/0160550 A1 | 6/2011 | Hwang et al. | |
| 2011/0184247 A1* | 7/2011 | Contant | G06Q 10/10 600/300 |
| 2011/0184754 A1 | 7/2011 | Park et al. | |
| 2011/0201242 A1 | 8/2011 | Hur et al. | |
| 2011/0218407 A1* | 9/2011 | Haberman | G06F 19/3475 600/300 |
| 2012/0059664 A1* | 3/2012 | Georgiev | A61B 5/02 705/2 |
| 2012/0136218 A1 | 5/2012 | Lee et al. | |
| 2012/0141964 A1 | 6/2012 | Lee | |
| 2012/0143014 A1 | 6/2012 | Kim et al. | |
| 2012/0143621 A1 | 6/2012 | Lee et al. | |
| 2012/0189177 A1 | 7/2012 | Oh | |
| 2012/0221495 A1* | 8/2012 | Landers | G06F 19/3475 706/12 |
| 2012/0278072 A1 | 11/2012 | Park et al. | |
| 2012/0323590 A1* | 12/2012 | Udani | G06Q 10/103 705/2 |
| 2012/0329021 A1* | 12/2012 | Hughes | G09B 19/003 434/257 |
| 2013/0218585 A1* | 8/2013 | Watterson | G06F 19/3481 705/2 |
| 2013/0268292 A1 | 10/2013 | Kim et al. | |
| 2013/0300546 A1 | 11/2013 | Kim et al. | |
| 2014/0145860 A1 | 5/2014 | Park et al. | |
| 2014/0149920 A1 | 5/2014 | Wang et al. | |
| 2014/0173082 A1 | 6/2014 | Shin | |
| 2014/0236262 A1 | 8/2014 | You et al. | |

OTHER PUBLICATIONS

"Calories Burned Exercising," 2011, LiveStrong.com article with expanded Breakouts, 20 pages.
David Zinczenko, Eat This Not That, Restaurant Survival Guide, 2010, entire 312 page book provided.
David Zinczenko, "Eat This Not That, Supermarket Survival Guide," 2012 Edition, published Nov. 2011, entire 348 page book provided.
David Zinczenko, "Eat This Not That," Updated 2012 Edition, published Aug. 2011, entire 326 page book provided.
David Zinczenko, "The Eat This Not That Diet," 2011, entire 330 page book provided.
"Diet and Weight Loss Tutorial," excerpted from LiveStrong.com Diet and Weight Loss Tutorial, 25 pages, published in 2011 or 2012.
"How to pick useful health apps for mobile devices," Washington Post, Jul. 12, 2004, p. E4, accessed from Washington Post web site.
Jennifer Cohen, "The 8 Best Smart Phone Apps for Weight Loss," Aug. 21, 2012, Forbes, pp. 1-5 accessed from Forbes web site.
Jim Duffy, "The Best Apps for Losing Weight," Jan. 13, 2012, PC Magazine, pp. 1-7 accessed from PC Magazine web site.
Kashifraza, Top 3 Weight loss and Fitness Apps for iPhone and iPad, Mar. 18, 2012, TechWench, pp. 1-6 accessed from TechWench web site.
Kim Painter, "Health-tracking apps are largely standing still," Jan. 28, 2013, USA Today, 2D Life.
MyFitnessPal.com Web Site (About, Food, Exercise, Apps, Blog) printout, 17 pages printed on Sep. 8, 2013, Copyright, 2005-2013 MyFitnessPal, LLC.
Samsung Galaxy S® 4 4 G LTE Smartphone User Manual, Samsung Telecommunications America, LLC, Applications, pp. 184-186, 2013, 5 pp. total.
S Health Integration Demo with the Samsung Galaxy S 4 | PhoneArena Reviews, http://www.phonearena.com/news/S-Health-integration-demo-with-the-Samsung-Galaxy-S-4_id40886, posted Mar. 15, 2013, 4 pp.

(56) References Cited

OTHER PUBLICATIONS

Tracy Rosecrans, "10 Best Weight Loss iPhone & Android Apps 2012," Healthline Topics & Tools, published Sep. 8, 2012, accessed from healthline web site showing 13 slides depicting 10 apps.

* cited by examiner

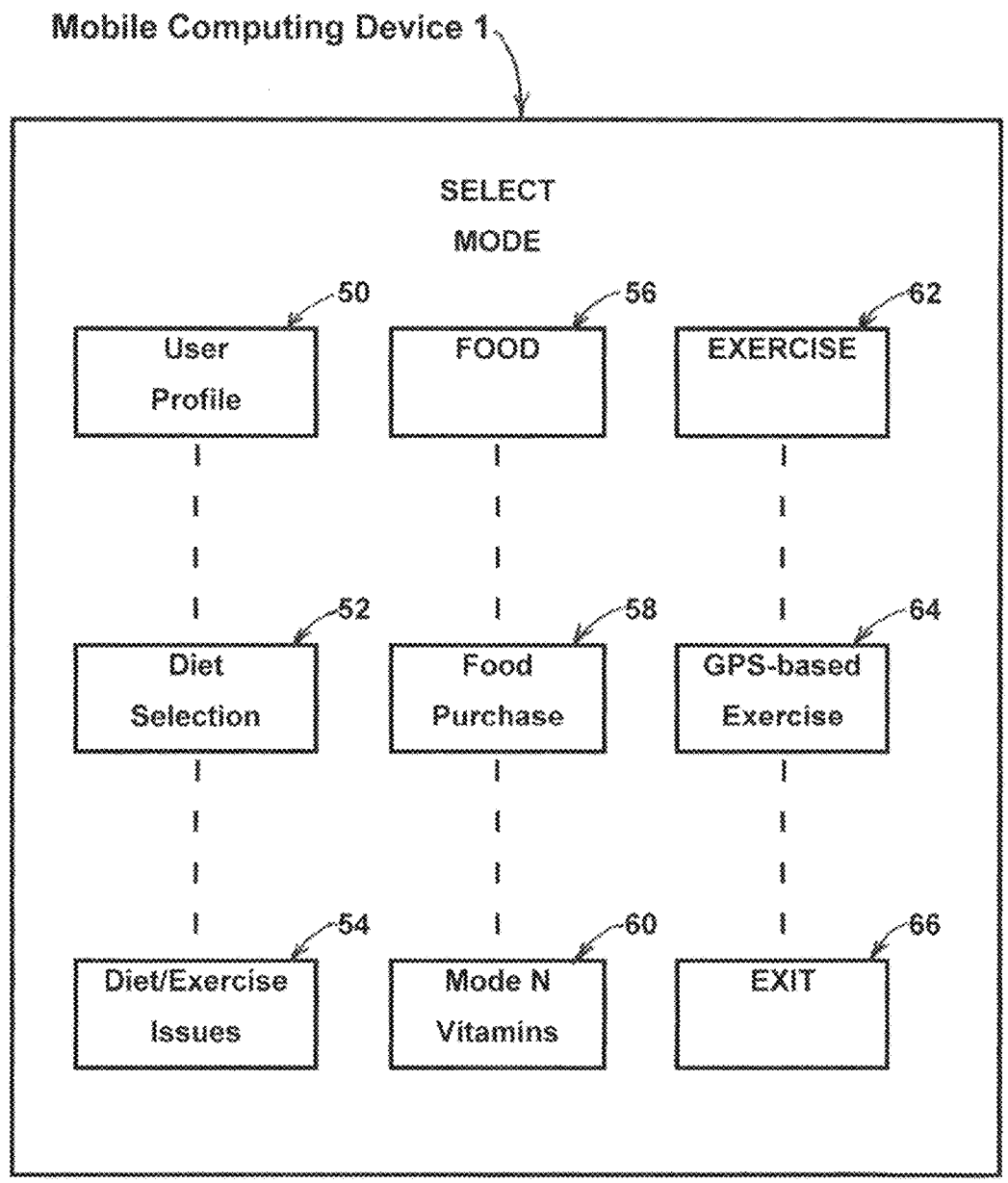
Figure 2B1

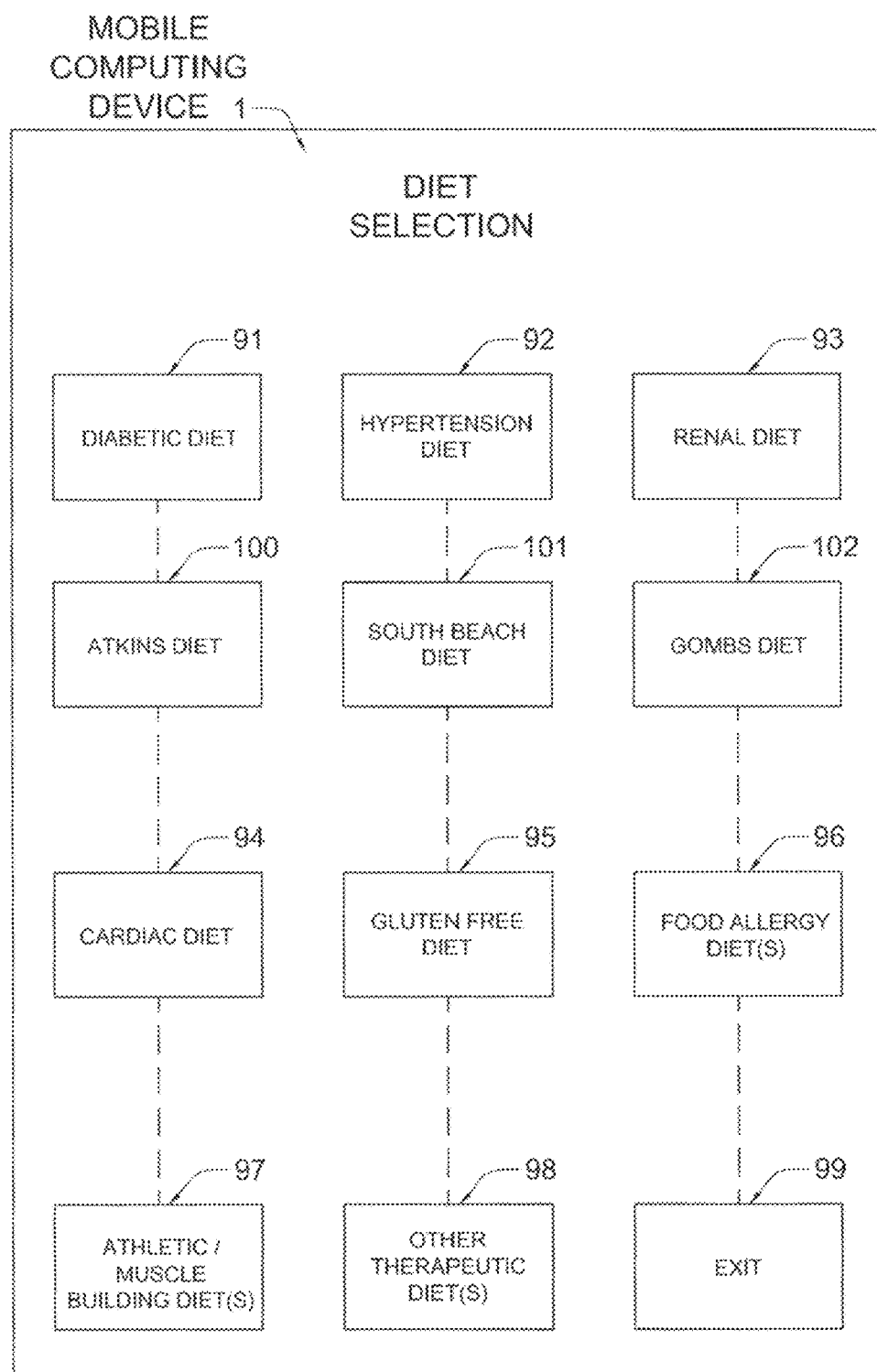
FIGURE 2B2

Color-Code Rating Scale Table
for each Food and Exercise being tracked

| RATING SCALE 280 | 281: 1 | 282: 2 | 283: 3 | 284: 4 | 285: 5 | 286: Superior |
|---|---|---|---|---|---|---|
| Stoplight Colors plus Blue Ribbon as worldwide conventions | Red | Orange | Yellow | Lime | Green | Blue |
| Relative Value | Worst 0% | Bad | Average 50% | Good | Best 100% | Blue Ribbon |
| 290 RATING EXAMPLES Below are range limits For 2 pairs of Ratings | | | | | | |
| 291 Healthy Nutrient Such as Protein/Omega-3s | < 20% | < 40% | < 60% | < 80% | < 100% | 100% Top 5 ** |
| 292 Unhealthy Nutrient such as TransFat/Cholesterol | > -100% | > -80% | > -60% | > -40% | > -20% | 0% Top 5 ** |
| Straight-Line Curves for linear functions such as a Vitamin/Mineral | < 20% Fewest MGs | < 40% Some | < 60% Average | < 80% More | < 100% Most MGs | > 100% Top 5 Sources |
| Changing-Rate Curves for non-linear functions such as Weight Loss | 0% toward Goal | < 40% first 40% | < 70% second 30% | < 90% third 20% | < 100% reach Goal | > 100% Blue Ribbon |

** The most accessible Top 5 items establish the 100% baseline for positive range limits
Conversely, the worst 5 items establish the -100% baseline for negative range limits

Figure 2C

Essential Nutrients for the Human Body: Macronutrients

| Color | Category | DV | Nutrient(s) plus their Daily Value (DV) at 2000 calories per day (in mgs) |
|---|---|---|---|
| | Macronutrients (also called *energy-producing nutrients*) | | |
| Grn | Calories | 2000 | *Energy* measured in Calories (*Cals*) where 2000 is now the DV baseline for all nutrients |
| Yel | Carbohydrates | 300g | *Carbs* include simple (sugars) vs. complex (fibers, starch) with a Glycemic Index (*GI*): |
| Grn | > good carbs | | *low GI* < 50: foods that help control *type 2 diabetes*, and improve *weight loss* |
| Red | > bad carbs | | *high GI* > 70: foods that create *high health risks* due to fast, strong rise in blood sugar |
| Yel | Sugars | NA | Single (Glucose, Fructose, Galactose) + Double (Sucrose, Maltose, Lactose) |
| Grn | Dietary Fiber | 25 g | Soluble (readily fermented in colon) + Insoluble (metabolically inert -- provides bulking) |
| | | | lowers LDL / helps regulate blood su; helps food pass through intestine |
| Yel | Cholesterol | 300 mg | *Total Cholesterol* = *HDL* + *LDL* + *Triglycerides* / 5 (saturated fatty acids in blood |
| Grn | > Optimal | | all 3 limits ===> above 60 *    below 100 *    below 100 * |
| Lime | > Normal | | below 200 *    60===>60    100===>130    100===>150    * mg per deci-Liter (mg / dL) |
| Yel | > Borderline | | 200===>240   women < 50    130===>160    150===>200    all cholesterol values shown |
| Orng | > Bad (High) | | above 240    men < 40    160===>190    above 200    are to interpret user test results |
| Red | > Very High | | above 190 |
| Yel | Dietary Fat | 65 g | *Total Fat* = Saturated (14 items) + Unsaturated (29 items) (see below) |
| Red | Saturated | 20 g | Sat. Fats from Meat/Dairy products + Trans-Fats (hydrogenated -- synthetic) |
| | (not essential nutrients) | | *Raise LDL / Raise Total Cholesterol*    *Raise LDL / Lower HDL* (worst of all outcomes) |
| Lime | Unsaturated | NA | Mono-Unsaturated (8) + Poly-Unsaturated (21) |
| | | | *lower LDL / boost HDL*    *lower LDL / lower Total Cholesterol*    (best of all outcomes) |
| Grn | > Poly-Unsaturated | | Fatty Acids (21 PUFAs) including 5 essential Omega Fatty Acids (below) |
| | | | *lower LDL / lower blood pressure / fight inflammation / protect brain & nervous system* |
| Blue | >> Omega-3 | NA | *EPA / DHA* (animal sources), Alpha-Linolenic Acid (*ALA*) (plant sources) (3 of 11) |
| Orng | >> Omega-6 | NA | Linoleic Acid (*LA*), Gamma-Linolenic Acid (*GLA*) (plant sources) (2 of 10) |
| Yel | > Mono-Unsaturated | | Fatty Acids (8 MUFAs), including just one essential Omega Fatty Acid |
| | >> Omega-9 | NA | Oleic Acid (*OA*) (1 of 8) |
| Grn | Protein | 50 g | 20 standard Amino Acids (out of 500 known AAs) including: |
| | > Essential | | 9 AAs that the human body cannot synthesize (must be obtained from food) including: |
| Blue | Amino Acids | | leucine**, isoleucine**, valine**, histidine, lysine, methionine, phenylalanine, threonine***, tryptophan |
| | RDA (mg) **** | 39 | 20    26    10    30    11    20    15    4 |
| ** | >> Branched-Chain | | 3 AAs stimulate building protein in muscle, and reduce muscle breakdown during exercise |
| *** | >> Threonine | | 1 AA that's often a low quantity in plant protein sources (must get it from other sources) |

Legend: "NA" means not established as a Daily Value      **** RDA (from WHO) in mgs per kg body weight (2.2 lbs)

Figure 2D1

Essential Nutrients for the Human Body: Micronutrients
All Nutrient and DV data taken from the USDA database @ http://www.ars.usda.gov/Services/docs.htm?docid=22114

| Color | Category | DV | Nutrient(s) plus their Daily Value (DV) at 2000 calories per day (in mgs) |
|---|---|---|---|
| Grn | Vitamins DV appears beneath each Vitamin/Mineral | | *A* (Retinol, Beta-carotene), *B* complex (B1, B2, B3, B6, B6, B7, B9, B12, Choline)<br>5000 IU    NA                        1.5  1.7  20  10  2  .300  .400  .006  NA |
| Grn | | | *C* (2), *D* (3), *E* Tocopherols (alpha/beta/delta/gamma) + Tocotrienols (a/b/d/g), *K* (3)<br>60       400                    30 IU  NA  NA  NA            NA              0.060 |
| Blue | Carotenoids (to maintain vision) | | Alpha-/Beta-/Gamma-carotene, Cryptoxanthin, Zeaxanthin, Lutein, Lycopene<br>NA    NA    NA                    NA          NA          NA       NA |
| Grn | Macro Minerals (> 100 mg/day) | | Calcium, Phosphorus, Potassium, Sulfur, Sodium, Chlorine, Magnesium<br>1000        1000        3500      NA      2400      3400      400<br>(7 essential minerals in the order of their abundance in the human body) |
| Grn | Micro Minerals (< 100 mg/day) | | Chromium, Copper, Iron, Iodine, Manganese, Molybdenum, Selenium, Zinc<br>0.120      2      18   0.150      2            .075            .070      15<br>(8 significant trace minerals in alphabetic order) |
| Blue | Trace Minerals (< 1 mg/day) | | Boron, Cobalt, Fluorine, Lithium, Nickel, Silicon, Strontium, Tin, Vanadium<br>NA    NA    NA    NA    NA    NA    NA    NA    NA<br>(9 additional trace minerals that have specialized roles) |

Legend: "NA" means not established as a Daily Value

Figure 2D2

Color Codes for Vitamin C: 100% Baseline established beneath the Top 5 sources Data Sources: http://foodinfo.us/SourcesUnabridged.aspx?Nutr_No=401 and http://en.wikipedia.org/wiki/Vitamin_C Items shown: only commonly-known and/or widely-available foods    Unit Amount: mgs / 100g (3.53 ounces)

Here are the Top 5 sources of C
that are widely available in stores.   Top #1     Top #2     Top #3    Red Pepper (190), Kale (120), Kiwifruit (93), Broccoli (89), Brussels Sprouts (85)   Top #4    Top #5

| Food Source | | Raw | Boiled | Frozen | Canned |
|---|---|---|---|---|---|
| Acerola | West Indian | 1677 | | | |
| Gooseberry | Indian | 445 | | | |
| Rose Hips | subtropical | 426 | | | |
| Chili Pepper * | green | 243 | | | |
| Guava | common | 228 | above items N/A in food stores | | |
| Pepper | red | 190 | 163 sauteed | | |
| Pepper | yellow, green | 184 | 177 sauteed | | |
| Blackcurrants | European | 181 | | | |
| Thyme | spice | 160 | | | |
| Chili Pepper * | red | 144 | | | |
| Parsley | | 133 | | | |
| Mustard Spinach | Indian | 130 | | | |
| Kale | | 120 | 65 | | |
| Jalapeno Pepper * | | 119 | 41 | 39 | Top #2 |
| Tomato | sun-dried, in oil | 101 | | | dried 101 |
| Taro | Tahitian | 98 | 38 | | |
| Kiwifruit | green | 93 | | | Top #3 |
| Broccoli | | 89 | 65 | 40 | Top #4 |
| Cauliflower | green | 88 | 73 | 49 | |
| Pimento, Dill Weed | | 85 | | | dried 50 |
| Brussels Sprouts | | 85 | 62 | 74 | Top #5 |
| 100% Baseline set @ > 80 mg ==> BLUE RIBBON level 6 | | | | | 15 |
| Redcurrants, Loganberry | | 80 | | | |
| Pepper | Red, Cayenne | 76 (spices) | | | |
| Onion | dehydrated | 75 | | | |
| Wolfberry | Goji | 73 | | | |
| Orange | with peel | 71 | | | |
| Mustard Greens | | 70 | | | |
| Persimmon | native | 66 | | | |
| Papaya | | 61 | | | |
| Peas | podded | 60 | 22 | | |
| Turnip Greens | | 60 | 27 | 22 | 16 |
| Orange | navel | 59 | | | |
| > 59 mg ==> GREEN Level 5 | | | | | |

* Chili Peppers are too hot for the general public

| Food Source | | Raw | Boiled | Frozen | Canned |
|---|---|---|---|---|---|
| Strawberry | | 59 | | 41 | |
| Chives | | 58 | | | |
| Cabbage | red | 57 | | | |
| Lemon | | 53 | | | |
| Orange | common | 53 | | | |
| Orange Juice | | 50 | | | |
| Tarragon | dried | 50 (spice) | | | |
| Orange | Valencia | 49 | | | |
| Cauliflower | white | 48 | | | |
| Orange | Florida | 45 | 44 | | |
| > 44 mg ==> LIME Level 4 | | | | | |
| Watercress | | 43 | | | |
| Cabbage | common | 42 | | | |
| Whitecurrants | | 41 | | | |
| Melon | Cantaloupe | 40 | | | |
| Grapefruit | pink/red/white | 39 | | | |
| Mango | | 36 | | | |
| Mulberries, Elderberries | | 36 | | | |
| Kidney Beans | boiled | 36 | 36 | | |
| Collards | | 35 | 26 | | |
| Tangerine, Mandarine | | 34 | | | |
| Asparagus | | 32 | 24 | 24 | 27 |
| Passion Fruit | | 30 | | | 19 |
| > 29 mg ==> YELLOW Level 3 | | | | | |
| Lime | | 29 | | | |
| Soybeans | green | 29 | 17 | | 14 |
| Spinach | | 28 | | | |
| Tomato/Vegetable Juice | | 28 | | | |
| Rasberry, Blackberry | | 26 | | 17 | |
| Tomato | ripe | 24 | 23 (cooked/stewed) | | |
| Turnips, Butternut Squash | | 21 | 18 | | |
| Potato, Sweet Potato | | 20 | 20 (baked in skin) | | |
| Melon | Honeydew | 18 | | | |
| > 14 mg ==> ORANGE Level 2 | | | | | |
| 0-14 mg ==> RED level 1 ** | | 17 | | | |
| Pineapple, Avocado | | | | | |
| Foods with 0 ==> 14 mg | | | | | |

** RED level 1 here means items with the lowest amount of C

| Recommended Daily Intake (RDI) adjusted for Body Weight, Physical Activity, and Age | | |
|---|---|---|
| Body Weight | Men | Women |
| 50 kg    110 lbs | *2,000 Kcal* (Daily Value) | 1,500 Kcal |
| 60 kg    132 lbs | *2,500 Kcal* | *2,000 Kcal* (Daily Value) |
| 70 kg    154 lbs | 3,000 Kcal | 2,500 Kcal |
| 80 kg    176 lbs | 3,500 Kcal | 3,000 Kcal |
| 90 kg    198 lbs | 4,000 Kcal | 3,500 Kcal |
| 100 kg   220 lbs | 4,500 Kcal | 4,000 Kcal |
| Physical Activity | Men | Women |
| Sedentary | 2,425 Kcal | 1,875 Kcal |
| Moderate | 2,875 Kcal | 2,225 Kcal |
| Heavy | 3,600 Kcal | 2,925 Kcal |
| Children | 1-3 years | 1,240 Kcal |
| | 4-6 years | 1,690 Kcal |
| | 7-9 years | 1,950 Kcal |
| Boys | 10-12 years | 2,190 Kcal |
| | 13-15 years | 2,450 Kcal |
| | 16-18 years | 2,640 Kcal |
| Girls | 10-12 years | 1,970 Kcal |
| | 13-15 years | 2,060 Kcal |
| | 16-18 years | 2,060 Kcal |
| Adult Men | 19-60 years | *2,500 Kcal* |
| | > 60 years | 2,250 Kcal  (-10%) |
| Adult Women | 19-60 years | *2,000 Kcal* |
| | > 60 years | 1,800 Kcal  (-10%) |
| Pregnant Women | (any age) | + 300 Kcal  (+15%) |
| Lactating Women | 0-6 months | + 550 Kcal  (+28%) |
| | 6-12 months | + 400 Kcal  (+20%) |

Figure 2G1

| Nutrient | Calories per day | 1800 | 2000 | 2200 | 2400 | 2500 |
|---|---|---|---|---|---|---|
| Protein | 10-25% | 45-112g | 50-125g | 55-138g | 60-150g | 63-156g |
| Carbohydrate | 45-65% | 203-293g | 225-325g | 248-358g | 270-390g | 281-406g |
| Fat | 20-30% | 40-60g | 44-67g | 49-73g | 53-80g | 56-83g |
| Saturated Fat | <10% | <20g | <22g | <24g | <26g | <28g |

Figure 2G2

| Meal / Dish | Breakfast (AM hours) | Lunch (Afternoon) | Dinner (PM hours) | Snacks (at any time) | Drinks (at any time) |
|---|---|---|---|---|---|
| 387 Drink + Add-Ons | Coffee + Cream | Iced Tea + Lemon | Martini + Garlic Olives | *(open-ended list below)**  | *(open-ended list below)** |
| 388 Appetizer + Sauce | Bagel + Cream Cheese | Guacamole + Sour Cream | Shrimp + Cocktail Sauce | Ice Cream + Syrup | Water + Ice |
| 389 Soup + Add-Ons | Chicken Noodle + Salted Crackers | Clam Chowder + Oyster Crackers | French Onion + Gruyere cheese | Pie + ala Mode | Regular Soda + Sugar |
| 390 Salad + Dressing | Cole Slaw + Vidalia Onion | Romaine Lettuce + Russian | Cobb Salad + Vinaigrette | Cake + ala Mode | Coffee + Cream |
| 391 Beef + Sauce | Sausage (or Bacon) | Hamburger + Mushrooms | Filet Mignon + Béarnaise | Chocolate (bars / pieces) | Hot Tea + Sweetener |
| 392 Poultry + Sauce | Egg Omelet + Salsa | Chicken Filet + Barbeque | Roast Turkey + Gravy | Candy (Candy Bars) | Milk + Chocolate |
| 393 Fish + Sauce | Smoked Salmon + Horseradish | Tuna Sandwich + Mayonnaise | Whole Lobster + Drawn Butter | Cookies + Raisins | Vegetable Juice |
| 394 Vegetable + Add-Ons | French Fries + Ketchup | Broccoli + Cheese | Ratatouille + Olive Oil | Chips + Onion Dip | Fruit Juice (or Drink) |
| 395 Grains*** + Add-Ons | Oat Cereal + Raspberries | Sourdough Bread + Butter | Pizza + Pepperoni | Crackers + Cheese Dip | Sports Drink (or Energy) |
| 396 Dessert + Sauce | Donut + Cream Filling | Ice Cream + Syrup | Cheesecake + Strawberry | Vegetables + Sour Cream | Beer (lite /regular) |
| 397 Fruit + Add-Ons | Banana (or Apple) | Fruit Cup + Whip Cream | Strawberries + Heavy Cream | Dried Fruit + Peanuts | Wine (Champagne) |
| 398 Dairy + Add-Ons | Yogurt + Blueberries | Skim Milk + Whey Powder | Milk Shake + Malt | Roasted Nuts + Sea Salt | Liquor + Mixer |

Food Database: Top 5 Favorite Meal Matrix for Breakfast, Lunch, Dinner, Snacks and Drinks *(examples of popular choices\* are displayed)*

380 → Meal/Dish; 381 → Breakfast; 382 → Lunch; 383 → Dinner; 384 → Snacks; 385 → Drinks \* Each example shown represents a unique *Open-Ended List* designed to stimulate User choices \*\* These 2 Open-Ended List categories are not related to the vertical Dish index in column 380

\*\*\* *Grains* are a broad Group that represents all varieties of *Bread, Cereal, Rice* and *Pasta*

Figure 3C

Exercise Database: Top 5 Favorite Exercises Matrix for Daily, Periodic, Sports, Conditioning and Weights *(examples of popular choices\* are displayed)*

| Exercise Mode | 481 Daily Work/School | 482 Periodic Home/Away | 483 Sports Competitive | 484 Conditioning Non-Competitive | 485 Weights Free/Machine |
|---|---|---|---|---|---|
| 487 Outdoor Body Only | *Work-Related Exercise below* | Wash Car Wax Car | Sprint Track & Field | Walk (User or GPS) | NA |
| 488 Outdoor Body Only | Sit/Stand Walk | Prune Garden Pull Weeds | Run (competitive) | Run/Jog (User or GPS) | NA |
| 489 Outdoor Equipped | Lift Load Carry Load | Mow Lawn Rake Leaves | Bike Track & Field | Bike/Skate (User or GPS) | NA |
| 490 Indoor Body Only | Sit/Stand Walk | Scrub Floors Clean Windows | Swim (competitive) | Swim Dance | Jumping Jacks Knee Bends |
| 491 Indoor Equipped | Lift Load Carry Load | Vacuum House Woodworking | Gymnastics (competitive) | Stationary Bike Rowing Machine | Seated Row Overhead Press |
| 492 Push Upper Body | *To/From Work listed below\*\** | Ping Pong + games | Basketball + position | Pushups Sit-ups | Bench Press Tricep Press |
| 493 Pull Upper Body | 498 Car Cab/Limo | Golf + rounds | Baseball + position | Pull-ups Back Extensions | Bicep Curl Cable Pull |
| 494 Push Lower Body | Bus Train/Plane | Volleyball + games | Football + position | Stair Stepper Elliptical Machine | Squats Leg Extensions |
| 495 Pull Lower Body | Walk Run | Badminton + games | Soccer Ice Hockey | Treadmill Cross-Country Ski | Leg Curl Hip Adductors |
| 496 Other (examples) | Bike NONE | Pool + racks | Tennis Martial Arts | Yoga/Pilates Karate Forms | Leg Press Hand/Wrist/Calf |

\* Each example shown here represents a unique Open-Ended List designed to stimulate the User
to select or add his/her own personal choices, which are then rotated to the top of that List
(e.g., for "Indoor Body Only": swim, dance, climb, Karate forms, Yoga, Pilates, Tai Chi, etc.)
\*\* This short open-ended list is not related to the vertical Mode index in the left-most column

Figure 3F

National Nutrient Database for Standard Reference
Release 25

Table 1.—Number of Foods in the Database (n = 8,194) Containing a Value for the Specified Nutrient

| Nutr. No. | Nutrient | Number of Foods | Nutr. No. | Nutrient | Number of Foods |
|---|---|---|---|---|---|
| 255 | Water | 8188 | 418 | Vitamin B-12 | 6966 |
| 208 | Energy (Calories) | 8194 | 578 | Vitamin B-12, added | 4257 |
| 203 | Protein | 8194 | 320 | Vitamin A, RAE | 6674 |
| 204 | Total lipid (fat) (#606→#859) | 8194 | 319 | Retinol | 6360 |
| 207 | Ash | 7855 | 321 | Carotene, beta | 4827 |
| 205 | Carbohydrate, by difference | 8194 | 322 | Carotene, alpha | 4740 |
| 291 | Fiber, total dietary | 7498 | 334 | Cryptoxanthin, beta | 4731 |
| 269 | Sugars, total | 6139 | 318 | Vitamin A, IU | 7479 |
| 210 | Sucrose (double sugar) | 1373 | 337 | Lycopene | 4705 |
| 211 | Glucose (dextrose) (mono) | 1376 | 338 | Lutein + zeaxanthin | 4681 |
| 212 | Fructose (monosaccharide) | 1375 | 323 | Vitamin E (alpha-tocopherol) | 5054 |
| 213 | Lactose (double sugar) | 1355 | | | |
| 214 | Maltose (double sugar) | 1343 | 573 | Vitamin E, added | 4082 |
| 287 | Galactose (monosaccharide) | 1225 | 341 | Tocopherol, beta | 1509 |
| 209 | Starch | 895 | 342 | Tocopherol, gamma | 1504 |
| 301 | Calcium, Ca (Minerals) | 7830 | 343 | Tocopherol, delta | 1489 |
| 303 | Iron, Fe | 8047 | 328 | Vitamin D (D2 + D3) | 4763 |
| 304 | Magnesium, Mg | 7451 | 325 | Vitamin D2 (ergocalciferol) | 52 |
| 305 | Phosphorus, P | 7570 | 326 | Vitamin D3 (cholecalciferol) | 1373 |
| 306 | Potassium, K | 7732 | 324 | Vitamin D (D1) | 4761 |
| 307 | Sodium, Na | 8111 | 430 | Vitamin K (phylloquinone) (K1) | 4620 |
| 309 | Zinc, Zn | 7437 | 429 | Dihydrophylloquinone | 1299 |
| 312 | Copper, Cu | 6977 | 428 | Menaquinone-4 | 477 |
| 315 | Manganese, Mn | 6159 | 606 | Fatty acids, total saturated (SFAs) | 7855 |
| 317 | Selenium, Se | 6425 | 607 | 4:0 | 5072 |
| 313 | Fluoride, F | 552 | 608 | 6:0 | 5117 |
| 401 | Vitamin C, total ascorbic acid (Vitamins) | 7395 | 609 | 8:0 | 5361 |
| | | | 610 | 10:0 | 5755 |
| 404 | Thiamin B-1 | 7473 | 611 | 12:0 | 6021 |
| 405 | Riboflavin B-2 | 7495 | 696 | 13:0 | 238 |
| 406 | Niacin B-3 | 7468 | 612 | 14:0 | 6395 |
| 410 | Pantothenic acid B-5 | 6179 | 652 | 15:0 | 1801 |
| 415 | Vitamin B-6 | 7201 | 613 | 16:0 | 6608 |
| 417 | Folate, total B-9 | 7042 | 653 | 17:0 | 2012 |
| 431 | Folic acid | 6391 | 614 | 18:0 | 6596 |
| 432 | Folate, food | 6590 | 615 | 20:0 | 2108 |
| 435 | Folate, DFE | 6381 | 624 | 22:0 | 1751 |
| 421 | Choline, total | 4192 | 654 | 24:0 | 1480 |
| 454 | Betaine | 1848 | 645 | Fatty acids, total (MUFAs) monounsaturated | 7491 |

FIGURE 4B1

| Nutr. No. | Nutrient | Number of Foods |
|---|---|---|
| 625 | 14:1 | 2010 |
| 697 | 15:1 | 1497 |
| 626 | 16:1 undifferentiated | 6359 |
| 673 | 16:1 c | 686 |
| 662 | 16:1 t | 566 |
| 687 | 17:1 | 1704 |
| 617 | 18:1 undifferentiated (Oleic Acid) | 6624 |
| 674 | 18:1 c | 1171 |
| 663 | 18:1 t | 1185 |
| 859 | 18:1-11t (18:1t n-7) | 154 |
| 628 | 20:1 | 5750 |
| 630 | 22:1 undifferentiated (Erucic Acid) | 5169 |
| 676 | 22:1 c | 604 |
| 664 | 22:1 t | 488 |
| 671 | 24:1 c | 788 |
| 646 | Fatty acids, total (PUFAs) polyunsaturated | 7498 |
| 618 | 18:2 undifferentiated (Linoleic Acid) | 6642 |
| 675 | 18:2 n-6 c,c | 1129 |
| 670 | 18:2 CLAs | 782 |
| 669 | 18:2 t,t | 216 |
| 666 | 18:2 i | 60 |
| 665 | 18:2 t not further defined | 651 |
| 619 | 18:3 undifferentiated (Linolenic Acid) | 6540 |
| 851 | 18:3 n-3 c,c,c (ALA) | 1308 |
| 685 | 18:3 n-6, c,c,c (GLA) | 1113 |
| 856 | 18:3i | 126 |
| 627 | 18:4 | 5101 |
| 672 | 20:2 n-6 c,c | 1784 |
| 689 | 20:3 undifferentiated | 1602 |
| 852 | 20:3 n-3 | 487 |
| 853 | 20:3 n-6 | 568 |
| 620 | 20:4 undifferentiated | 5761 |
| 855 | 20:4 n-6 | 7 |
| 629 | 20:5 n-3 (EPA) | 5183 |
| 857 | 21:5 | 102 |
| 858 | 22:4 | 630 |
| 631 | 22:5 n-e (DPA) | 5136 |
| 621 | 22:6 n-3 (DHA) | 5139 |
| 605 | Fatty acids, total trans | 2606 |
| 693 | Fatty acids, total trans-monoenoic | 1156 |
| 695 | Fatty acids, total trans-Polyenoic | 906 |
| 601 | Cholesterol | 7834 |
| 636 | Phytosterols | 514 |
| 638 | Stigmasterol | 128 |
| 639 | Campesterol | 127 |
| 641 | Beta-sitosterol | 128 |
| 501 | Tryptophan (Amino Acids) | 4797 |
| 502 | Threonine | 4843 |
| 503 | Isoleucine | 4847 |
| 504 | Leucine | 4846 |
| 505 | Lysine | 4860 |
| 506 | Methionine | 4857 |
| 507 | Cystine | 4786 |
| 508 | Phenylalanine | 4843 |
| 509 | Tyrosine | 4812 |
| 510 | Valine | 4847 |
| 511 | Arginine | 4832 |
| 512 | Histidine | 4840 |
| 513 | Alanine | 4789 |
| 514 | Aspartic acid | 4792 |
| 515 | Glutamic acid | 4792 |
| 516 | Glycine | 4789 |
| 517 | Proline | 4780 |
| 518 | Serine | 4790 |
| 521 | Hydroxyproline | 1175 |
| 221 | Alcohol, ethyl | 4887 |
| 262 | Caffeine | 4657 |
| 263 | Theobromine | 4633 |

FIGURE 4B2

| Fast Food vs Healthy Food<br>all items @ 220 grams<br>data from USDA Nutrient DB* ==><br>compare USDA vs Menu data ==> | | T.G.I. Friday's<br>Seasoned Fries<br>Food #36007 | | McDonald's<br>Big Mac<br>Food #21237 | | Sockey Salmon<br>cooked, dry heat<br>Food #15086 | | Turkey Breast<br>cooked, roasted<br>Food #05186 | |
|---|---|---|---|---|---|---|---|---|---|
| | | USDA | TGIF | USDA | McD's | (wild Pacific fish) | | (without skin) | |
| Macro-Nutrients | grams | RED food values highlighted | | | | GREEN food values highlighted | | | |
| *Calories* (Energy) | Cals | 677 | 290 | 563 | 520 | *372* | (low) | *325* | (low) |
| *Protein* | grams | *9.18* | 2 | 25.89 | 30 | *55.88* | | *66.59* | |
| *Total Fat* | grams | *33.88* | 22 | 32.76 | 26 | 14.72 | | *4.61* | (low) |
| > Saturated | (SFAs) | *6.35* | 4.5 | 13.76 | NA | *2.01* | (low) | *1.31* | (low) |
| > Mono-Unsat | (MUFAs) | 9.27 | | 15.57 | | *3.15* | (low) | *1.38* | (low) |
| > Poly-Unsat | (PUFAs) | 16.88 | | 0.93 | | 3.29 | | 1.17 | |
| > Trans-Fat | grams | 0.31 | 0 | *1.29* | NA | *0.05* | (low) | *0.05* | (low) |
| *Carbs* | grams | *84.02* | 21 | 43.98 | 46 | 0 | | 0 | |
| *Fiber* | grams | 6.11 | 2 | 3.51 | NA | 0 | | 0 | |
| *Sugars* (3 single + 3 double) | | 0.72 | NA | *8.69* | NA | 0 | | 0 | |
| Cholesterol | MGs | 2 | | 172 | | 139 | | 177 | |
| Minerals | MGs | only Sodium needs to be kept low | | | | only Sodium needs to be kept low | | | |
| Calcium | Ca | 40 | | 254 | | 26 | | 20 | |
| Iron | Fe | 2.18 | | 4.38 | | 1.11 | | 1.57 | |
| Magnesium | Mg | 79 | | 44 | | 79 | | 71 | |
| Phosphorus | P | 306 | | 267 | | 697 | | 508 | |
| Potassium | K | 505 | | 396 | | 898 | | 550 | |
| *Sodium* | Na | *842* | 980 | *1007* | 1100 | *295* | (low) | *219* | (low) |
| Zinc | Zn | 1.31 | | 1.91 | | 1.11 | | 3.81 | |
| Copper | Cu | 0.35 | | 0.11 | | 0.16 | | 0.14 | |
| Manganese | Mn | 0.61 | | 0.21 | | 0.03 | | 0.02 | |
| Selenium | Se | 0.009 | | 0 | | *0.081* | | *0.067* | |
| Vitamins | MGs | | | | | both are great sources of vitamins | | | |
| C (Ascorbic Acid) | MGs | 0 | | 0.9 | | 0 | | 0 | |
| Thiamin | B-1 | 0.274 | | 0.385 | | *0.473* | | 0.077 | |
| Riboflavin | B-2 | 0.036 | | 0.456 | | 0.306 | | *0.453* | |
| Niacin | B-3 | 6.53 | | 7.41 | | *21.34* | | *25.97* | |
| Pantothenic Acid | B-5 | 1.79 | | 0 | | *3.02* | | 1.99 | |
| Pyridoxine | B-6 | 0.57 | | 0 | | 1.53 | | *1.78* | |
| Folate (4) | B-9 | 0 | | 0.101 | | 0.02 | | *0.022* | |
| Cyanocobalamin | B-12 | 0 | | 0.002 | | *0.013* | | 0.001 | |
| A (3) (in IUs) | IUs | 0 | | 412 | | *455* | | 20 | |
| D (3) (in IUs) | IUs | 0 | | 0 | | *1167* | | 22 | |
| E (4 tocopherols) | Alpha | 2.97 | | 0 | | *2.51* | | 0.13 | |
| | Beta | 0.27 | | 0 | | *0.02* | | 0 | |
| | Delta | 5.78 | | 0 | | *0.48* | | 0.02 | |
| | Gamma | 17.03 | | 0 | | *0.42* | | 0.07 | |
| K (3) | MGs | 0.075 | | 0 | | 0.001 | | 0 | |
| | | <==end of Fast Food comparison==> | | | | <==Salmon/Turkey continue below==> | | | |
| Essential Amino Acids (9 of 20) | | RDA** ===> | | e.g., a 220-lb Man | | both are great sources of all 20 AAs | | | |
| Leucine | grams | 39 MGs / KG | | 3.9 | grams | *4.67* | 118% | *4.67* | 118% |
| Isoleucine | " | 20 | " | 2.0 | " | *2.69* | 135% | *1.91* | 96% |
| Valine | " | 26 | " | 2.6 | " | *3.08* | 118% | *3.13* | 120% |
| Histidine | " | 10 | " | 1.0 | " | *1.51* | 151% | *1.81* | 181% |
| Lysine | " | 30 | " | 3.0 | " | *5.43* | 181% | *5.49* | 183% |
| Methionine | " | 11 | " | 1.1 | " | *1.81* | 165% | *1.74* | 158% |
| Phenylalanine | " | 20 | " | 2.0 | " | *2.29* | 115% | *2.15* | 108% |
| Threonine | " | 15 | " | 1.5 | " | *2.63* | 176% | *2.42* | 161% |
| Tryptophan | " | 4 | " | 0.4 | " | *0.71* | 178% | *0.71* | 178% |

\* only 45 of 146 USDA nutrients are listed here    Figure 4C    \*\* RDA (from WHO) in MGs per KG body weight

Calorie Coefficient Database (per User * Activity for 30 minutes)
(continued on Figure 5B2)
*Exemplary User is a healthy large-frame 6'3" American Male (age 25) @ 200 lbs (Ideal Weight)*

Modulations: 170 lbs ==> Weight ==> 230 lbs (-0.181% per lb), 5' 6" ==> Height ==> 6' 6" (+0.6% per inch)
Modulations: 20 ==> Age ==> 70 (-0.323% per year), plus parallel modulations for Female @ 83.6% of Male

| WALKING | Calories Burned* | Coefficient | BIKING | Calories Burned* | Coefficient |
|---|---|---|---|---|---|
| Backpacking (Taylor Code 050) | 306 | 1.530 | Bicycling, Mountain, Uphill, Vigorous | 613 | 3.065 |
| Carrying 1 To 15 Lb Load, Upstairs | 219 | 1.095 | Bicycling, Mountain, Competitive | 700 | 3.500 |
| Carrying 16 To 24 Lb Load, Upstairs | 263 | 1.315 | Bicycling, Mountain, General | 372 | 1.860 |
| Carrying 25 To 49 Lb Load, Upstairs | 350 | 1.750 | Bicycling, On Dirt Or Farm Road | 254 | 1.270 |
| Carrying 50 To 74 Lb Load, Upstairs | 438 | 2.190 | Bicycling, Leisure, 5.5 Mph | 153 | 0.765 |
| Carrying > 74 Lb Load, Upstairs | 525 | 2.625 | Bicycling, Leisure, 9.4 Mph | 254 | 1.270 |
| Hiking, Cross Country (Code 040) | 263 | 1.315 | Bicycling, 12-14 Mph, Moderate Effort | 350 | 1.750 |
| Stair Climbing, Slow Pace | 175 | 0.875 | Bicycling, 14-16 Mph, Vigorous Effort | 438 | 2.190 |
| Stair Climbing, Fast Pace | 385 | 1.925 | GYM | Calories Burned* | Coefficient |
| Walking, Pleasure (Taylor Code 010) | 153 | 0.765 | Army Obstacle Course, Boot Camp | 219 | 1.095 |
| Walking, 2.0 Mph, Level,Firm Surface | 123 | 0.615 | Bicycling, Stationary, General | 306 | 1.530 |
| Walking, 2.5 Mph, Level,Firm Surface | 131 | 0.655 | Bicycling, Stationary, 30-50 Watts | 153 | 0.765 |
| Walking, 2.5 Mph, Downhill | 144 | 0.720 | Bicycling, Stationary, 51-89 Watts. | 210 | 1.050 |
| Walking, 5.0 Mph, Level,Firm Surface | 363 | 1.815 | Bicycling, Stationary, 90-100 Watts | 298 | 1.490 |
| Walking, 5.0 Mph, Uphill, 3% Grade | 429 | 2.145 | Bicycling, Stationary, 101-160 Watts, | 385 | 1.925 |
| RUNNING | Calories Burned* | Coefficient | Bicycling, Stationary, 161-200 Watts | 481 | 2.405 |
| Jog/Walk (less than 10 mins each) | 263 | 1.315 | Bicycling, Stationary, 201-270 Watts | 613 | 3.065 |
| Jogging, General | 306 | 1.530 | Calisthenics (Pushups, Pullups, etc) | 350 | 1.750 |
| Jogging, In Place | 350 | 1.750 | Calisthenics (Situps, Lunges, etc) | 166 | 0.830 |
| Running, Up Stairs | 350 | 1.750 | Calisthenics, light (Ab Crunches, etc) | 123 | 0.615 |
| Running, 4 Mph (13 Min/Mile) | 263 | 1.315 | Calisthenics, moderate (back bends) | 153 | 0.765 |
| Running, 5 Mph (12 Min/Mile) | 363 | 1.815 | Circuit Training, Moderate Effort | 188 | 0.940 |
| Running, 6 Mph (10 Min/Mile) | 429 | 2.145 | Circuit Training, Min Rest, Vigorous | 350 | 1.750 |
| Running, 7 Mph (8.5 Min/Mile) | 481 | 2.405 | Curvesim Exercise, Women | 153 | 0.765 |
| Running, 8 Mph (7.5 Min/Mile) | 503 | 2.515 | Elliptical Trainer, Moderate Effort | 219 | 1.095 |
| Running, 9 Mph (6.5 Min/Mile) | 538 | 2.690 | Resistance (Weights) (Code 210) | 263 | 1.315 |
| Running, 10 Mph (6 Min/Mile) | 560 | 2.800 | Resistance (Weights), Squats | 219 | 1.095 |
| Running, 11 Mph (5.5 Min/Mile) | 634 | 3.170 | Resistance (Weights), 8-15 Reps | 153 | 0.765 |
| Running, 12 Mph (5 Min/Mile) | 700 | 3.500 | Health Club Exercise (Code 160) | 241 | 1.205 |
| Running, 13 Mph (4.6 Min/Mile) | 831 | 4.155 | Health Club Exercise Classes | 219 | 1.095 |
| Running, Cross Country | 1006 | 5.030 | Health Club Conditioning Classes | 341 | 1.705 |
| Running, Marathon | 350 | 1.750 | Home Exercise, General | 166 | 0.830 |
| SWIMMING | Calories Burned* | Coefficient | Stair-Treadmill Ergometer, General | 394 | 1.970 |
| Swimming Laps, Freestyle, Vigorous | 429 | 2.145 | Rowing, Stationary Ergometer | 263 | 1.315 |
| Swimming Laps, Moderate Effort | 416 | 2.080 | Rowing, Stationary, Moderate Effort | 210 | 1.050 |
| Swimming, Backstroke, Recreational | 210 | 1.050 | Rowing, Stationary, 100 Watts | 306 | 1.530 |
| Swimming, Backstroke, Competition | 254 | 1.270 | Rowing, Stationary, 150 Watts | 372 | 1.860 |
| Swimming, Breaststroke, Recreational | 232 | 1.160 | Rowing, Stationary, 200 Watts | 525 | 2.625 |
| Swimming, Breaststroke, Competition | 451 | 2.255 | Ski Machine, General | 298 | 1.490 |
| Swimming, Butterfly, General | 604 | 3.020 | Slide Board Exercise, General | 481 | 2.405 |
| Swimming, Crawl, 75 Yards/Minute | 438 | 2.190 | Gimnastics, Jazzercise | 263 | 1.315 |
| Swimming, Crawl, 50 Yards/Minute | 363 | 1.815 | Tai Chi (or) Pilates, General | 131 | 0.655 |
| Swimming, Lake, Ocean, River | 263 | 1.315 | Therapeutic Exercise Ball, Fitbal | 123 | 0.615 |
| Swimming, Leisurely, General | 263 | 1.315 | Upper Body Exercise,Arm Ergometer | 123 | 0.615 |
| Swimming, Sidestroke, General | 306 | 1.530 | Upper Body Exercise, Airdyne40Rpm | 188 | 0.940 |
| Swimming, Treading Water,Moderate | 153 | 0.765 | Water Aerobics, Water Calisthenics | 188 | 0.940 |

Figure 5B1

Calorie Coefficient Database (per User * Activity for 30 minutes)
(continued from Figure 5B1)
*Exemplary User is a healthy large-frame 6'3" American Male (age 25) @ 200 lbs (Ideal Weight)

| SPORTS (continued) | Calories Burned* | Coefficient | SPORTS (continued) | Calories Burned* | Coefficient |
|---|---|---|---|---|---|
| Archery, Non-Hunting | 188 | 0.940 | Rock Climbing, Traversing Rock | 254 | 1.270 |
| Badminton, Competitive (Code 450) | 306 | 1.530 | Rock Climbing, Rappelling | 219 | 1.095 |
| Badminton, Social, General | 241 | 1.205 | Rope Jumping, 120-160 Skips/Min | 538 | 2.690 |
| Baseball or Softball (TaylorCode 440) | 350 | 1.750 | Rope Jumping, 100-120 Skips/Min | 516 | 2.580 |
| Basketball, Game (Taylor Code 480) | 350 | 1.750 | Rope Jumping, < 100 Skips/Min | 385 | 1.925 |
| Basketball, Social (Taylor Code 480) | 263 | 1.315 | Rugby, Union, Team, Competitive | 363 | 1.815 |
| Billiards | 109 | 0.545 | Rugby, Touch, Non-Competitive | 276 | 1.380 |
| Bowling (Taylor Code 390) | 131 | 0.655 | Skateboarding, Moderate Effort | 219 | 1.095 |
| Bowling, Indoor, Bowling Alley | 166 | 0.830 | Skateboarding, Competitive,Vigorous | 263 | 1.315 |
| Boxing, In Ring, General | 560 | 2.800 | Skating, Roller (Taylor Code 360) | 306 | 1.530 |
| Boxing, Punching Bag | 241 | 1.205 | Rollerblading, 14.4 Km/H (9.0 Mph) | 328 | 1.640 |
| Boxing, Sparring | 341 | 1.705 | Rollerblading, 17.7 Km/H (11.0 Mph) | 429 | 2.145 |
| Cheerleading,Gymnastic,Competitive | 263 | 1.315 | Rollerblading, 21.0+ Km/H (13+ Mph) | 538 | 2.690 |
| Fencing, General | 263 | 1.315 | Rollerblading, 24.9 Km/H (15.5 Mph) | 613 | 3.065 |
| Football, Competitive | 350 | 1.750 | Skydiving, Base & Bungee Jumping | 153 | 0.765 |
| Football, Touch, Flag (Code 510) | 350 | 1.750 | Soccer, Competitive | 438 | 2.190 |
| Football, Touch, Flag, Light Effort | 175 | 0.875 | Soccer, Casual (Taylor Code 540) | 306 | 1.530 |
| Golf, Walking, Carrying Clubs | 188 | 0.940 | Softball or Baseball (TaylorCode 440) | 219 | 1.095 |
| Golf, Power Cart (Taylor Code 070) | 153 | 0.765 | Softball,Pitching | 263 | 1.315 |
| Gymnastics, General | 166 | 0.830 | Table Tennis, Ping Pong (Code 410) | 175 | 0.875 |
| Handball, Jai Alai (Taylor Code 520) | 525 | 2.625 | Tennis, General | 319 | 1.595 |
| Handball, Team | 350 | 1.750 | Tennis, Doubles (Taylor Code 430) | 263 | 1.315 |
| Hockey, Field (or) Lacrosse | 341 | 1.705 | Tennis, Doubles | 197 | 0.985 |
| Hockey, Ice, General | 350 | 1.750 | Tennis, Singles (Taylor Code 420) | 350 | 1.750 |
| Hockey, Ice, Competitive | 438 | 2.190 | Volleyball (Taylor Code 400) | 175 | 0.875 |
| Lacrosse, General | 350 | 1.750 | Volleyball, Competitive, In Gym | 263 | 1.315 |
| Martial Arts, Novice, Practice | 232 | 1.160 | Volleyball, Non-Compstitive, 6 - 9 | 131 | 0.655 |
| Martial Arts(Judo, Jujitsu, Karate, etc) | 451 | 2.255 | Volleyball, Beach, In Sand | 350 | 1.750 |
| Racquetball, Competitive | 438 | 2.190 | Wrestling (One Match = 5 Minutes) | 263 | 1.315 |
| Racquetball (Taylor Code 470) | 306 | 1.530 | Track And Field (Shot, Discus) | 175 | 0.875 |
| Rock Climbing (Taylor Code 470) | 350 | 1.750 | Track & Field ( High Jump,Pole Vault) | 263 | 1.315 |
| Rock Climbing, Ascending, Difficult | 328 | 1.640 | Track And Field (E.G., Hurdles) | 438 | 2.190 |

Figure 5B2

| Overweight/Obese Risk Table | | | |
|---|---|---|---|
| Healthy (baseline) <=== versus ===> Overweight or Obese (avg % increase) | | | |
| Rank | Higher Risk | Overweight | Obese |
| 1 | Esophageal Cancer | 590% | 1,520% |
| 2 | Type 2 Diabetes | 360% | 1,020% |
| 3 | Stomach Cancer | 120% | 330% |
| 4 | Gallstones | 90% | 150% |
| 5 | High Blood Pressure | 70% | 170% |
| 6 | Heart Disease | 50% | 100% |
| 7 | Total Cholesterol > 250 | 50% | 122% |
| 8 | Higher Cost of Drugs | 37% | 105% |
| 9 | Kidney Cancer | 35% | 70% |
| 10 | Die of any Cause | 31% | 62% |
| 11 | Asthma | 20% | 50% |
| 12 | Longer Stays in Hospital | 19% | 49% |
| 13 | Die in a Car Crash | 19% | 37% |
| 14 | Die of First Heart Attack | 16% | 49% |
| 15 | Less Attractive to Opposite Sex | 14% | 43% |
| 16 | Osteoarthritis | 14% | 34% |

Figure 6C

User DB Format: Weight Loss Plan

Figure 7A1

| START 689 | | Weight Loss Deltas 693 | | | | GOAL 697 | |
|---|---|---|---|---|---|---|---|
| Category | Weight | delta 1 | delta 2 | delta 3 | delta 4 | Weight | Category |
| Level | Date | weeks | weeks | weeks | weeks | Time | Level |
| Tag: Color Code | | Lowest | Next Higher | | Highest | Reward: for reaching Goal | |

**Illustrative Example: large-frame Obese American Male * @ 5' 9.4"**
Goal: Obese ==> Overweight ==> Healthy ==> Ideal Weight

Figure 7A2

Obese ==> Overweight     Cumulative Time ==> 6 Months     Loss ==> 40 lbs

| START 689 | | Weight Loss Deltas 693 | | | | GOAL 697 | |
|---|---|---|---|---|---|---|---|
| Obese | 236 lbs | -13 | -11 | -9 | -7 | 196 lbs * | Overweight |
| Mid+ | 0 weeks | +7 | +6 | +7 | +6 | 6 months | Max |
| Color-Code Rating | | RED | Orange | Orange | Yellow | Reward: 40 iTunes | |

Figure 7A3

Overweight ==> Healthy     Cumulative Time ==> 6 Months     Loss ==> 20 lbs

| START 689 | | Weight Loss Deltas 693 | | | | GOAL 697 | |
|---|---|---|---|---|---|---|---|
| Overweight | 196 lbs * | -6 | -5 | -5 | -4 | 176 lbs | Healthy |
| Max | 26 weeks | +7 | +6 | +7 | +6 | 12 months | Max |
| Color-Code Rating | | Yellow | Lime | Lime | GREEN | Reward: 4 iMovies or iBooks | |

Figure 7A4

Healthy ==> Ideal Weight     Cumulative Time ==> 3 Months     Loss ==> 10 lbs

| START 689 | | Weight Loss Deltas 693 | | | | GOAL 697 | |
|---|---|---|---|---|---|---|---|
| Healthy | 176 lbs | -4 | -3 | -2 | -1 | 166 lbs | Ideal Weight |
| Max | 52 weeks | +5 | +3 | +2 | +2 | 15 months | Low Body Fat |
| Color-Code Rating | | Green | Aqua ** | Aqua ** | BLUE | Reward: Wild Salmon Dinner | |

\* Average Weight/Height for American Males is 196 lbs @ 5' 9.4"

\*\* The blue-green color "Aqua" is added here as an intermediate incentive

FIGURE 7B4
FIGURE 7B3
FIGURE 7B2
FIGURE 7B1

| User Profile Record Format 720 | |
|---|---|
| Data Item 721 | Qualifier(s) 722 |
| User ID Data List 723 | |
| User ID # | assigned by system |
| Rev Level * | original Create Profile record = Rev 1 * |
| Date Time | initial user contact |
| Device # | e.g., unique cellphone ID |
| Email Address | optional: as alternate link |
| User Name | plus unique modifier |
| Sex | M or F |
| Age | optional: user provides Birthday |
| Height | to nearest inch (optional: to nearest 1/4") |
| Wrist Size | to establish body frame (to nearest 1/4") |
| Waist Size | to establish obesity level (to nearest 1/4") |
| ID Flag | flag for any user ID change (challenged by system) |
| Weight0 | current user-declared weight now (to nearest pound) |
| Weight5 | optional: user weight 5 years ago |
| Weight10 | optional: user weight 10 years ago |
| Weight Ideal | system provides this (based on all above user data) |
| Weight Flag | flag for any user weight change (e.g., expected updates) |
| GoalW | lose (gain) weight (optional: pounds) |
| GoalS | get stronger (e.g., > Top 5 weightlifting exercises) |
| GoalE | more endurance (e.g., > Top 5 endurance exercises) |
| GoalH | get healthier (e.g., better than Top 5 foods/vitamins) |
| GoalD | drop bad habits (e.g., smoking/drinking/drugs/addictions/etc.) |
| Goal Date | optional: set by user (otherwise, set by system) |
| Goal Flag | flag for any user goal change (forces system recalc) |
| RewardDS | lowest level reward for reaching Delta Subgoals |
| RewardFG | highest level reward for reaching Final Goal |
| RewardBR | Blue Ribbon reward for superior performance |
| User Health Data List 724 | |
| Level0 | general level of health now (as declared by user) |
| Level5 | optional: user-declared level of health 5 years ago |
| Level10 | optional: user-declared level of health 10 years ago |
| Handicaps | 1 ==> N as declared by user (codified by system) |
| Handicaps5/10 | each above handicap 5/10 years ago (open-ended list) |
| Ailments | 1 ==> N as declared by user (codified by system) |
| Ailments5/10 | each above ailment 5/10 years ago (open-ended list) |
| Injuries | 1 ==> N as declared by user (open-ended list) |
| Weak Flag | one flag set for each weak limb/muscle (e.g., on one side) |
| Range Flag | one flag set for each limb/muscle with limited range |
| Habits | 1 ==> N (smoking/drinking/drugs/food addictions/etc.) |
| Meds | 1 ==> N as declared by user (for all the above debilities) |
| RestrictF | Foods excluded due to above data (open-ended list) |
| RestrictE | Specific exercises limited or excluded (open-ended list) |

* a new record @ Rev = N + 1 is created for each set of user changes

Figure 8A

| User Profile/Food Record Format 728 ||||||
|---|---|---|---|---|---|
| Provided by User 730 |||| Provided by System 731 ||
| 738⤵ | 739⤵ Top 5 Favorite Foods/Meals 729 | | 742⤵ | 743⤵ ||
| Category B/L/D * | Add-Ons Add1 Add2 | Qty 740 | CALS IN 741 | Macro-Nutrients Carbs/.../Protein | Micro-Nutrients Vitamins/Minerals |
| 732 Drink Appetizer Soup Salad | Add-On Add-On Sauce Add-On Dressing | Oz | Cals | MGs/.../MGs | MGs/.../MGs |
| 733 Beef Chicken Fish Vegetable | Sauce Add-On Sauce Sauce Add-On | Oz | Cals | MGs/.../MGs | MGs/.../MGs |
| 734 Grains Dessert Fruit Dairy | Add-On Add-On Sauce Add-On Add-On | Oz | Cals | MGs/.../MGs | MGs/.../MGs |
| 735 Snacks** Drinks** | Add-On Add-On Add-On Add-On | Oz Oz | Cals Cals | MGs/.../MGs MGs/.../MGs | MGs/.../MGs MGs/.../MGs |
| 736 Totals Vitamins/Minerals/Antioxidants *** 737 System Recommendations | | Oz 744 | Cals | Carbs/.../Protein User favorites stored here ==> MGs System recs stored here ==> MGs | MGs MGs MGs MGs |

\* the cycle of 12 dishes here repeats up to 5 times each for Breakfast/Lunch/Dinner (BLD)

\*\*Snacks and Drinks are open-ended lists to store from 1 ==> N items the user may eat \*\*\* optional: user enters his/her vitamins/minerals into an open-ended list for each nutrient
(see essential vitamins/minerals/antioxidants in Figure 2E)

Figure 8B

| User Profile/Exercise Record Format 760 ||||||| 
| All Data provided by User (except CALS OUT calculated by System) |||||||
| Top 5 Favorite Exercises/Activities  747  759  761 |||||||
| Category D/P/S/C/W * | Exercise Level  Item | Qty | Time/ Duration | Fre-quency | Cycle Goals/Sets  Trials/Reps | CALS OUT |
|---|---|---|---|---|---|---|
| 748 Daily Activity | | 756 | 757 | 758 | | |
| Indoor/ Outdoor | Work/ Activity School | pounds/ distance | hours/ minutes | per day/ per week | | Cals |
| 749 Periodic Activity | | | | | | |
| Indoor/ Outdoor | Home/ Activity Away | | hours/ minutes | per day/ per week | | Cals |
| 750 Sports (competitive and non-competitive) | | | | | | |
| Indoor/ Outdoor | Team ** / Sport *** Individual  Trial **** | quarters/ distance | hours/ minutes | per day/ per week | Goal1  Trial1 (1st of N goals) | Cals |
| 751 Conditioning (non-competitive) | | | | | | |
| Indoor/ Outdoor | Machine/ Exercise/ Body Only  Trial **** | distance/ resistance | hours/ minutes | per day/ per week | Goal1  Trial1 (1st of N goals) | Cals |
| 752 Weightlifting (non-competitive) | | | | | | |
| Lower body/ Upper body | Machine/ Exercise/ Body Only  Lift **** | pounds1/ distance | hours/ minutes | per day/ per week | Set1  Reps1 (1st of N sets) | Cals |
| 753 Multiple Trials/Sets 1 ==> N (of same quick "burst-energy" exercise) | | | | | | |
| *multiple trials/sets 1 ==> N are appended to the initial trial1/set1 record in the following format:* ||||||| 
| Trial/Set N Pass/Fail | Target Pulse Range 60% ==> 85% | poundsN/ distanceN | Rest interval | Pulse Rate | Goal/SetN  Trial/RepsN attempted/completed | Cals |
| 755 Totals | Activities/Lifts | Qty | Hours | Workouts | Reps  Sets | Cals |

\* data entry cycle here repeats up to 5 times for daily/periodic/sports/conditioning/weights (D/P/S/C/W)

\*\* each Team Sport is qualified by the user's Position on that team (e.g., goalie/pitcher/QB/guard/etc)

\*\*\* each Sport is qualified at the user's performance level of competition (which modulates Cals Out) as Training Only / Recreational / Middle School / High School / College / Club Sport / Semi-pro / Pro \*\*\*\* for fast "burst-energy" Sports/Lifts, a separate record is added for each trial/set/race/vault/jump/etc

Figure 8C

Body Frame: How to Determine Small, Medium, or Large

| 1> Men – Wrist Sizes | | Women – Wrist Sizes | | |
|---|---|---|---|---|
| Body Frame | Height over 5' 5" | Height under 5' 2" | Height 5' 2" - 5' 5" | Height over 5' 5" |
| Small | 5.5" - 6.5" | Under 5.5" | Less than 6.0" | Less than 6.25" |
| Medium | 6.5" - 7.5" | 5.5" - 5.75" | 6" - 6.25" | 6.25" - 6.5" |
| Large | Over 7.5" | Over 5.75" | Over 6.25" | Over 6.5" |

FIGURE 12A

| 2> | | Elbow Measurements for Medium Frame | | | |
|---|---|---|---|---|---|
| Height Range | | Men's Range | | Women's Range | |
| 6' 4" | 6' 6" | 2-7/8" | 3-1/4" | 2-1/2" | 2-3/4" |
| 6' 0" | 6' 3" | 2-3/4" | 3-1/8" | 2-1/2" | 2-3/4" |
| 5' 8" | 5' 11" | 2-3/4" | 3-0" | 2-3/8" | 2-5/8" |
| 5' 4" | 5' 7" | 2-5/8" | 2-7/8" | 2-3/8" | 2-5/8" |
| 5' 0" | 5' 3" | 2-1/2" | 2-7/8" | 2-1/4" | 2-1/2" |
| 4' 10" | 4' 11" | 2-1/2" | 2-3/4" | 2-1/4" | 2-1/2" |

Figure 12B

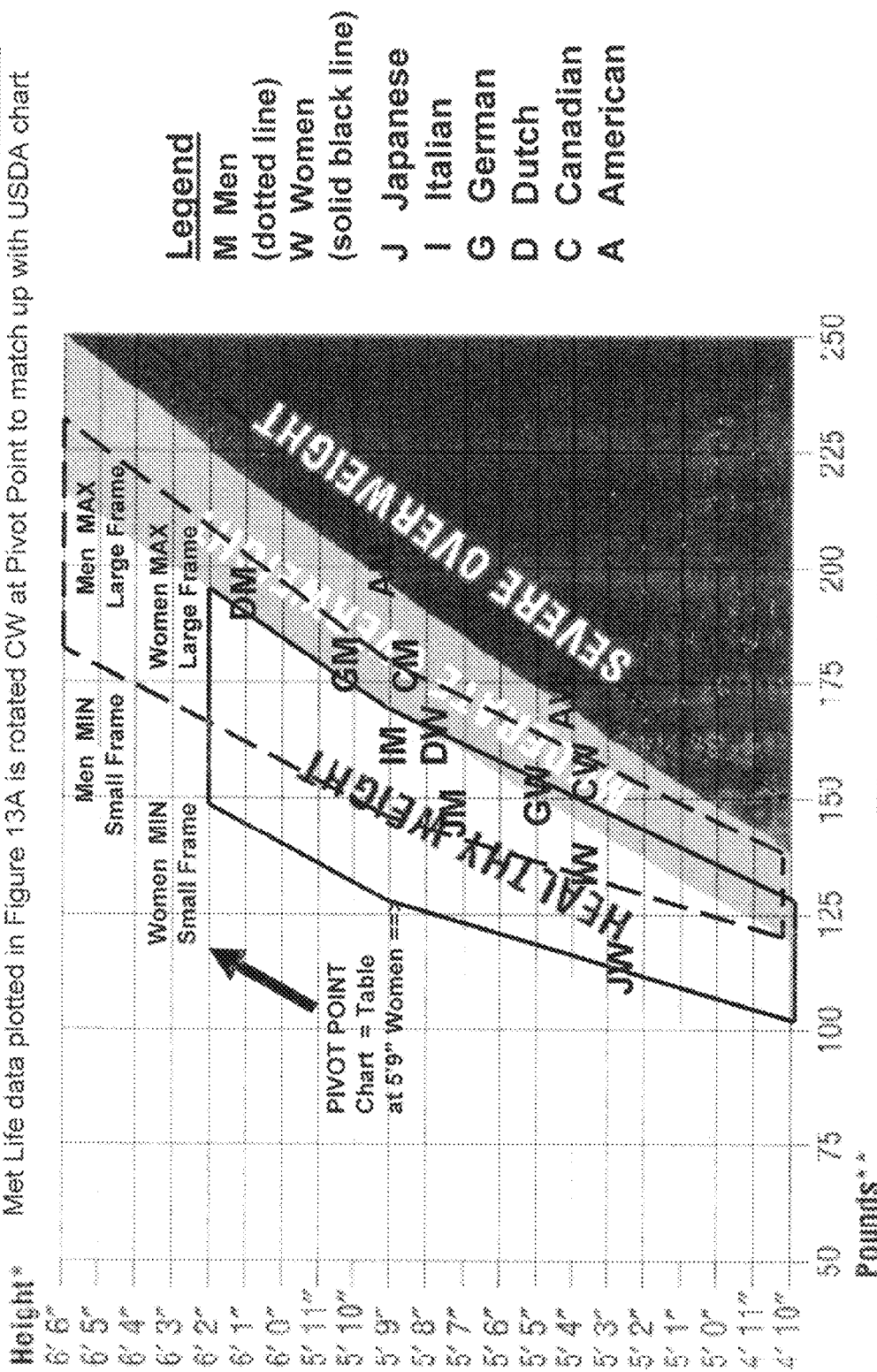

MOBILE COMPUTING WEIGHT, DIET, NUTRITION, AND EXERCISE MANAGEMENT SYSTEM WITH ENHANCED FEEDBACK AND GOAL ACHIEVING FUNCTIONALITY

This application is a continuation of allowed U.S. patent application Ser. No. 15/361,383, filed on Nov. 26, 2016, which is a continuation of U.S. patent application Ser. No. 15/175,296, filed on Jun. 7, 2016, now U.S. Pat. No. 9,514,655, which is a continuation of U.S. patent application Ser. No. 15/047,817, filed on Feb. 19, 2016, now U.S. Pat. No. 9,378,657, which is a continuation of U.S. patent application Ser. No. 14/242,106, filed on Apr. 1, 2014, now U.S. Pat. No. 9,280,640, which is a continuation of U.S. patent application Ser. No. 13/733,588, filed on Jan. 3, 2013, now U.S. Pat. No. 8,690,578, which are hereby incorporated by reference in their entirety.

FIELD OF THE INVENTION

The invention generally relates to a computing diet, nutrition and exercise tracking system and methodology. More particularly, the illustrative implementations relate to a mobile computing weight, diet, nutrition, behavioral, and exercise tracking system with enhanced data acquisition functionality to ease tracking calories consumed and calories burned through exercise while providing enhanced user feedback features to improve the probability of goal achievement.

BACKGROUND AND SUMMARY

Obesity has been a well-recognized serious health problem in the United States for decades, significantly contributing to shortening lives and increasing medical expenses for millions of Americans. Many diseases, such as type II diabetes, hypertension, hyperlipidemia, heart disease, and others have been directly linked to obesity. Unfortunately, the threat of a reduced lifespan, reduced quality of life and an enhanced probability of suffering from comorbid diseases in the future is not sufficient for those who are significantly overweight to be successful in reducing their weight and in maintaining such a reduced weight, and a healthy lifestyle incorporating a consistent exercise program.

The causes of obesity are multiple and can be complex. Genetic predisposition impacting metabolism and environmental factors such as diminished physical activity often play a key role. For some individuals additional psychological factors such as stress and depression and medical conditions such as hypothyroidism, chronic pain and other conditions that restrict physical activity or affect metabolism all can contribute in varying degrees in causing obesity.

Given the complexity of obesity, there are many approaches to its treatment. At the most basic level, treatment involves the manipulation of energy intake and energy expenditure. To lose weight one has to take in fewer calories than one expends. To attain this objective, diets limiting the intake of calories are typically coupled with exercise to increase energy expenditure and thus create negative energy balance. Along with this, however, when restricting calories one must be aware of the nutritional needs of the body. Healthy weight loss is best achieved when nutritional requirements of the body are fulfilled during the process of limiting caloric intake.

Since many individuals suffering from obesity also are afflicted with comorbid medical conditions, the determination of appropriate nutritional intake, caloric restriction and exercise regimens should take into account these conditions and, often, the medications associated with them. Safety is of utmost concern when establishing an exercise regimen and in determining nutritional requirements making up a dietary protocol. For example, an appropriate dietary protocol and exercise regimen for weight loss for a 60 year old morbidly obese male individual with hypertension, coronary artery disease and history of heart attack would be very different than the appropriate protocol for a 38 year old moderately obese female having type II diabetes treated with oral medications. Given these factors, it is recommended that protocols for weight loss including nutritional guidelines and exercise be constructed by healthcare professionals including physicians, nutritionists and others.

In this country, there is significant variation in the approaches available to address obesity. Many commercial programs exist, such as Weight Watchers, that provide nutritional and exercise direction along with help to keep on track. There are many individual health care professionals that provide specific weight management services such as nutritionists, trainers, exercise physiologists, counselors, psychologists, nurses and physicians. In some areas, there are more comprehensive programs available at multidisciplinary medical weight management centers where medical management, nutrition, exercise and psychological intervention are provided in a global, coordinated approach. Also, there are surgical approaches available offering a number of procedures aimed at altering caloric intake and absorption.

In addition to services and programs, there are a myriad of weight loss products available. FDA approved prescription medications, herbal products and over the counter products to stimulate metabolism and to increase satiety, prepackaged, low and zero calorie foods and beverages and many other products are available to alter caloric intake. Exercise machines, devices and videos are also available to encourage increased energy expenditure.

In the end, the success of individuals, whether it be in losing weight and maintaining the weight loss or any health enhancement endeavor is most affected by their ability to make positive behavior changes and to maintain those positive behaviors indefinitely.

Well known programs, such as Weight Watchers, have employed weight-loss monitoring data processing systems that have been helpful to participants in this program. In recent years, weight-loss applications have become available for use with iPhones and iPads to assist dieters in successfully meeting their weight loss goals.

While existing weight-loss computing systems have a variety of useful features, such systems are typically cumbersome to use due in part to the complexities of adequate data entry. The difficulties in various data entry steps in such systems are likely to discourage consistent use over a long period of time for many users.

Moreover, there is a need for a diet, exercise and behavioral monitoring system that provides the user with a structured system for addressing the old adage "you are what you eat" in part by providing feedback in real time to the user as to food consumed, exercise performed and/or progress towards goal achievement. In illustrative implementations, such feedback includes nutritional and/or health information about food items to be consumed of which the user may be unaware. Armed with such information, the user is then equipped to make an informed decision whether to eat a selected food item. With such a system, even those who are not overweight (or suffering from any known illness) but who wish to structure a diet that minimizes their odds of in the future suffering from a variety of diseases linked to poor diet, have an opportunity to do so. Still others, who are not overweight but who suffer from high blood pressure, diabetes, lipid disorders, renal disease and perhaps various cancers, have an opportunity to meet their food consumption and exercise goals to take advantage of a diet and exercise protocol that has been linked to helping control such medical conditions. Also individuals in good health who may have very specific health and fitness goals such as bodybuilders, runners, martial arts enthusiasts and others may utilize such a system to help attain their fitness and health goals by monitoring and tracking exercise, behavioral and nutrition parameters.

There is a need for an easy to use weight, nutrition, exercise and behavior monitoring data processing system that, for example, simplifies data entry for food consumed and/or exercise modes of operation and/or behavior parameters, while providing valuable health beneficial feedback and rewards for behavior change and goal achievement. Former smokers and those who are attempting to quit smoking have a dire need to eat in a nutritionally sound manner, exercise as much as they are able, and be rewarded for their efforts to stop smoking. Moreover, it is desirable for such a system to, for example, dynamically adjust to changing user food intake, exercise regimens and behaviors, to change user profiles and associated goals, and to appropriately generate medical warnings as needed.

In practical effect, in illustrative implementations, the mobile computing device executing the weight, nutrition, health, behavior and exercise application software as described herein serves as a simulated personal trainer, dietician/nutritionist, and physician's assistant for the user while having access to massive amounts of personalized health, nutrition and exercise information. In non-limiting, illustrative implementations, a mobile computing device, such as an Iphone, is augmented with a unique weight, nutrition, health, behavior and exercise tracking application and databases that provide enhanced user feedback features and automated data entry.

The illustrative implementations advantageously contribute to the ability of users to maintain positive diet, nutrition and exercise lifestyle changes by monitoring, tracking and adjusting caloric intake, energy expenditure, nutritional information and environmental and behavioral factors. Identifying behavioral issues and working to improve them through prompts and recommendations are used to enhance and maintain positive behavior change. In maintaining the positive behaviors, weight loss and health improvement can be achieved and maintained long term, resulting in significant improvement in quality of life, self esteem, medical conditions and overall health.

In an illustrative implementation (or set of illustrative implementations), the mobile computing device receives food consumption, exercise-related, behavior and other input from various input devices/mechanisms using speech input and digital imaging technology to ease the data entry burden on users and to promote continued long-term usage. In certain illustrative implementations, the system is designed to reward user goal achievement in an automatic, seamless manner, through for example downloading music, books, or other media to the user's mobile computing device via the Internet.

As used herein, it should be understood that any feature identified as being used in one illustrative implementation, is contemplated as being usable in any other illustrative implementation identified herein. Thus, merely because a feature is not expressly identified as being used in a particular illustrative implementation should not be interpreted as an indication that it is not contemplated for use in that implementation. Similarly, any reference herein to "in an implementation/embodiment" or the like should be interpreted as indicating a contemplation of use in any desired implementation. Further, reference to a feature or a set of features being used in "illustrative implementations" should not be construed as an indication that some or all of such features must be used in "all" implementations.

In an illustrative implementation, food consumption and exercise and other goals are set using input from a physician, and/or a nutritionist, and/or healthcare provider, and/or personal trainer, and/or the user, and/or another source. For example, a physician may provide input to set appropriate thresholds for the user including average calorie intake per day, grams of sugar intake per day, amount of exercise per day, etc.

In an illustrative implementation, a "select mode" display is generated. In such an illustrative implementation a wide array of mode select icons are displayed to indicate, for example, a user profile mode for creating a user profile that is modifiable and displayable, a diet selection mode, a food data entry mode, an exercise data entry mode including those using the computing device's GPS functionality, a food purchase mode, a diet and exercise issue mode for addressing a range of issues including user "behavioral" issues in comporting with a diet and exercise program, and various other modes.

One of various mechanisms used by the illustrative implementations to assist, motivate and encourage users to make good, healthy food and exercise choices is a color code system to identify good choices, bad choices and those in between. For example, in an illustrative implementation, the colors GREEN, LIME, YELLOW, ORANGE, and RED, respectively indicate relative values such as Best, Good, Okay, Bad, and Worst with respect to food and exercise choices.

In an illustrative implementation, for each food and exercise activity supported by the system described herein, the system advantageously provides color code feedback to the user with respect to (WRT) any and all of the many nutritional parameters monitored by the system while taking into consideration related health information from a user's profile.

In an illustrative implementation, for each food and each exercise identified by the user, a color code is displayed to the user and dynamically adjusted taking into account, for example, user weight, height, sex, age, health, goals, progress, etc. Such a color code system aids in motivating the user to abide by color codes that are internationally-recognized signals (e.g., "Go" on Green, "Stop" on Red) to select the foods or exercises that provide the greatest benefit (as indicated by the color Green in this example), to avoid the poor choices that provide the least benefit or may even be harmful (as indicated by the color Red in this example), and to advance the color up from Red to Green as soon as possible.

The color coding system used in illustrative implementations is dynamically tailored to individual users in real time. In an illustrative implementation, in generating color code feedback to the user for use in the user's profile generation, the system adjusts the color coding taking into consideration the specific health characteristic to which the user (or the user's physician, nutritionist, or personal trainer) is seeking to improve. For example, in an overweight male user trying to lose weight, fruit is color coded Green but in the overweight female diabetic user who is trying to lose weight and improve her diabetes control, fruit is color coded Orange. Under a variety of circumstances, the same food may undergo a color change for the same user. For example, with the diabetic user, after surpassing a certain amount of fruit in a day, fruit becomes Red due to the sugars in fruit making them not as good for diabetics.

In illustrative implementations with respect to exercise, for a user with significant arthritis in the knees and hips who is trying to lose weight, treadmill walking is coded Red while elliptical machine exercise is coded Orange. However, for such a user, walking or swimming in a pool is coded Green.

In an illustrative implementation, exercise duration times are also factored in by color coding the activity based on the activity itself and the time participating in the activity. In such implementations, too little or too much exercise time generate a less desirable color code, taking into consideration the user's health parameters (heart disease, arthritis, asthma, etc) and the user's goal (to lose/gain weight, improve strength, increase endurance, quit smoking, etc).

In practical effect, the system guides the user to make healthy choices based upon nutrition and health factors tailored to the user, which the user may be unaware of or otherwise avoiding.

In an illustrative implementation, a wide variety of modes may be entered from a "Select Mode" display screen. Initially, a user profile-related mode is entered to permit a user to create, modify, or display his or her user's profile. Entry into such a mode may, for example, enable the user to immediately access his/her current weight loss, calories consumed, calories burned, and other exercise or health-related data to get real-time feedback on his/her progress to date.

In an illustrative implementation, a diet selection mode permits a user to select a diet to be associated with the user's profile that may be used to target one or more medical conditions of the user. In an exemplary implementation, upon the selection of the "diet selection" mode, an array of icons are displayed identifying various diet regimens, at least some of which are targeted to address weight loss, one or more serious medical concerns, and/or other specialized dietary needs such as those of athletes. For example, one or more icons zone in on a diet tailored to addressing the needs of diabetics, cancer patients, gluten-intolerant individuals, individuals with high blood pressure, or individuals with other major medical conditions, who are attempting to stop smoking or drinking, etc. In an illustrative implementation, the application generates selection of a diet by accessing an associated database that contains pre-formulated breakfasts, lunches and dinners targeted to comport with the selected diet and associates such meals with the user's profile.

In an illustrative implementation, one of such icons available in the diet selection mode would, for example, enable selection of the "GOMBS" diet (or a variation thereof) promoted in the mass media by Dr. Joel Fuhrman. In such an implementation, variations of meals following the spirit of the GOMBS diet as identified in Dr. Fuhrman's book "Secrets to Healthy Cooking" are stored in one of the databases used in the illustrative implementation. GOMBS is an acronym for Greens, Onions, Mushrooms, Beans & berries, and Seeds & nuts. Such foods have reportedly been associated with healthier blood vessels/blood flow, enhanced weight loss, reduced suffering from certain cancers, anti-diabetic and other beneficial properties.

In an illustrative implementation, entry into a food consumption data entry mode (Food mode) permits the user to enter into the system, food that is consumed either in or outside a user's home in a manner that is as user-friendly as possible. Over a period of time, users tend to eat one or more of the same favorite meals for breakfast, lunch, or dinner on a consistent basis. Taking advantage of this habituated tendency, the system can learn a great deal about the user's present nutrition profile by initially asking him/her to declare his/her Top 5 favorite meals. In an illustrative implementation where the food is nutritional and low in calories, a user works with, for example, a physician/nutritionist/other consultant to select various breakfast, lunch, and dinner combinations that have beneficial amounts of nutrition (e.g., low in calories, sugars, saturated fats, sodium, etc.) that are then stored in the user's profile (or a database associated therewith). For example, a user who has chosen to eat a breakfast of Cheerios, with raspberries, blueberries, and skim milk may have an associated user profile having such a breakfast identified as "breakfast number 1" and storing (or otherwise identifying by pointing to a database storage location) a wide array of nutritional information for such a breakfast including, for example, calories and sugar content. In such an implementation, using speech recognition software, the system recognizes, for example, the user stating "breakfast number 1" in response to a verbal or displayed prompt to describe the breakfast to be consumed. In certain other illustrative implementations, a touch screen display (or other identification) of a particular food may be used to obtain user confirmation that the speech recognition software accurately decoded the food he/she identified.

After speech recognition software determines, for example, that the user has stated the particular food consumed and the food amount, the system then determines the caloric, nutritional, and other health-related characteristics of the food consumed which is stored and analyzed as described herein. In the above example, a Green color code is displayed to the user consuming such a breakfast number 1. Additionally, in certain illustrative implementations, image processing technology may be utilized to identify the food and the caloric and other nutritional/health-related characteristics of the food consumed. This same user/system interactive process is likewise used for the user to store and later specify other favorite meals such as "Lunch number 3", "Dinner number 5", etc.

In an illustrative implementation, a user's exercise activities are tracked and analyzed. In one of various exercise modes, GPS technology embodied in the user's computing device is used to automatically acquire user coordinate position data using the GPS receiver associated with the mobile computing device, and the system monitors the time over which running, walking, or bicycling exercise activities have occurred. After user entry of the type of exercise being undertaken and after determining the distance traveled during the monitored time, the system generates an estimate of the number of calories burned by the user during such GPS-tracked activity.

In an illustrative embodiment, other exercise modes may be entered in which, for example, speech analysis software is utilized to enable the user to input a specific type of exercise: for example, various exercise-related "tags" are stored in a newly-created exercise record identifying the duration, resistance, rest interval, and other characteristics of the exercise. Under circumstances where various conventional health club exercise machines are used, the system stores the generated output of such exercise machines, such as elliptical machines, stationary bicycle machines, stepper machines, etc., that generate, for example, the number of calories burned during an exercise session.

Further, in other illustrative implementations, a food purchasing mode may be entered to guide the user during food shopping or at a restaurant to determine whether a food product being purchased is consonant with the user's profile and associated goals and health issues. In an illustrative implementation, a database is accessed to identify, where possible, alternative foods of the same food type to enable a user, for example, to select a desired food and yet cut down on, for example, the amount of sugars, fats, sodium, or calories consumed.

Further, in another illustrative example, a diet/exercise issue mode may be entered where the user selects a category corresponding with a behavioral issue that may be impacting diet or exercise success. The user is then prompted to answer questions regarding the behavioral issue raised by the user's problem. The responses are analyzed by the system and the system provides the user with recommendations to improve the behavior: e.g., to eat an apple at 3 PM in response to a user query regarding hunger issues in the middle of the afternoon.

Additionally, in illustrative implementations access to external servers and databases is advantageously utilized to provide a behavior enhancing reward system designed to motivate users to achieve their goals through rewards based on goal achievement and/or progress towards goal achievement. In an illustrative implementation, any diet, exercise, health or nutritional goal being met may trigger an award generation, including weight-related goals, exercise-related goals and smoking cessation-related goals. A reward may be embodied in a wide variety of forms including, without limitation, automatically downloaded music, movies, digital versions of TV shows, music videos, cash, discounts at movies, restaurants (particularly those that include a wide range of healthy alternatives), discounts at sporting events, mobile games, mobile gaming currency, other mobile applications, etc. In an illustrative implementation, a user's types of reward preferences, e.g., music, electronic book, etc., are stored in the user's profile to guide the system in generating and downloading an appropriate reward.

These and other features of the illustrative implementations will become apparent from a review of the drawings of which:

BRIEF DESCRIPTION OF THE DRAWINGS

FIG. 2B1 illustrates various nutrition and exercise-related modes of operation of the mobile computing device when performing the weight, exercise and nutrition tracking methodology described herein;

FIG. 2B2 is an illustrative diet selection screen that is generated when a diet selection mode icon 52 is selected by a user;

FIG. 2C illustrates a color-code rating scale, with exemplary thresholds, for each food eaten, each nutrient consumed, each exercise performed, and relative level of goal achievement by the user;

FIG. 2D1 illustrates macronutrients considered essential to the human body, plus an identifying color code level for each macronutrient;

FIG. 2D2 illustrates micronutrients considered essential to the human body, plus an identifying color code level for each micronutrient;

FIG. 2E provides an example of how color code ratings from Red to Green can be derived for any given nutrient, such as vitamin C, from a 100% baseline established using certain widely-available foods for that nutrient;

FIG. 2F illustrates a top nutritional foods database identifying various top natural foods and a variety of their best peers within the same food family;

FIGS. 2G1 and 2G2 are an illustration of a recommended daily intake (RDI) database that discriminates the calorie needs of various users based on, e.g., their body weight, gender, age, and level of physical activity;

FIG. 3C shows an exemplary data matrix for the food database in FIG. 3B that enables a user to declare his/her Top 5 favorite meals for breakfast, lunch, and dinner, as well as snacks and drinks, displaying popular food items/add-ons for each matrix cell to encourage user participation in every meal category;

FIG. 3F shows an exemplary matrix for the exercise database in FIG. 3E that enables a user to declare his/her Top 5 favorite exercises for sports, conditioning, and weightlifting, as well as daily and periodic tasks, displaying popular exercises/tags for each matrix cell to encourage user participation in every category;

FIGS. 4B1 and 4B2 illustrate macro- and micro-nutrients in the USDA Nutrient Database;

FIG. 4C shows a comparison of 2 examples of popular Fast Food items (Red level 1) side-by-side with 2 examples of healthy Salmon/Turkey (Green level 5), where all nutrient data was extracted from the USDA Nutrient DB of FIGS. 4B1 and 4B2;

FIGS. 5B1 and 5B2 show numerous examples of calories burned via activities/exercises, excerpted from the Compendium of Physical Activities (researched/updated for NIH by Arizona State Univ 2012) which, taken together with an illustrative calorie coefficient, form an illustrative system Activity Database;

FIG. 6C is an illustrative risk chart depicting the health risks from being overweight and/or obese.

FIG. 7A1 illustrates a database format specifying a record format to track user weight loss (gain) across time toward multiple delta subgoals, leading to an overall final goal;

FIGS. 7A2-7A4 provide 3 illustrative examples that use FIG. 7A1 delta subgoals to track weight loss from obese to overweight, from overweight to healthy weight, and from healthy to ideal weight;

FIGS. 7B1 and 7B2 show illustrative DB register formats for each user food eaten and exercise done (for the Food DB in FIG. 4A and the Exercise DB in FIG. 5A, respectively);

FIGS. 7B3 and 7B4 show companion DB register formats for user Daily and Delta Records, which accumulate Cals In/Cals Out to calculate weight loss (gain) on a daily and cumulative basis, respectively, to show user food, exercise, and weight loss (gain) history from start to current date;

FIGS. 8A-8C show an illustrative user profile record format that may be used in an exemplary implementation; FIG. 8A delineates an illustrative user ID and user Health Data List that includes all related data items declared in the User Profile flowchart of FIG. 3A;

FIG. 8B shows an illustrative variable-length record format for all Nutrition data items declared in FIG. 3A, repeated cyclically for each Food/Add-on eaten/declared by the user in FIG. 4A;

FIG. 8C shows a variable-length record format for all Exercise data items declared in FIG. 3D, repeated cyclically for each Exercise/Set performed/declared by the user in FIG. 5A;

FIGS. 12A-12B show tables correlating body frame (small, medium, large) of a man or woman with either a user's wrist size or his/her elbow size, respectively;

FIG. 13B shows how the Met Life profiles of FIG. 13A can be rotated around a common pivot point with the USDA Chart to yield a more realistic healthy-weight model for all men and women;

FIG. 13C1 illustrates an ideal weight database that allows the system to provide an ideal weight matched to a user's height for both men (left side) and women (right side);

FIG. 13C2 is a chart showing the step-wise linear MIN/MAX boundary equations used to define the limits of ideal weight for men and women, as tabulated in FIG. 13C1 and charted in FIG. 13B.

DETAILED DESCRIPTION

Figure 1:
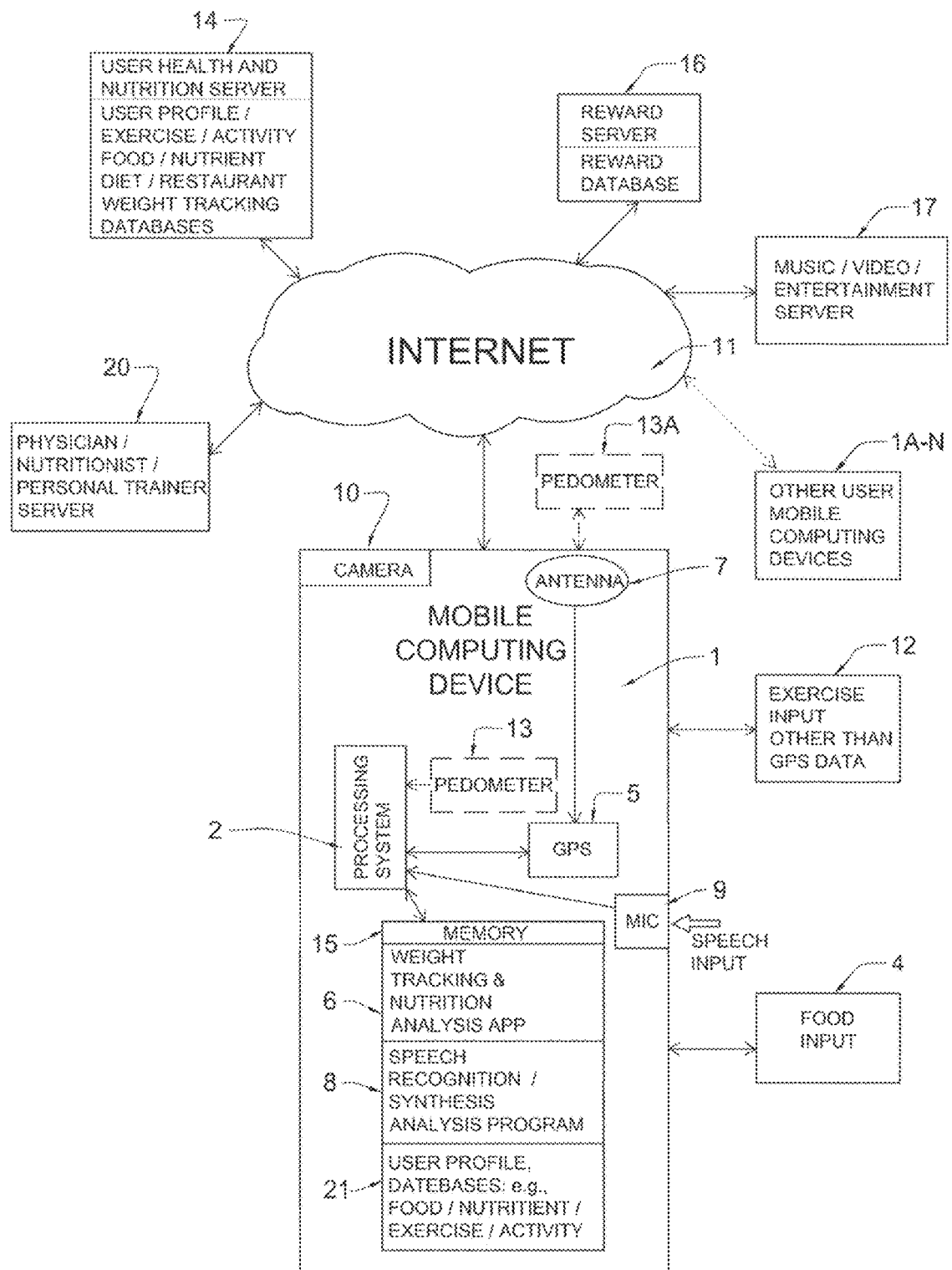
FIG. 1 is a block diagram of a non-limiting, illustrative mobile computing weight, exercise, nutrition tracking and reward system.

FIG. 1 is a block diagram of a non-limiting, illustrative mobile computing weight, food consumption, nutrition, and exercise tracking system with enhanced data entry and user feedback. As schematically illustrated in FIG. 1, a mobile computing device 1 receives food consumption and exercise input from a potentially wide range of input devices/mechanisms 4, using, for example, a microphone 9 for speech input and a digital imaging device (such as camera 10) associated with the mobile computing device 1. The mobile computing device 1 additionally receives user exercise-related input using an internal GPS receiver 5 and from various exercise equipment 12 not involving GPS data as explained further below.

As will be explained further below, mobile computing device 1 communicates via the Internet with a server 14 that includes associated user profile, weight tracking, exercise/activity databases, and food/nutrition databases as described in more detail below.

Additionally, mobile computing device 1 also communicates via Internet 11 with a rewards server 16 that includes an associated rewards database that in turn communicates with a music, video and entertainment server 17 that is utilized during reward processing to provide additional motivation to users for enhancing the likelihood of goal achievement. It should be understood that, while servers 14 and 16 and physician/nutritionist/personal trainer/data processing system/server 20 are represented by multiple computers having multiple associated databases, such systems may be implemented, if desired, at one data processing system location using one data processing system having one database.

Mobile computing device 1, in an illustrative implementation, may be implemented by any of a wide array of commercially available, conventional mobile computing devices, including, for example, conventional smart phones, such as Apple's iPhone 4s or 5, or Samsung's quad-core processor-based Galaxy S3, a tablet computing device such as Apple's iPad, or any of a number of laptop computers. In certain illustrative implementations, such mobile computing devices may be modified to include a pedometer 13 that provides user step-related data to the mobile computing device's processing system 2. See, for example, the commercially available Ipod Nano with a built in pedometer. In other implementations, a pedometer 13A wirelessly transmits pedometer data to mobile computing device 1 that is received by a receiver in mobile computing device 1 in a manner understood by those skilled in the art. See, for example, the commercially available pedometer used with an Ipod or Iphone that receives pedometer transmissions from a shoe. Although in illustrative implementations, step-related data may be transmitted wirelessly to mobile computing device 1 for use in exercise tracking in walking or running activities, exercise-tracking during such activities may be made based on GPS data analysis alone, as will be explained further below.

Mobile computing device 1, as will be appreciated by those skilled in the art, includes a processing system 2 that is operatively coupled to receive speech input from microphone 9, GPS data from GPS receiver 5, and image data from camera 10. Processing system 2, inter alia, executes the unique weight, diet, food/nutrition, exercise/activity, behavior, health-related tracking, analysis, and user feedback application software 6 stored in the mobile computing device's memory subsystem 15. Memory 15 may, for example, be implemented by a 64 GB memory, such as that associated with the iPhone 4S or iPhone 5. Although not shown in FIG. 1, it is contemplated that, if desired, the user's mobile computing device may be coupled to a user's desk top computer to store and further analyze any and/or all the information identified herein.

The computing device 1 also includes one or more cameras 10 that, as will be explained further below, may be advantageously utilized as a food consumption and, if desired in certain instances, an exercise-related input device. The illustrative digital camera 10 that may, for example, be the digital camera in a conventional iPhone 4S or iPhone 5, incorporates a conventional optical system including an imaging device having a CCD/CMOS image sensor. For example, the CCD image sensor captures an optical image of a target and the imaging device outputs a converted image signal. As will be understood by those skilled in the art, image processing circuitry including an analog to digital converting circuit converts processed image data into a digital image signal. Such a digital image signal is transferred to processing system 2.

Memory 15, in an illustrative implementation, stores a wide range of user-related data 21 including a User Profile, and various user databases including for example, a food database, a nutrient database, an exercise database, and an activity database, each of which is described in detail herein. As described below, an illustrative user profile record format is shown in FIG. 8A. An illustrative user profile, includes the user's ID, sex, age, height, weight, wrist size, waist size, a set of goals, potential reward information, etc. Additionally, an illustrative user profile includes a range of health data including information regarding handicaps, ailments, injuries, smoking, addictions, allergies, and food and exercise restrictions. FIGS. 8B and 8C described below illustrate a user's food record format and exercise record format that also may be part of the user's profile or, alternatively, may be stored locally as databases on the user's mobile computing device, e.g., an Iphone, as indicated in FIG. 1.

The mobile computing device 1, in an illustrative implementation, also includes associated speech recognition, analysis, and synthesis software 8 stored in memory 15 that is utilized as is described below to provide data entry for food consumption, and certain exercise and behavior. A person skilled in the art will recognize that commercial speech recognition, analysis and synthesis software systems are well known and are commercially available, such as Dragon Naturally Speaking offered by ScanSoft and Via Voice marketed by IBM. Further, the speech recognition, analysis and synthesis software (hereinafter referred to as speech recognition) 8 may be implemented by a system corresponding to Apple's Siri intelligent personal assistant and navigator system utilized in the iPhone 4S or iPhone 5 augmented to incorporate the speech recognition, voice synthesis/communication and control features described herein. The speech recognition software 8 is executed by processing system 2. The speech recognition software includes a voice recognition module that is responsible for parsing input speech as digitized by an audio codec and analog to digital converter operatively coupled to processing system 2. Well known speech recognition algorithms are well understood to those skilled in the art and are available for inclusion included in such speech recognition software 8, such as, for example, the voice recognition methodology described in U.S. Pat. No. 7,809,565, which is incorporated herein by reference. In an illustrative implementation, as will be explained further below, speech recognition operations are simplified due to user prompts that condition the system to expect receipt of a certain type of information from the user to trigger the storage of, for example, food consumption-related data.

Mobile computing device 1 includes a GPS receiver 5 that is capable of determining the geographic location of computing device 1 via received satellite signals from antenna 7 in a manner well understood by those skilled in the art. The GPS receiver 5 in an illustrative implementation is operable to output to processing system 2 the geographical coordinates of mobile computing device 1 to define its current location in real time. The geographical coordinate location data may be stored in conjunction with time-related data under the control of processing system 2 for use in calories burned-related calculations. As noted above, in illustrative implementations, in addition to wirelessly receiving GPS data, mobile computing device 1 may wirelessly receive step-related data from a pedometer-based device 13A including a transmitter that transmits step-related data that is received via, for example, the mobile computing devices' antenna 7 and processed as described herein in a manner appreciated by those skilled in the art.

It should be recognized that in yet other illustrative implementations, a vast number of additional mobile computing devices 1A-N (where A to N—used herein as any desired integer—may range from 1 to any desired number of devices N) may also be utilizing servers 14, 16, 17 and 20 for the same weight, diet, and nutrition tracking and analysis as described in detail herein. In illustrative implementations, weight loss competition between users may occur. Moreover, teams of users may be formed to compete against each other based on a variety of criteria such as total weight loss by team members, successful weight loss by highest percentage of team members, total calories burned during exercise by team members, etc. In such an implementation, server 14 is programmed to compile the results for each team, assess such results, and declare a victor in the competition. Team members are rewarded in a manner corresponding to the description below of the reward generation process when an individual user meets individual goals.

In an illustrative embodiment, the mobile computing device 1 communicates via the Internet 11 with one or more physicians and/or nutritionists and/or personal trainers located at one or more remotely located data processing stations 20 exemplified in FIG. 1 as a physician/nutritionist/personal trainer server 20. In illustrative implementations, goals to be attained by users are set based upon a generated user profile using health and exercise information obtained from the user and/or using physician, nutritionist, personal trainer-generated thresholds for the user including average calorie intake per day, grams of sugar intake per day, amount of exercise per day, etc. In one illustrative implementation, it is contemplated that the user input all requested health and exercise information into the system without assistance from a physician, nutritionist, trainer or other source. In such an implementation, a user, for example, may determine requested variables by his/her own research by communicating with a doctor, healthcare professional and others, and then enter such information. In this implementation, the user need not rely on any other source for inputting information.

In certain illustrative embodiments, server 20 may be distributed and implemented by, for example, individual physicians who already have a doctor-patient relationship with the user of mobile device 1. Such physicians commonly have an extensive medical history stored for patients. Various implementations, particularly those that involve large numbers of users may employ artificial intelligence-based software that automatically responds to medical queries and sends warning messages if maximum or minimum thresholds are exceeded or are not met triggered by, for example, a user consuming too much sugar, too many calories, not completing enough exercise, etc. As will be appreciated by those skilled in the art, the number of servers 20 employed will need to be tailored to the volume of inquiries. In other implementations, particularly those having a modest volume of queries, it is contemplated that a physician, nurse, physician's assistant, nutritionist, personal trainer, or other professional individually responds to queries and personally manages the user's food consumption and exercise programs.

Figure 2A:
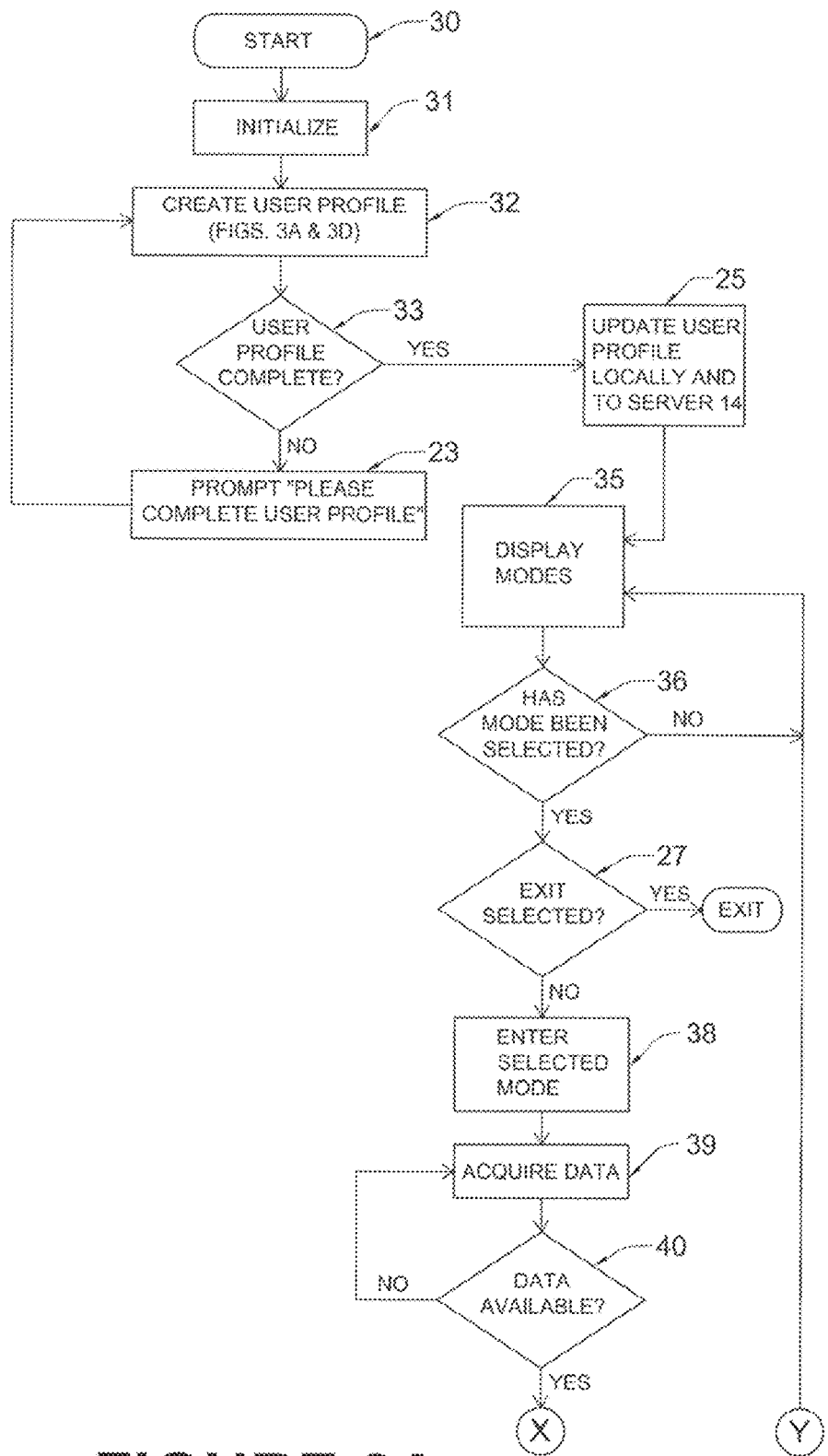
FIG. 2A is a flowchart delineating the general sequence of operations performed by the mobile computing device during performance of illustrative weight tracking, analysis, and user feedback methodology.

FIG. 2A is a flowchart delineating the general sequence of operations performed by a mobile computing device 1 during execution of the weight, diet, food, nutrition, exercise, activity, behavior, health-related tracking, analysis, and user feedback application software 6 identified above in conjunction with FIG. 1. Upon a user selecting application 6 for execution (30), initialization operations are performed (31). In an illustrative implementation, when the weight tracking and nutrition analysis application initially begins executing, a display is generated identifying feature highlights of the weight tracking, exercise tracking, nutrition analysis and the reward/motivational aspects of the system and methodology described herein that promote, for example, weight control, better nutrition and a healthier lifestyle. In an illustrative embodiment, a user is prompted to indicate the user's agreement to initiating weight, medical and exercise tracking operations. In an illustrative implementation, a user may be required to acknowledge and accept certain responsibilities in using this device relating to, for example, diet regimens and exercise routines recommended by the system. In such an implementation, the user is requested to read an associated disclaimer and then select an affirmative response to acknowledge acceptance of responsibility by the user for the device to begin operation. Initialization processing in an illustrative implementation involves user authentication and appropriate configuration of files to be used by application 6. Upon initial entry into the application, the system resets registers storing, for example, variables to track to a zero state. A check may be made to ensure that the application has been appropriately downloaded. If, for example, the user turned off a smart phone or other mobile computing device 1 to pause during exercising, in initialization processing, the system restores the prior processing and file states to comport with the point where the exercising (or other processing) paused.

After initialization operations, if not previously created, a user profile is generated during create user profile processing (32) as is described in detail herein in conjunction with the description of FIGS. 3A-3F. In an illustrative implementation, user prompts are generated to request desired data including user height, weight, medical conditions, including, but not limited to diabetes, heart disease, handicaps, allergies, etc. In illustrative implementations, during this process, smokers and users who are attempting to quit smoking are also identified. In an illustrative implementation, data is supplied by users via speech input and/or by a graphics display/touch screen that may be provided in parallel with speech inputs to aid in the recognition process. Such user data is supplemented, if authorized by the user, with detailed relevant blood work and goal-related information transmitted via the Internet 11 from a physician/nutritionist/personal trainer's data processing center 20. The user profile in an illustrative embodiment stores goals including weight loss, exercise, smoking cessation, and other goals. In illustrative implementations, goals are dynamically changed over time. For example, smoking cessation goals may begin at not smoking for one day and be modified to more long term goals as smoking cessation goals are continuously met. As will be explained in detail herein, during subsequent processing, after a user profile has been created, the system modifies the user profile in real time based on current information stored locally and/or in the database associated with server 14 during mode processing. After the user profile has been created, it is accessed from server 14, if it is not already stored locally within the mobile computing device 1.

After a user profile data entry operation has been completed (32), a check is made to determine whether the user profile is complete (33). If not, the user is prompted to "please complete profile" (23) by entering further data in the user profile as indicated at block 32. The user's continued efforts in completing the profile provide an opportunity for the user to correct any data entry errors by modifying any previously entered data. In an illustrative implementation, the user is given a limited number of attempts to complete the user profile to provide some predetermined minimum level of completion. Once this limited number of attempts has been reached, if no data is entered by the user, the weight tracking and nutrition analysis routine is exited. While it is desired to limit the number of user data entries to the bare minimum, in illustrative implementations, it is likewise desirable to require a sufficient amount of information about the user to assist the user in gaining life changing, long-term health benefits from the system described herein.

If the check at block 33 indicates that the user profile is complete, then the user profile is stored locally in the user phone DB (storage 15) and also uploaded to remote server 14 (25).

Thereafter, mobile computing device 1 generates a "select mode" display (35) as illustrated in FIG. 2B to display various operational modes that a user may initiate as will be explained in detail below.

A check is then made to determine the mode of operation to enter based on a user's selection of the modes displayed on the display of the user's mobile computing device 1 (36), as explained in further detail in conjunction with FIG. 2B. A check is then made at block 27 to determine whether the select mode display has been exited (27). If so, the select mode screen is closed.

If the user has not selected the exit icon in FIG. 2B, then based on the user's selection of one of the operational modes, the system enters the selected mode (38). In an illustrative implementation, the system sequences through checks for each of the displayed modes to determine if the user has selected a mode. If no mode is selected, the routine continuously cycles back to check the various modes being displayed until the user finally selects a mode.

If, for example, the food mode has been selected, the system acquires the user's desired food consumption data (39), as will be explained further below. A check is then made at block 40 to determine whether data is available. If data is not available, the routine continues to check for data. Such data checking continues until a predetermined time period passes (e.g., a number of minutes of no data entry), at which point the routine branches back to display mode block 35.

If data is available, the system acquires the appropriate data for the mode being processed, and the detailed processing associated with the selected mode is performed (42) as shown in the continuation of FIG. 2A.

After a mode processing operation (42) has been completed, a check is made at block 43 to determine whether the mode of operation in process has ended. If the mode being processed is not yet finished, the routine branches back to block 42 to complete mode processing. If the mode has finished, then a check is made at block 44 to determine whether the user has decided to cancel the current mode being processed or to change to a different mode (44). If the user has decided to cancel or change the mode, the routine branches back to display mode block 35.

If the user has not canceled or changed the mode as indicated by the check at block 44, the databases associated with the user are updated (46) to reflect in real time the current status of, for example, the user's food consumed or exercise performed.

A check is then made as indicated at block 47 to determine whether a reward has been earned based on, for example, the updated data generated during mode processing that was stored at block 46. If no reward has been earned, the routine branches back to display modes block 35.

If the check at block 47 indicates that a reward has been earned, the system performs reward processing operations to determine if goals have been met and, if so, provides, as desired, a reward to the user for meeting daily, weekly, or monthly goals (48). By way of example, based upon a user's indicated preference for a music-based reward, the reward processing system (44) may utilize Apple's iTunes application. The iTunes' app automatically selects music to download to the user based upon: [1] the contents of the user's iTunes' playlist; [2] the music listened to by the user during exercise; or [3] a stored playlist created by the mobile computing system 1 over time. Thereafter, the routine branches back to display modes block 35.

As shown in FIG. 2B1, in one illustrative implementation of the mobile tracking system and methodology described herein, a "Select mode" display is generated in which an array of select mode icons are displayed. The user may enter any mode he or she chooses, starting with the User Profile mode 50 where, upon system startup, the user can extensively personalize the system by declaring his/her favorite foods and exercises (explained in detail with FIGS. 3A-F). The dotted lines between displayed icons indicate that additional other mode initiating icons (such as Diet/Exercise Issues mode 54) may be added to the icons shown in FIG. 2B1 to provide ease of user entry into additional operations disclosed or suggested herein or contemplated in other implementations. In the example shown in FIG. 2B1, an illustrative "Nth" mode (where N is any desired integer N representing the last desired mode in a particular implementation) is exemplified as a Vitamins mode 60 to provide ease of user entry of the user's preferred/favorite vitamins and food supplements (e.g., *ginkgo biloba*).

As also shown in FIG. 2B1, in an illustrative implementation, the icons are conveniently arranged in a layout corresponding to the user's expected most frequent accesses to the system. For example, in this illustrative implementation, the top level is reserved for the most often accessed icons: displaying/modifying the User Profile 50 (FIGS. 3A-3F), entering food eaten throughout the day via Food mode 56 (FIG. 4A), and entering exercise performed throughout the week via Exercise mode 62 (FIG. 5A). The middle level is reserved for functions accessed by the user on an as-needed basis: a Diet Selection mode 52 (FIG. 2B2), any Food Purchases 58 (FIG. 6A), and any GPS-based Exercise 64 (FIG. 5A). The bottom level includes a Diet/Exercise Issues mode 52 (FIG. 6B) for obtaining personalized tips for addressing a user's diet/exercise personal behavioral issues, and a Vitamins mode 60 (as an example of the Nth mode) for user entry of vitamins/minerals taken and personalized information/recommendations regarding vitamin supplements. At any time, the user may choose to exit the mobile system via Exit icon 66.

As shown in FIG. 2B1 and as explained in detail in conjunction with FIGS. 3A-F, the User Profile mode 50 may be entered at any time to permit a user to create, modify, or display his/her User Profile. Entry into such a mode may, for example, enable the user to immediately access his/her current weight loss, calories consumed, calories burned, and other exercise, nutrition, or health-related data to get real-time feedback on his/her progress to date.

Detailed Discussion of Diet Selection Mode 52 (FIG. 2B2):

In an illustrative implementation, a Diet Selection mode 52 permits a user to select a diet to be associated with the user's profile that may, for example, be used to target one or more medical conditions of the user. As used herein, the term "diet" is used broadly to refer to an organized plan for specifying or limiting what one eats and drinks. The plan does not necessarily have to have weight loss as its goal.

In an exemplary implementation, upon the selection of the "diet selection" mode, an array of icons are displayed identifying various diet regimens, at least some of which are targeted to address one or more serious medical concerns or specialized needs. For example, one or more icons zone in on a diet tailored to addressing the needs of diabetics, cancer patients, individuals who are attempting to quit smoking, gluten intolerant individuals, and users having high blood pressure, other major medical conditions or specialized needs such as those of athletes. Upon the selection of such a diet, the application generates and/or accesses pre-formulated breakfasts, lunches and dinners that are targeted to comport, where possible, with a user's indicated favorites, and with the selected diet and associates such meals with the user's profile.

In an illustrative implementation, one of such icons available in the diet selection mode would, for example, enable selection of the "GOMBS"-related diet promoted on various mass media by Dr. Joel Fuhrman. In such an implementation, variations of meals following the spirit of the GOMBS-related diet as identified in Dr. Fuhrman's book "Secrets to Healthy Cooking" are stored in a database used in the illustrative implementation.

GOMBS is an acronym for Greens, Onions, Mushrooms, Beans and berries, and Seeds and nuts. Such foods have reportedly been associated with healthier blood vessels/blood flow, reduction in the likelihood of suffering from certain cancers, enhanced weight loss, anti-diabetic and other beneficial properties. It has been reported that green leafy vegetables have many diverse nutrients and properties that help the body to allow blood vessels to function better. Onion consumption has been associated with reduction in certain cancers in at least one European study. Mushroom consumption has been associated with a decreased likelihood to develop breast cancer in certain studies. Beans and berries have been reported to have high cancer preventive antioxidants levels while promoting healthy brain function. Beans and legumes have been reported as containing soluble fiber and as having anti-diabetic and weight-loss properties. Blueberries, strawberries and blackberries are low in sugar and very high in nutrients. The antioxidants in berries have been reported as providing both heart-protective and anti-cancer effects. Raw seeds and nuts have been reported as helping to reduce the body's inflammation and to reduce cholesterol.

In accordance with an illustrative implementation, if the user selects the GOMBS diet (on his or her own or after being prompted to consider this diet due to a user's profile indicated health condition), the application generates and/or accesses pre-formulated breakfasts, lunches and dinners that feature these health benefitting ingredients and that comport, where possible with the user's favorite foods and with the GOMBS-related diet and associates such meals with the user's profile using a variation of the format shown in FIG. 8B.

Figure 2A:
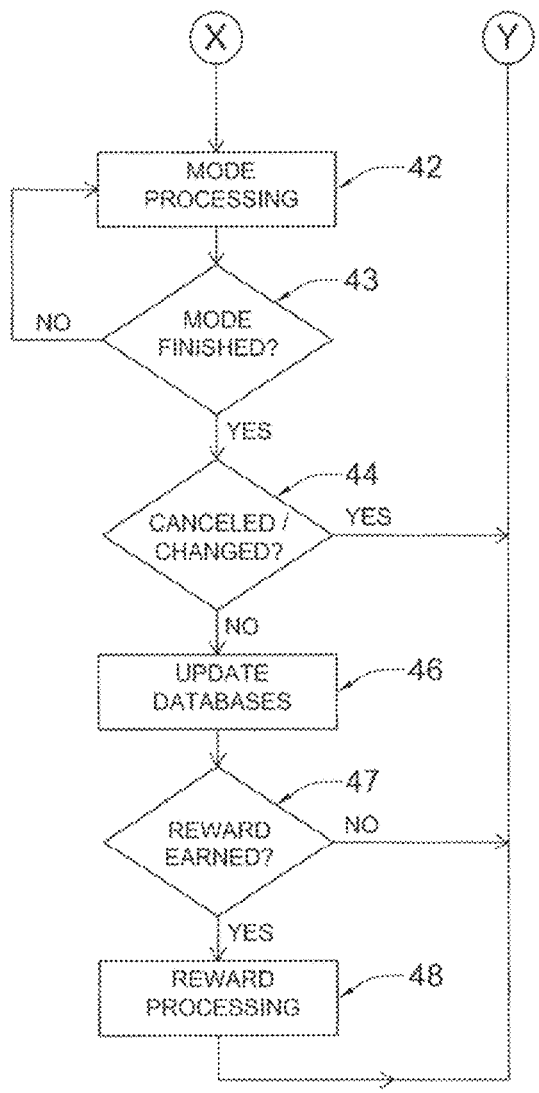

Turning to an illustrative example of the diet selection mode, the user's selection of diet selection mode icon 52 shown in FIG. 2B1 triggers the generation of a display of an array of diet-related icons, such as is shown in FIG. 2B2. In an illustrative implementation, it is contemplated that the user will have the opportunity to select a totally customized diet plan or any one of a variety of popular diet plans such as, by way of example only, the Atkins diet (100) and the South Beach diet (101). The selection of icon 100 or 101 will respectively result in the generation of a presentation of the details of the Atkins and South Beach diet plans including a list of foods that comport with each plan.

In addition, in an illustrative implementation, an array of icons are generated that have been recognized as being helpful in addressing various medical conditions including those identified by users in their user profiles. The use of specific dietary regimens to enhance the treatment and control of medical conditions is often an important component of an overall treatment plan for the specific condition. As such, specialized dietary regimens can be utilized as part of the overall treatment of that medical condition in an individual whose goal is to keep their weight stable. Additionally, these specialized dietary regimens can be used as part of a weight loss intervention for an individual suffering from certain medical conditions. In this setting, a calorically restricted regimen having specific beneficial components relative to the medical condition would be utilized.

In an individual suffering from more than one medical condition, a customized dietary regimen utilizing and incorporating specific beneficial components of a number of specialized regimens would be utilized addressing special dietary needs in a way that enhances the treatment of all of the medical conditions. An example might be use of a specialized dietary regimen having beneficial components to improve diabetes and hypertension concurrently.

Another situation to consider is the individual suffering from a medical condition such as cancer or gastrointestinal absorption problems resulting in excessive weight loss and difficulty maintaining weight. There are specialized dietary regimens that can be utilized to improve this situation. In an illustrative implementation, one or more of such regimens would be identified and highlighted to such an individual and would be included in the array of icons dedicated to therapeutic diet plans (98).

There are also other circumstances in which individuals may benefit from specific dietary regimens not related to weight loss and not related to a medical condition. Examples include athletes in a specific training regimen such as endurance running or weight training. In an illustrative implementation, one or more of such regimens would be identified and highlighted to such an individual and would be included in the array of icons shown in FIG. 2B2.

It is possible to contemplate even more permutations of special dietary needs in individuals that may have certain medical conditions, are stable and otherwise healthy and are pursuing various athletic endeavors. An example might be a young type I diabetic who is a long distance runner. This individual would benefit from some aspects of a diabetic diet but would have vastly different nutritional needs compared to a sedentary type I diabetic. In an illustrative implementation, an acceptable regimen would be identified and highlighted to such an individual and would be included in the array of icons dedicated to therapeutic diet plans (98).

In an illustrative implementation, when the diet selection mode icon 52 is selected, a display is generated identifying an array of icons each defining a diet regimen that may be selected by a user. For example, as shown in FIG. 2B2 when the diet selection mode icon 52 is selected a diet selection screen is generated. As indicated above, the diet selection screen includes an array of possible diets that may be selected by user to review foods that may be eaten in conformance with a diet.

As shown in FIG. 2B2, in this example, with respect to medical condition-related diets, a user will be enabled to select a diabetic diet 91, a hypertension diet 92, a renal diet 93, the GOMBS diet (102) described above, a cardiac diet 94, a gluten-free diet 95, a food allergy diet(s) 96, athletic/muscle building diets 97, and any of an array of other therapeutic diets 98, at any time the user may exit from the diet selection screen by touching the exit icon 99.

In illustrative implementation, when a user identifies in his or her user profile a health condition which implicates one or more of the identified diets, upon selecting the diet selection screen one or more of the diets shown in FIG. 2B2 is highlighted for the user. For example, for a user who indicates in his or her user profile, a diabetic or blood sugar-related problem, diabetic diet 91 will be highlighted for the user to peruse.

In such an implementation, each of the medical condition/health condition-related diets is indexed in the system in a memory table used to access one or more diet plans. The memory table is structured to associate a set of medical or health conditions with one or more diet plans. For example, key terms such as "diabetes," "blood sugar," "diabetic," etc., are linked in the memory table used to access one or more diet plans to a diabetic diet. Similarly, key terms such as "hypertension," "high blood pressure," etc., are linked in such a table to a hypertension diet. Key terms such as "cardiac," "heart," etc. are linked in this table to a cardiac diet plan. Likewise, terms such as "gluten," or "allergy" are respectively linked in the table to a gluten-free diet or a food allergy diet. Further, in an illustrative implementation, the user is prompted to review the diet highlighted on the diet selection screen or otherwise notified of appropriate diets, if the user has identified (e.g., during the creation of his or her user's profile) a condition suggesting the efficacy of such a diet in addressing the symptoms or causes of the user's condition.

The following are some examples of special dietary regimens including those identified above that would be beneficial in the treatment and context of certain medical conditions and certain athletic situations and that would be selected by the system for consideration by the user based upon the user's profile implicating one or more of the following diets:

1) Diabetic diet—goal is to alter diet in a manner that improves control of serum glucose. This regimen typically decreases sugary carbohydrates and saturated fats while increasing fiber and protein. Also, timing of food intake is important in a diabetic dietary regimen. A calorie restricted version of this diet would be utilized in diabetic individuals needing to lose weight.

2) Hypertension diet—goal is to alter diet in a manner shown to improve blood pressure control. The DASH diet (Dietary Approach to Stop Hypertension) is an accepted example of such a regimen. This regimen typically promotes use of more fruits, vegetables, low fat dairy, grains, fish and poultry and foods rich in magnesium, potassium and calcium while discouraging saturated fats, red meat, sugary carbohydrates and salt. A calorie restricted version of this diet would be utilized in hypertensive individuals needing to lose weight 3) Renal diet—goal is to alter diet in a manner shown to minimize complications associated with existing or developing renal dysfunction. Those individuals having compromised renal function and those to the point requiring dialysis must limit intake of sodium, potassium and phosphorous while delicately balancing fluid intake and output and maintaining appropriate levels of electrolytes while also taking in an appropriate amount of protein to maintain lean body mass but not negatively impact remaining renal function. A calorie restricted version of this diet would be utilized in individuals having renal function impairment needing to lose weight 4) Cardiac diet—goal is to alter diet in a manner to minimize risk of cardiac illness and promote cardiac function in the context of existing cardiac disease. This regimen discourages foods with high amounts of cholesterol and saturated fats while promoting low fat protein, vegetables, fruits and unsaturated fats. A calorie restricted version of this diet would be utilized in individuals having cardiac disease needing to lose weight 5) Gluten free diet—goal is to eliminate or minimize foods containing gluten. Individuals suffering from celiac disease cannot process gluten containing foods. These foods, including most cereals, breads and pastas must be eliminated and replaced with fruits, vegetables, unprocessed meats, dairy and non gluten containing grains such as rice. A calorie restricted version of this diet would be utilized in individuals with celiac disease needing to lose weight 6) Therapeutic diets—there are numerous additional conditions that would benefit from customized, specialty dietary regimens that would help diminish the negative affects of the condition. An example here would be food allergies. Some individuals suffer from allergies to certain foods which can vary in number from few to many. Specialized dietary regimens are often required to help minimize the food allergy symptoms. A calorie restricted version of this diet would be utilized in individuals requiring the use of therapeutic diets needing to lose weight 7) Athletic diets—nutritional requirements of athletic vary significantly based on the type, duration and goal of the athletic activity. For example, individuals in weight training building large amounts of muscle need greatly increased amounts of protein daily while the dietary regimen of endurance runners would need to include more carbohydrates and some fats.

Detailed Discussion of Remaining Select Modes in FIG. 2B1

Entry into the Food mode 56 permits the user to enter into the system food that is consumed in a manner that is as user-friendly as possible. Over a period of time, users tend to eat one or more of the same favorite meals for breakfast, lunch, or dinner on a consistent basis. Taking advantage of this habituated tendency, the system can learn a great deal about the user's present nutrition profile by initially asking him/her to declare his/her Top 5 favorite meals. In an illustrative implementation, a user working, for example, with a physician, nutritionist, or other consultant selects various breakfast, lunch, and dinner combinations where the food is nutritional (e.g., low in calories, sugars, saturated fats, sodium, etc.) that will be stored either directly in or linked to the User Profile. Such preselected meals may be stored in the User Profile as schematically represented in FIG. 8B. For example, a user who has chosen to eat a daily breakfast of Cheerios, with raspberries, blueberries, and skim milk may, in an illustrative implementation have stored in his user profile, a corresponding breakfast identified as "breakfast number 1" together with a wide array of nutritional information for such a breakfast including, for example, calories and sugar content. A wide array of similar user profile meal entries may be made for lunch and dinner. In an illustrative implementation, the food mode incorporates extensive use of color codes to inform the user as to a wide range of health and nutritional information about the food being consumed and alternative choice options.

Using speech recognition software 8 shown in FIG. 1, the system recognizes, for example, the user stating "breakfast number 1" in response to a verbal and/or displayed prompt to describe breakfast information. The speech decoding process is simplified by using such user prompts since the system may expect to receive a verbal indication of, for example, a known category of foods, e.g., breakfast foods or a prestored breakfast combination (e.g., "breakfast number 1"). This same user/system interactive process is likewise used for the user to store and later specify other favorite meals such as "Lunch number 3", "Dinner number 5", etc. Alternatively, where no prestored meals have been selected, in an illustrative implementation, the system prompts users to state, for example, the breakfast food consumed and the food amount. The system then determines the caloric, nutritional, and other health-related characteristics of the food consumed which will be stored and analyzed by the system and displays relevant color codes to the user.

In an illustrative implementation, in conjunction with creating a user profile, if a user indicates a particular favorite food such as a snack, e.g., chocolate ice cream, the system will display its associated color code, e.g., Orange or Red, indicating a poor choice by the user. The system will thereafter display alternative snack choices have better color code ratings—e.g., yogurt (color Green), an apple (color Lime) or almonds, walnuts and flax seeds (color Green)—all in an attempt to prompt the user to select a healthier favorite.

In an illustrative implementation, the system accesses a wide range of accessible nutritional information from existing sources through Internet resources. For example, food/nutrition lists having information regarding calories, fats, carbs, etc. are available though such sources as CDC or NIH (e.g., see FIGS. 4B1-4B2) or weight watchers or similar organizations (with permission to obtain such lists). With such available nutritional information accessed through its databases, the system can calculate the wide range of calorie and nutrition values referenced herein. Similarly, various exercise lists with associated calories burned information have also been developed/refined across many years of research, and are readily accessible (see FIGS. 5B1, 5B2). There are also preexisting classifications of food and drinks that assign a value as to how satisfying a particular food might be (e.g., a satiety index) that may be used in the illustrative implementations.

Additionally, as explained further below, in illustrative implementations image processing technology may be utilized to identify the food consumed to aid in the identification of caloric and other nutritional/health-related characteristics of the food.

In an illustrative embodiment, an Exercise mode 62 may be entered in which, for example, speech analysis software 8 is utilized to enable the user to input a wide variety of exercise data, as is explained in detail below in conjunction with FIG. 5A. For example, the generated output of various conventional health club and home exercise machines, such as elliptical machines, stationary bicycle machines, stepper machines, etc., that generate, for example, the number of calories burned during an exercise session may be input by a user. In a further implementation, a user lacking the time or desire to enter such data via speech input may choose to input such data by using the mobile computing device's camera to capture the data via a digital photo of the output display of the exercise equipment being used. The system analyzes the image to extract such data as calories burned. It is further contemplated that, in certain implementations, the system may use exercise equipment modified to communicate a user's exercise session data to the mobile computing device 1 via a wired or wireless communication link.

Upon detection of the user entering a GPS-based exercise mode via the GPS exercise icon 64, the system automatically acquires user coordinate position data and monitors the time over which running, walking, or bicycling activities have occurred (e.g., via "Start" and "Stop" screen icons). After user entry of the type of exercise undertaken, the system generates the number of calories burned based on the distance traveled within the time monitored.

Further, in an illustrative implementation, a Food Purchase mode may be entered via the Food Purchase icon 58 to guide the user during food purchasing (at a grocery store or at a restaurant) to determine whether a food product being purchased is consonant with the user's profile, selected diet, and associated goals and health issues. This mode allows a user (in a grocery store shopping or in a restaurant dining) to access a database that identifies alternative products of the same product type. This enables a user, e.g., to select a similar alternative that cuts down on the amount of sugar or calories consumed.

Various other modes (not shown) may be incorporated in the "Select Mode" display shown in FIG. 2B1.

In an illustrative implementation, for each food and exercise activity supported by the system described herein, the system advantageously provides color code feedback to the user with respect to any and all of the many nutritional parameters monitored by the system while taking into consideration the specific health improvement the user is seeking. For example, in an overweight male user trying to lose weight, fruit is color coded "Green" to indicate a very positive choice by the user. However, when providing feedback to an overweight female diabetic user who is trying to lose weight and improve her diabetes control, fruit is color coded either "Orange" or, after surpassing a certain amount of fruit in one day, it turns "Red" due to the sugars in fruit that make it a liability for diabetics.

Similarly, with respect to exercise, for a user with significant arthritis in the knees and hips who is trying to lose weight, treadmill walking is coded red but elliptical machine is coded orange and walking or swimming in a pool is coded green. In an illustrative implementation, exercise duration times are also taken into account by color coding the activity based on the activity itself and the time performing the activity—with too little (or too much) exercise time generating the less desirable color code, all taking into consideration the user's health parameters (heart disease, arthritis, asthma, etc) and the user's goal (to lose or gain weight, improve strength, increase endurance, quit smoking, etc).

FIG. 2C shows an illustrative implementation of a Color-Code Rating Scale Table for generating color-coded ratings using stored thresholds with respect to (WRT) each Food and Exercise item being tracked by the system to provide immediate feedback, guidance, and motivation enabling users to make healthier decisions. The color codes are generated for each food and exercise being tracked and are adjusted for user weight, height, sex, age, health, goals, progress, etc. As the user enters any given food or exercise that he/she is about to consume or undertake, the system rates the relative value of that item WRT the user on a simple scale ranging from 1 to 5 ("Worst"==>"Best"). As depicted for display to the user in the top block 280 of FIG. 2C, the system attaches a symbolic color to each of the 5 rating levels (RED 281/ORANGE 282/YELLOW 283/LIME 284/GREEN 285), which corresponds to a gradually improving relative value (at 290): WORST (starting at the bottom at 0%)==>up to BAD==>up to AVERAGE (passing through 50%)==>up to GOOD==>up to BEST (reaching the top at 100%).

In the illustrative implementation, these 5 colors are an expansion of the ubiquitous Stoplight Colors for traffic control (RED/YELLOW/GREEN) that have become "Stop-and-Go" conventions for traffic worldwide. As such here, they are designed to trigger compulsive, lifelong-conditioned responses in users to "Stop" on RED cues and "Go" on GREEN. The system uses these strong internalized negative/positive stimulants to guide the user to his/her desired goal (lose weight, get stronger, get healthier, etc.): e.g., by hopefully shifting the user over time from his/her worst food items (color RED) to nature's best choices (color GREEN) . . . or by elevating an average exercise such as casual "walking" (color YELLOW) to a better exercise like timed "jogging" (color LIME) . . . and ultimately to a best exercise like "running" (color GREEN).

Moreover, in an illustrative implementation, beyond the "best" GREEN level 285 lies a "Superior" BLUE level 286, which represents an exceptional Food or Exercise value that goes beyond 100% on any scale (e.g., exceeding the user's goal). Any such top value is awarded a BLUE RIBBON by the system for superior performance—which is also a recognized color convention. Finally, as also depicted in top block 280, upon each user Food or Exercise input, the system immediately displays its rating as a RED==>BLUE "button" attached to the item.

The center block 290 of FIG. 2C next provides two pairs of parallel Rating Examples that illustrate how the visually stimulating Color-Code Rating Scale has been applied to every level of the system, top-to-bottom:

Bottom Level: starting at the bottom level, the first pair of examples 291/292 is actually a continuum of parallel ratings that run the gamut for what nature has to offer as a "nutrient" WRT its bad-to-good effect on the human body:

Unhealthy Nutrient 292 runs the gamut from "Worst"–100%==>0% "Best" . . . Healthy Nutrient 291 continues the run from "Worst" 0%==>+100% "Best" . . . so that taken together, the pair runs continuously from −100%==>0%==>+100%

Range Limits: each rating example is expressed as a series of 5 range limits that are calculated WRT a baseline of extremes—i.e., each baseline for a given nutrient is established WRT its most accessible, widely-available Top 5 items (e.g., oranges available from any food store as opposed to Borneo jungle fruit):

Healthy Nutrient 100% baseline 291 is based on its highest-rated Top 5 sources (see FIG. 2E for an example of how a +100% baseline is derived for Vitamin C) Unhealthy Nutrient −100% baseline 292 is based on lowest-rated Worst 5 sources, so the user can be guided from his worst RED snack to Nature's best GREEN food Middle Level: at the system mid-level displays are Straight-Line Curves 293 for linear functions, such as milligrams (MGs) for a given Vitamin or Mineral from all food sources. Such a curve is a linear plot of MGs—fewest (RED) to most (GREEN)—where all increments are the same size from 0%==>100% (see FIG. 2E for an example of how Vitamin C would plot as a straight line, where each 20% increment of 15 MGs corresponds to 11 unique food items)

Top Level: at the top level of system displays are Changing-Rate Curves 294 for non-linear functions such as Weight Loss, which typically starts with a few large increments (40%==>30%) that quickly taper off to smaller increments (20%==>10%) over time. This allows user progress to be displayed as a non-linear RED==>GREEN curve vs. his/her goal curve over a week/month/year (see FIG. 7A4 for an example of how healthy==>to ideal weight tapers off, where each 20% delta of 3 weeks tapers off from 4==>3==>2==>to 1 pound which shows, for example, as often experienced by professional boxers, how difficult it is to burn off the last few pounds).

FIGS. 2D1 and 2D2, which is largely self-explanatory, illustrates a database that delineates, in light of the current state of the art, essential nutrients that the human body needs to function properly, together with color codes for each nutrient. Macronutrients (FIG. 2D1) are nutrients the body needs in larger amounts (e.g., >10 grams), and micronutrients (FIG. 2D2) are nutrients the body needs in smaller amounts (e.g., mostly<1 gram) so that it can perform all of its functions properly. Although micronutrients are only needed in minute amounts, their deficiency can ultimately lead to critical health problems.

The database illustrated in FIG. 2D1 shows various categories of macro nutrients, together with their Daily Value (DV) in MGs at 2000 cal per day. The macronutrient categories of essential nutrients for the human body include carbohydrates, sugars, dietary fiber, cholesterol, dietary fat, and proteins. As shown in the left-most column of FIG. 2D1, each macronutrient is further associated with a color code that identifies whether it is good, bad, or somewhere in between. For example, saturated fats (DV=20 g) are associated with a color code of Red that indicates the worst level of health, because Americans typically get far more than 20 g per day—particularly from hamburgers and french fries (e.g., see FIG. 4C for McDonald's Big Mac and TGIF's seasoned fries). In contrast, polyunsaturated fats such as Omega-3 fatty acids rate a Blue Ribbon, color because they promote an extremely level of health—yet many Americans seldom eat these foods (e.g., see FIG. 4C for a side-by-side comparison of Salmon and Turkey with the items above, all at 220 g serving size). Although Omega-6 fats are essential macronutrients, they appear in such large quantities in the typical American diet, they become harmful since the huge excess starts quickly shifting into significant weight gain—hence, for Americans, in this example, they rate the color Orange. Cholesterol provides another prime example as to how the color codes described herein can serve to help the user. Since it has been reported that the body can only generate approximately 70% of the cholesterol it needs, it still needs an additional 30% from daily food sources (hence, DV=300 mg). However, to avoid making matters worse, the user should find foods that provide more of the good "Green" HDL than the bad "Red" LDL. FIG. 2D1 shows how the system assigns the 5 color codes RED==>GREEN to the 5 rungs of the Cholesterol Ladder so as to maintain the equilibrium of the cholesterol equation:

Total Cholesterol (mg/dL)=HDL+LDL+Triglycerides/5 (mg/dL) which is unlikely to be calculated or tracked or tracked by most individuals The 5 rungs of the Cholesterol Ladder are displayed as 5 corresponding colors to the user for each food with meaningful levels of HDL/LDL cholesterol FIG. 2D2, which is also largely self-explanatory, is an illustration of essential nutrients-micronutrients database identifying color coding levels for each nutrient that the body needs to function properly. The database illustrated in FIG. 2D2 is based upon nutrient and daily value (DV) data taken from a published USDA database (e.g., downloadable directly from USDA websites) and shows various categories of micronutrients together with their daily value (where a daily value has been established) in micrograms at 2000 cal per day. With respect to food and nutrition tracking, it is significant for users to be aware of whether the foods they are consuming provide the required amounts of nutrients identified in the database of FIG. 2D2. As indicated in FIG. 2D2, each of the associated categories of vitamins, carotenoids, macro minerals, micro minerals, and various trace minerals are color-coded to indicate their Green and Blue Ribbon ratings, indicating their extremely high nutritional value (caveat: no DV can be established for trace minerals since their subtle functions are generally too difficult to isolate). The international-standard USDA Nutrient DB (delineated in FIGS. 4B1 and 4B2) contains all of the above essential nutrients (identified in FIG. 2D), except vitamin B7 (biotin), E (4 tocotrionols), zeaxanthin, iodine, and molybdenum.

FIG. 2E provides an illustrative example of how color code ratings from RED==>to GREEN can be derived for any given nutrient, such as vitamin C, by using its Top 5 food sources to create a 100% baseline. FIG. 2E depicts one way the system can assign 5 color codes RED 1==>5 GREEN to five 20% increments that reach the 100% baseline as an upper limit (as illustrated in FIG. 2C).

With respect to the exemplary nutrient Vitamin C, FIG. 2E shows an exemplary subset of food sources for vitamin C (in 2 pairs of columns) that are both commonly known and widely available in food stores, which helps make the search for high-quality food more user-friendly. The qualifying foods are shown in descending order of milligrams (mg) of vitamin C per 100 g (3.53 oz) for each food item (extracted primarily from the USDA Nutrient DB shown in FIGS. 4B1 and 4B2).

As illustrated in FIG. 2E, the exemplary 100% baseline for Top 5 sources of vitamin C is set as follows: There are relatively few extremely high sources of any given nutrient like vitamin C. For example, Acerola, Gooseberry, and Rose Hips are all very high sources of vitamin C—yet, they are not commonly known nor widely available at typical food stores, but rather, are primarily used to manufacture vitamin C tablets. Similarly, Jalapeno Peppers and red/green Chili Peppers are 3 more very high sources of C, but they too must be dismissed as too "spicy hot" for the general public. Hence, in this example, a Top 5 food for any given nutrient must meet 4 significant "user-friendly" qualifications:

commonly known to the vast majority of users
  widely available In food stores throughout the country
  palatable to the vast majority (eliminating "hot spicy" foods)
  consumable in portions >1 ounce (eliminating many garnishing spices Thus, looking back at the top Vitamin C foods in FIG. 2E, the Top 5 sources of vitamin C that meet these criteria would be #1 Red Pepper (190 mg), #2 Kale (120 mg), #3 Kiwifruit (93 mg), #4 Broccoli (89 mg), and #5 Brussels Sprouts (85 mg), where Cauliflower and Green/Yellow Peppers are considered best peer alternates within the same food group as #4 Broccoli and #1 Red Pepper.

100% Baseline and 5 Color Code Increments:

Once this process qualifies the Top 5 for Vitamin C, a 100% baseline can be drawn beneath the #5 qualifier (Brussels Sprouts) at "greater than 80 mg" such that all foods >80 mg of vitamin C are now considered @ Blue Ribbon level 6. In the example shown FIG. 2E, the 5 color code levels are sequentially assigned in 15 mg increments, e.g., Green @>59, Lime @>44, Yellow @>29, Orange @>14, and Red @ 0-14 mgs, such that there are about 11 food items per each 20% increment of 15 milligrams. Note that there are thousands of foods not identified in FIG. 2E (too numerous to mention) that fall into Red level 1 @ 0-14 mg, which merely indicates to the user that they offer the lowest amount of vitamin C. Moreover, from a potency standpoint, FIG. 2E also reveals that most foods yield the highest levels of Vitamin C in their raw form, and that boiling/freezing/canning them invariably reduces their Vitamin C content—often significantly—and that there are few animal sources since Vitamin C is water-soluble.

Figure 2F:
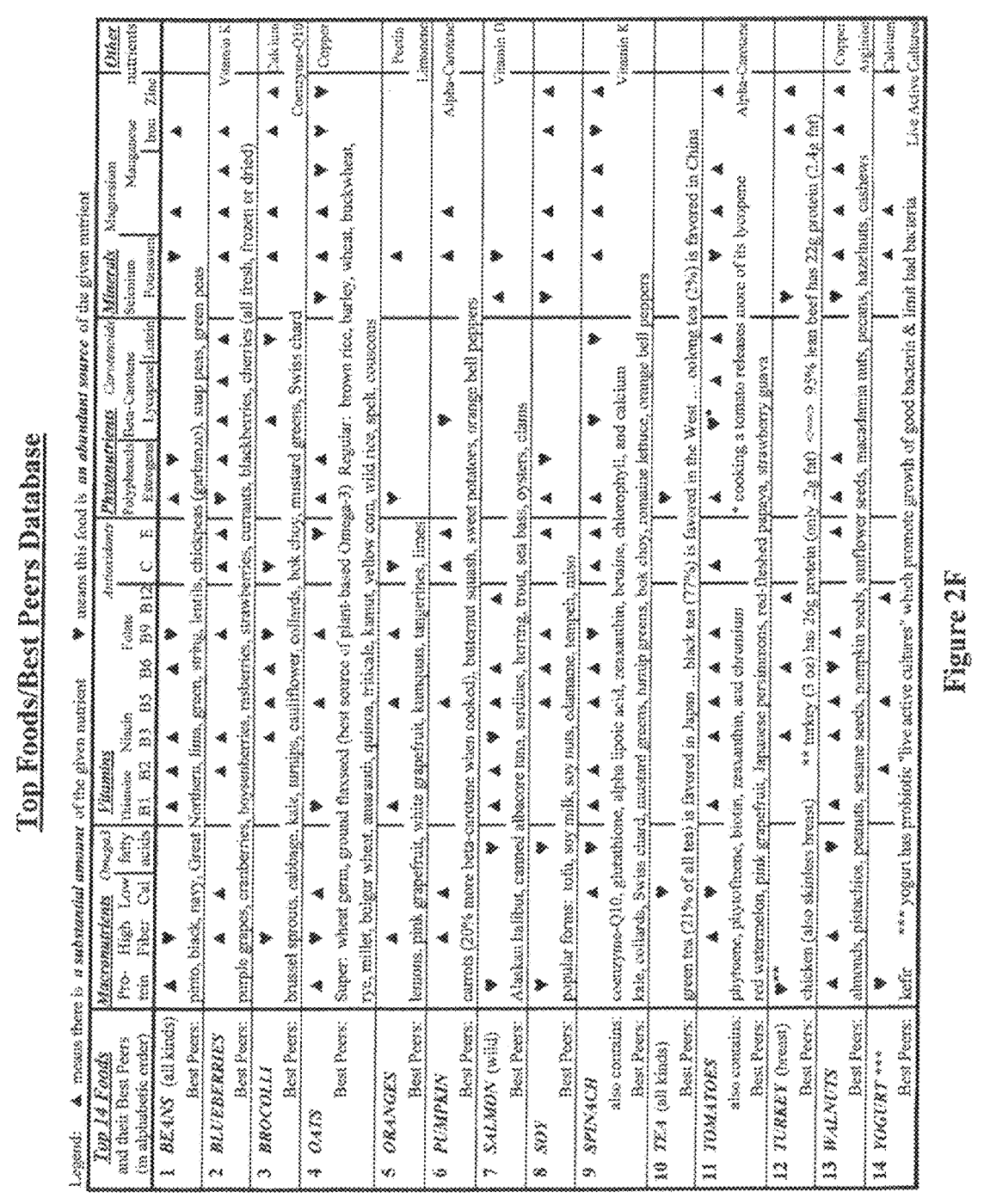

FIG. 2F is an illustration of a Top Foods database identifying various nutritional characteristics of such foods and identifying related top foods (best peers) in the same food family. As indicated in FIG. 2F, the top 14 foods are rated in terms of their content of macronutrients, vitamins, phytonutrients, minerals, and other nutrients. The database identifies the macronutrients of protein, high fiber low calorie and omega-3 fatty acids and tracks the content of vitamin B1, B2, B3, B5, B6, B9, B12, C, and E. The database stores an indication for each of the identified categories of macronutrients, vitamins, phytonutrients, minerals, and other nutrients whether the food provides a substantial amount of the given nutrient, indicating that it is a substantial source of the nutrient and whether this food is an abundant source of the given nutrient, indicating that the food has a much higher quantity of the nutrient than a substantial amount.

Each of the foods indicated in the illustrated column one of the database is one of nature's finest sources for the identified macronutrients, micronutrients, and minerals, especially where it serves as an abundant source. The database also includes a link to a list of related foods, or best peers, to the identified top food. The database is utilized as a source for providing alternative recommendations of foods so that the system can encourage users, for example, to replace an unhealthy selection with a Top 14 healthy choice (or a best peer). In an illustrative embodiment, users may be encouraged to replace an unhealthy food selection with a healthier selection on a step-wise basis using best peers selected from this database, then stepping up the food ladder to a Top 14 healthy choice. The database also provides a user who has already chosen one of the top-ranked healthy foods with an array of alternate healthy foods to form a weekly food cycle.

FIG. 2G1 shows a database containing an illustrative array of recommended daily intake (RDI) values for various categories of users. This RDA database delineates the daily calories required to sustain men and women of varying age, weight, and level of physical activity. For example, as shown in FIG. 2G1, a man weighing 110 pounds is assigned an RDI of 2000 calories, whereas a woman of the same weight is assigned an RDI of 1500 calories. Similarly, a man weighing 176 pounds is assigned an RDI of 3500 calories, whereas a woman weighing 176 pounds is assigned an RDI of 3000 calories. This 500 calorie difference between men and women at the same weight can be attributed to men being typically more muscular than women (i.e., muscles weigh more than normal body fat). Additionally, adjustments to RDI are made based upon whether the user's nominal physical activity is sedentary, moderate, or heavy. Note that these generic levels have been further discriminated into specific user activities, with associated calories burned across 30 minutes, in FIGS. 5B1 and 5B2. As further illustrated in FIG. 2G1, RDIs are differentiated on the basis of age, i.e., linear calorie increments for 3-year age groupings of children, boys, and girls, followed by single calorie values for adult men, women, and pregnant women, followed by modulated values for senior men, women, and lactating women. (all groups are assumed @ average healthy weight/height for their given age) Here are nutritional points revealed by this illustrative database:

RDI varies considerably with age, sex, body weight, and physical activity
  the singular DV of 2000 calories will only sustain a healthy woman @ 132 lbs
  DV of 2000 applies to all women age 19-60, but only if they remain @ 132 lbs
  the singular DV of 2000 cals only applies to a healthy 9-year old boy @ 110 lbs
  DV of 2000 is not sufficient for any man >110 lbs or for any boy >age 9
  the singular DV of 2500 cals applies to all men age 19-60, but only @ 132 lbs
  all DVs must be modulated UP for higher weight/heavier activity/pregnancy/etc.

FIG. 2G2 shows that the RDI described in FIG. 2G1 can be flexibly modulated up/down from the singular DV of 2000 calories. And, looking at the expansion of RDI ranges for Protein/Carbs/Fat/Saturated Fat, FIG. 2G2 further shows that such modulations to higher RDIs (e.g., for heavier healthy men) are strictly linear from 1800 cals/day==>DV @ 2000==>2500 cals/day. As explained below, the system described herein calculates a Recommended Daily Intake (RDI) precisely tailored to each user per the Recommended Daily Intake (RDI) database in FIGS. 2G1-2G2. This RDI differs from USDA's ubiquitous "DV for a 2000 calorie diet" (that is strictly applicable to women @ 132 lbs or less). The system's RDI can be fine-tuned to each user's age, sex, activity level, obesity level, current weight, ideal weight, and body frame, which applies to just about every medium- and large-frame Male/Female above 5' 2" in the Ideal Weight database of FIG. 13C—a significantly high percentage of Americans, Canadians and Europeans. Note that the system can still index user weight against the traditional 2000-calorie DV baseline to remain compatible with the de facto USDA standard, but the above-described illustrative implementation's personalized RDI is more relevant and more encouraging for most users of the system to achieve reachable weight goals.

FIGS. 3A-3F show examples of what the user first sees and does upon downloading, in an illustrative implementation, mobile computing device application software (app) embodying the functionality described herein. After the app is initialized (at 31 in FIG. 2A), the newly-stored app launches its module to create a User Profile (32 in FIG. 2A) which, in this example, is built upon many efficient system constructs:

Purpose: To capture as much personal user information as possible up front, when the user is first introduced to the system, in an effort to keep tedious, repetitive user inputs to a minimum in the future. This also showcases the expandable functionality of the system and provides a baseline to which the system can compare future user activity.

Strategy: To capture the minimum data items required for the system to be of the desired degree of help to the user, and then encourage the user to select as many optional favorite data items as he/she is willing to share. However, even if the user fails to provide all his/her ID data, assumptions can be made about the items that allow the system to proceed, but with the caveat of possibly degraded, less relevant recommendations to the user (see below).

Parallel Audio/Visual Prompts: In an illustrative implementation, system prompts and feedback are offered via parallel synthesized voice and touch-screen visual displays substantially simultaneously, to which the user can respond alternatively by voice or touch (which, inter alia, allows users with heavy foreign accents or speech impediments to more successfully participate).

Open-Ended Lists: In an illustrative implementation of the Create User Profile Mode (described below), each category in the User Profile displays a set of popular exemplary items to get the first-time user started. This is intended to stimulate the user to visualize and enter as many of his/her own favorite choices as he/she wishes (up to a preset limit N). With all the thousands of foods and exercises that exist, such open-ended lists allow a user to expand his/her profile selectively in all food/exercise categories. This process efficiently personalizes each user profile, without having to maintain/display exhaustive checklists of every food and exercise.

Quantified Items: In an illustrative implementation, wherever appropriate, data items entered by the user are next quantified by asking "How Much?" with respect to food/nutrition (pounds/pints/ounces) or exercise (pounds/reps/distance)—e.g., "12-ounce steak" or "100-pound bench press for 3 reps"—so that the system can accurately calculate calories in versus calories out for the user as the quantified items appear in the future.

Exercise Tags: In an illustrative implementation, wherever appropriate, exercise items entered by the user are quantified with "How Long?" (hours/minutes) and "How Often?" (times per week)—e.g., "jog for 30 minutes" or "tennis match for 2 hours" (duration tags in the system database) plus "3 times per week" (frequency tags). Such extended data gives the system a revealing snapshot (or baseline profile) of what foods and exercises the user is already engaged in and at what level.

Nutrition Tags: In an illustrative implementation, wherever appropriate, each nutrition item selected by the user is further qualified by the system with nutrient tags representing its nutrient value per unit (including, inter alia, calories, carbs, fats, cholesterol, sugars, fiber, protein, vitamins, minerals, omega-3s, herbs, antioxidants, etc.), plus an overall rating tag representing its relative value to user health from 1 to 5 (explained below). These short nutrition and exercise tags are further examples of how the system efficiently expands user profiles outward while keeping storage to a minimum.

Parallel System/User Databases (DBs): In an illustrative implementation, all items accepted from the user are stored immediately in the user DB within the mobile computing device's (e.g., smart phone's) local memory 15, and then later as a cumulative batch update in the parallel system DB within remote server 14. Having a parallel, for example, smart phone DB allows the user to view/update/add items to his/her DB locally offline at his/her convenience, without tying up the phone with unnecessary, sustained low-activity communication to the remote server. Equally important, it enables the user to access his/her DB in remote areas and enclosed buildings (such as restaurants/spas/gyms) that often have degraded or no phone signal.

Streamlined Database Structure:

In an illustrative implementation, tracking the wide range of every possible snack-to-dinner food item and low- to high-energy exercise requires many "wordy" user inputs each day across long periods of time. Hence, in an illustrative implementation, the system DB structure has been radically streamlined to minimize its size and to curb its exponential growth. In this example, all of this starts with the User Profile Create mode (below) where, e.g., each open-ended list is constrained to actual user choices 1-N (as above) and quantified with short tags (as above). In such an implementation, the User Profile Create mode generates a single baseline record from initial user inputs that the user can later expand, one item at a time, in any food or exercise category. However, none of these long "wordy" entries (1-N) are repeated in subsequent daily records where any repeat is represented by a simple binary "ditto" (1-N). Thus, in an illustrative implementation, the system DB has one long baseline record followed by a string of short daily records that can compress the span of many years into a small disk area.

FIGS. 3A through 3F show an illustrative implementation of the process flow and data structure of the User Profile Create mode (see table below), which prompts the user for all data required by the system in this example (such as his/her current weight and ultimate goals) and all optional data he/she is willing to share beyond that (such as Top 5 favorite foods and exercises). In other implementations, alternative required data may be designated. All this data entered, taken together, comprises the user's primary baseline record from which, in an illustrative implementation, the system makes initial recommendations (such as an initial diet and exercise regime to pursue) as a first step toward achieving his/her ideal weight, tempered by any applicable restrictions (due to handicaps, injuries, meds, etc.). The Create mode captures this primary baseline User Profile, and is run only once up front, upon initial launch of the system—as the first pass through the User Profile module. Thereafter, the user can selectively view and change any of his/her initial profile data in the Modify mode during any subsequent pass through the User Profile process shown. However, other than expected user weight updates and user preference updates to goals or rewards, any user changes to his/her permanent baseline data in an illustrative implementation are challenged by warnings and confirmations (e.g. "Are you sure?") in order to maintain user profile integrity.

The table below summarizes various aspects of the creation of illustrative user profiles, subsequent revisions/modifications thereof, user profile-related process flow and exemplary data structures involving food and exercise. Various user profile features and data structures are explained in detail below particularly in conjunction with the referenced FIGS. 3A-3F.

| FIGS. 3A-3F: User Profile Create Mode (initial pass) and Modify Mode (thereafter) | | | |
|---|---|---|---|
| LEVEL | USER PROFILE | FOOD | EXERCISE |
| User | User ID/Health Data | User Preferences | User Preferences |
| Input | Baseline Record in FIG. 3A | FIGS. 3A ==> 3C | FIG. 3D ==> 3F |
| Top | System Process | Top 5 User Choices | Top 5 User Choices |
| Level | Modular Flowchart | FIG. 3A | FIG. 3D |
| Middle | System Structure | Categories/dishes/tags | Categories/modes/tags |
| Level | Modular Block Diagram | FIG. 3B | FIG. 3E |
| Bottom | System Database | Popular Examples | Popular Examples |
| Level | Matrix of Open-Ended Lists | FIG. 3C | FIG. 3F |
| Tag | As-Needed System Tags | Illustrative Examples | Illustrative Examples |
| Level | Quantifying/Qualifying Data | FIGS. 3A ==> 3C | FIG. 3D ==> 3F |

Figure 3A:
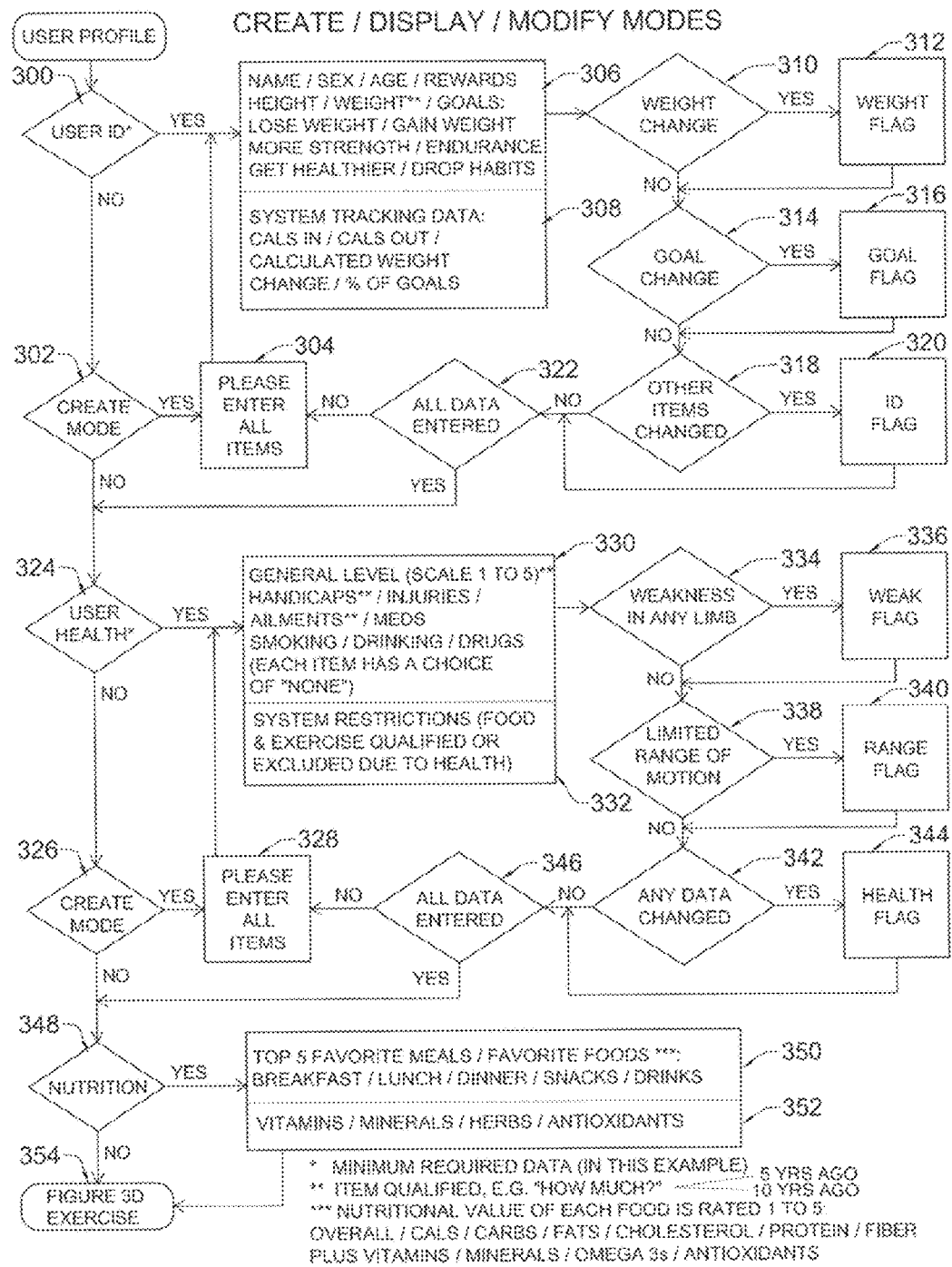
FIGS. 3A and 3D are an illustrative flowchart depicting an exemplary sequence of operations underlying the creation of a complete initial User Profile, including user ID and Health data.

In an illustrative implementation, as shown in FIG. 3A, upon entry, the User Profile program (UP) presents 4 icons to the user: User ID 300, User Health 324, Nutrition 348, and Exercise 400 that, for example, may be displayed via touch screen icons (and may be viewed as software generated "keys" or "buttons") on the user's mobile computing device 1 (e.g., a smart phone). In this example, these appear sequentially in the Create Mode and all at once in the Modify Mode, along with an EXIT icon at, for example, the lower RH corner. Hence, if the user hits any, for example, user touch screen icon button other than "User ID" (NO out of 300), the UP tests for Create Mode at 302 and, if the UP is in the Modify Mode, advances to User Health 324 (NO out of 302). Otherwise, UP prompts the user to "please enter all ID items" at 304 and returns to enter User ID data 306, as will next be delineated item-by-item.

In the Create Mode, in an illustrative implementation, the user selects User ID in order to enter the following Minimum User ID data 306 for the system in this example:

Name: required in an illustrative implementation to maintain a unique baseline record for each person—but since all kinds of aliases may arise, such as initials, first/last name only, nicknames, screen names, etc., the UP may add unique numbers to make each user name unique Sex: required in an illustrative implementation to calculate his/her ideal weight via the Ideal Weight DB, and to recommend exercise regimes appropriate to his/her natural motions and limits Age: required in an illustrative implementation to differentiate higher-to-lower calorie requirements to account for the younger, more energetic teenagers . . . to the older, more sedentary retirees Height: required in an illustrative implementation to calculate ideal weight via the Ideal Weight DB, ranging from 4'10"==>6'6" for both men and women (the DB can be further extended for taller/shorter users, if necessary)

Weight: required in an illustrative implementation to calculate ideal weight via the Ideal Weight DB (FIG. 13C), to serve as the primary baseline to compare successful weight loss (or gain) and, from a system point of view, to calculate reasonable increments to achieve ideal weight—in illustrative implementations, the DB has been structured to permit an accurate determination of ideal weight, taking into account various user characteristics. In some of these illustrative implementations, the UP may ask for user weight "5/10 years ago" to glean a historical trend.

Wrist Size (FIG. 12B): may be advantageously used to differentiate body frames via the Ideal Weight DB as small/medium/large—a revealing, user friendly measurement (takes 30 seconds) that can serve to discriminate between such worldwide healthy extremes as:

Women (small frame)<==>Women (large frame, both healthy)

@ healthy weight MIN edge @ healthy weight MAX edge

Note: Wrist Size is a more user-friendly measurement than the more difficult Elbow Size that was initiated by Met Life in 1942 (see FIG. 12B)

Waist Size (FIG. 12C): required to differentiate obesity level via the Ideal Weight DB as healthy/overweight/obese—a revealing, user friendly measurement (takes 30 secs) that can serve to discriminate between such worldwide obesity extremes as:

Women (large frame)<==>Women (large frame, same height)

@ healthy weight MAX edge @ obese weight MIN edge

Note: this metric can also separate muscular healthy athletes from obese people at the same height and weight.

Goals: although the most commonly desired goal today is to lose weight, the system is designed to handle a wide variety of users: from obese to underweight, from out-of-shape weak to perfectly fit, from sick to healthy, etc. Thus, the system has been designed to handle user goals that are going to vary accordingly:

from lose weight==>to gain weight from get stronger==>to last longer (more endurance)

from get healthier==>to drop bad habits (e.g., smoking/drinking/drugs)

Note: in illustrative implementations, the user has the option of selecting as many goals as desired; e.g., most people would like to get healthier while they are trying to lose weight.

Timeframe: used to calculate reachable increments toward the user goal across a reasonable time interval with a typical range of 1-2 lbs per week Rewards: a significant factor in achieving goals—in this case, it is a user reaching an incremental goal toward resurrecting his/her own health and body. In illustrative implementations, rewards are downloaded iTunes and Netflix movies—and these can be expanded to prizes (for achieving a long sought-after goal) such as dinner at an organic free-range chicken restaurant Default User ID data: for an illustrative implementation, all the above items are considered minimum User ID data needed to calculate an ideal weight for any given user, and to facilitate him/her achieving that goal (or any other goal above) via reachable increments toward that goal that are rewarded proportionally. It should be understood that in some illustrative implementations, apart from all the above minimum User ID data needed to calculate a user's ideal weight, the system can just as easily be run with a few token values made up by the user, or even none at all, if desired by a particular user. That is, the user could simply experiment with the system by plugging in any token height/weight/sex and look to see how the system would go about resolving a typical overweight male/female, e.g.:

Male: 5'9" @ 195 lbs (assumed to be about 16 lbs overweight)

Female: 5'4" @ 170 lbs (assumed to be about 24 lbs overweight)

Furthermore, it is noted that this system can be run without any of the minimum User ID data—e.g., as an exemplary "trial demo" (for a user who has no desire to enter data) by, for example, making a few real-world assumptions regarding the user, who could be an average U.S. male/female (whose actual weight/height/overweight level are listed above). The average U.S. male/female are then compared to an "ideal" average male/female at a similar height—in this case, an average German male/female, whose average weight is deemed "ideal" by the Ideal Weight DB shown in FIG. 13C. That is, assuming no user inputs at all, the system can perform a realistic trial demo with representative Males and Females from around the world, using their actual average Heights and Weights, to show how the system can work to bring obese people back to healthy weight, as follows:

| Trial Demo Parameter | German (avg) Ideal Weight | | Weight Loss Increment* per Time Interval | | | | American (avg) Overweight | |
|---|---|---|---|---|---|---|---|---|
| | Male | Female | M/F | M/F | M/F | M/F | Male | Female |
| Height | 5' 10.1" | 5' 4.9" | | | | | 5' 9.4" | 5' 4.2" |
| US Delta (in) | -0.7" | -0.7" | 4th | 3rd | 2nd | 1st | +0.7" | +0.7" |
| Weight | *181.7* | *148.8* | <=== | <=== | <=== | <=== | *195.3\** | *170.2\** |
| US Delta (lb) | -13.6 lb | -21.4 lb | | | | -6/-9 | +13.6 lb | +21.4 lb |
| Adjust for .7" | -1.8 lb | -1.9 lb | | | -5/-8 | | +1.8 lb | +1.9 lb |
| Weight Loss | -16 lb | -24 lb | | -3/-5 | | | +16 lb | +24 lb |
| US GOAL | *180 lb* | *146 lb* | -2/-2 | | | | | |
| Chart Slice | *healthy* | *healthy* | <=== | <=== | <=== | <=== | *Obese* | *Obese* |
| System Color | Green | Green | Lime | Yellow | Orange | Red** | *Red* | *Red* |

*Using 1% total weight as an initial safe MAX weight loss increment:
Time interval here is 3 weeks for Men ==> yielding 6 lbs in 3 months (8% loss)
Time interval is 6 weeks for Women ==> yielding 24 lbs in 6 months (14% loss)
**See the System Color Code Rating in FIG. 2C for the 'stoplight' sequence and for the non-linear weight loss increments here as a changing-rate curve Minimum User Clicks: In illustrative implementations to promote enhanced user friendly data entry, the User Profile module is streamlined to yield the highest level of system output for the least number of user input "clicks" (where a "click" can be, for example, a written or spoken entry or a choice from a displayed list) to keep the user enthusiastic and locked in throughout the initial Create mode, as follows:

| | User Profile: how increasing Create Mode Inputs ==> yields higher-level System Outputs | | | | |
|---|---|---|---|---|---|
| System | Initial User Inputs for each Higher Level of System Output | | | | User |
| Output Level | User ID | User Health | FOOD | EXERCISE | Clicks |
| Trial Demo (no user clicks) | 0 | 0 | 0 | 0 | 0 |
| Healthy Weight (2 user clicks) | Height/Weight | 0 | 0 | 0 | 2 |
| Ideal Weight tailored to User | Above plus Age/ Sex/Wrist/Waist | Current Health plus 4 "nones"* | 0 | 0 | 11 |
| Weight Loss Diet + Exercise | Above plus Goal/ Time/Reward | same as above | Top Meal** for 5 categories | Top Exercise** for 5 categories | 24 |

| User Profile: how increasing Create Mode Inputs ==> yields higher-level System Outputs | | | | | |
|---|---|---|---|---|---|
| System | Initial User Inputs for each Higher Level of System Output | | | | User |
| Output Level | User ID | User Health | FOOD | EXERCISE | Clicks |
| Fast Track toward all goals | same plus Weight "5/10 years ago" | same plus Health "5/10 years ago" | Top 5 Meals plus tags*** | Top 5 Exercises plus tags*** | 36+ tags |

*User Health only requires 4 "none" answers for people with no health problems (otherwise, people with injuries/ailments/handicaps/meds enter data as needed) Thus, in 11 clicks, a user can see Ideal Weight precisely tailored to his/her body
**Food/Exercise, in this example, only require one Top Meal/Exercise to initiate diet/exercise plan (otherwise, the user can enter as many Top Choices 1 ==> 5 as he/she is willing). Thus, in 24 clicks, a user can get an initial Weight Loss plan tailored to him/her.
***all tags (sauces/vitamins/quantity/sets/reps/etc.) are optional in Create mode (tags become more important attached to actual eating/exercise in Modify mode) Thus, in 36 clicks, a user can get the fastest track (diet + exercise) to his/her goal.

Maximum User Choices in Minimum Time: In illustrative implementations, to facilitate the user's food/exercise entries shown in the above table, the UP has also been streamlined at all levels to provide the User the maximum number of popular choices (primarily, via the open-ended lists of FIGS. 3C/3F) to identify his/her "favorite" preferences in a rule-of-thumb telescopic 10× focusing process,* as follows:

| User Profile: how a large Server DB gets telescoped 10X down ==> to a small Phone DB | | | | | |
|---|---|---|---|---|---|
| Telescopic | System Actions | | User Actions | | User |
| 10X Process* | Filters ==> | Offers ==> | Chooses ==> | Uses ==> | Prefers |
| when used/ where stored | online access to Server DB* | User Profile Food/Exercise | offline access to Phone DB* | Modify Mode Food/Exercise | Create Mode |
| Level | Global ==> | Standard ==> | Relevant ==> | Favorite ==> | Top 5 |
| FOODS | 100,000 ** | 10,000 | 1,000 *** | 100 | 25 |
| EXERCISES | 10,000 ** | 1,000 | 100 *** | 10 | 5 |

Figure 3B:
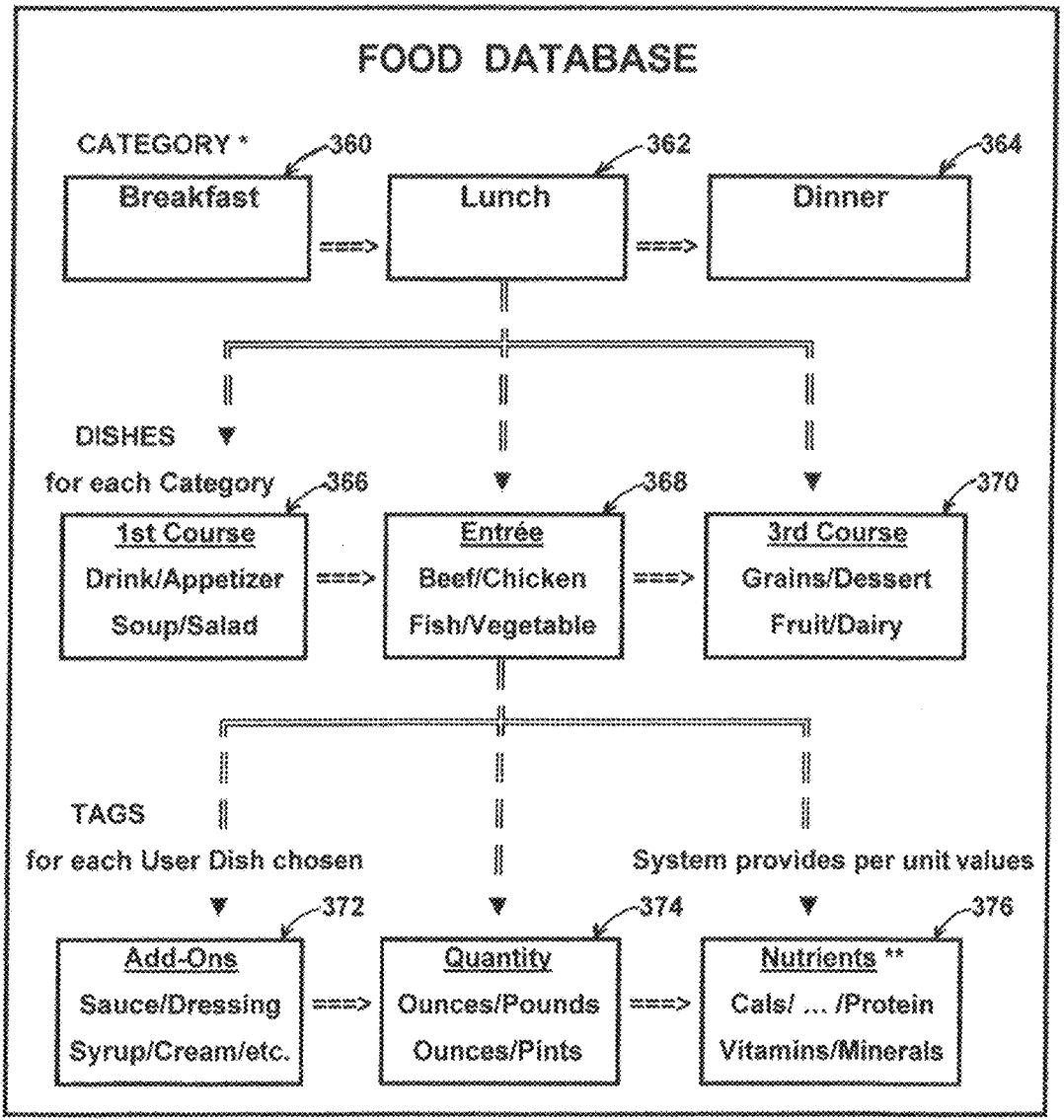
FIG. 3B shows an exemplary process for FIG. 3A by which the system captures, stores, and updates food data in the user's Food Database on a wide variety of foods for breakfast, lunch, and dinner, as well as each snack and drink outside of meals.
Figure 3D:
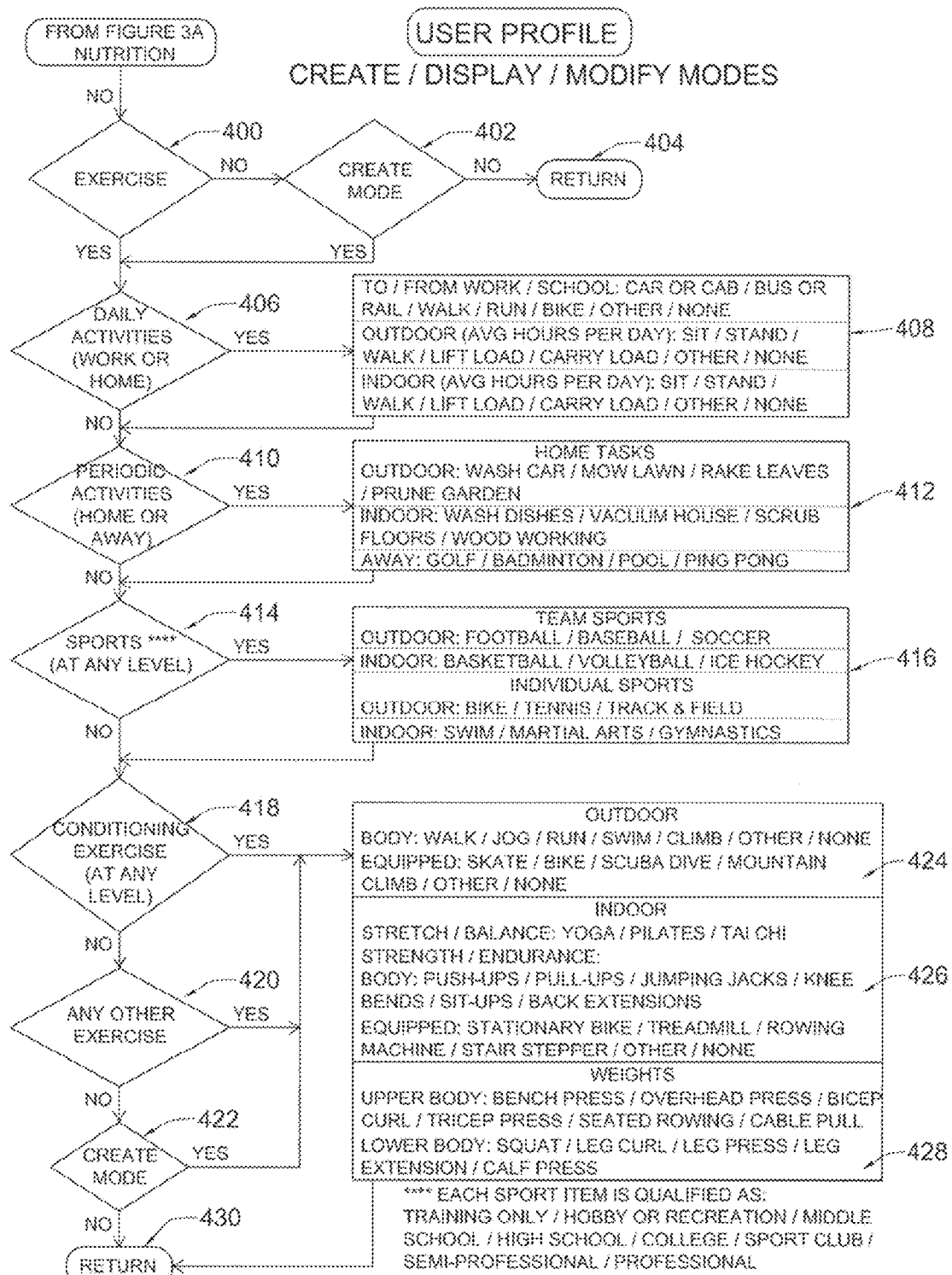
Figure 3E:
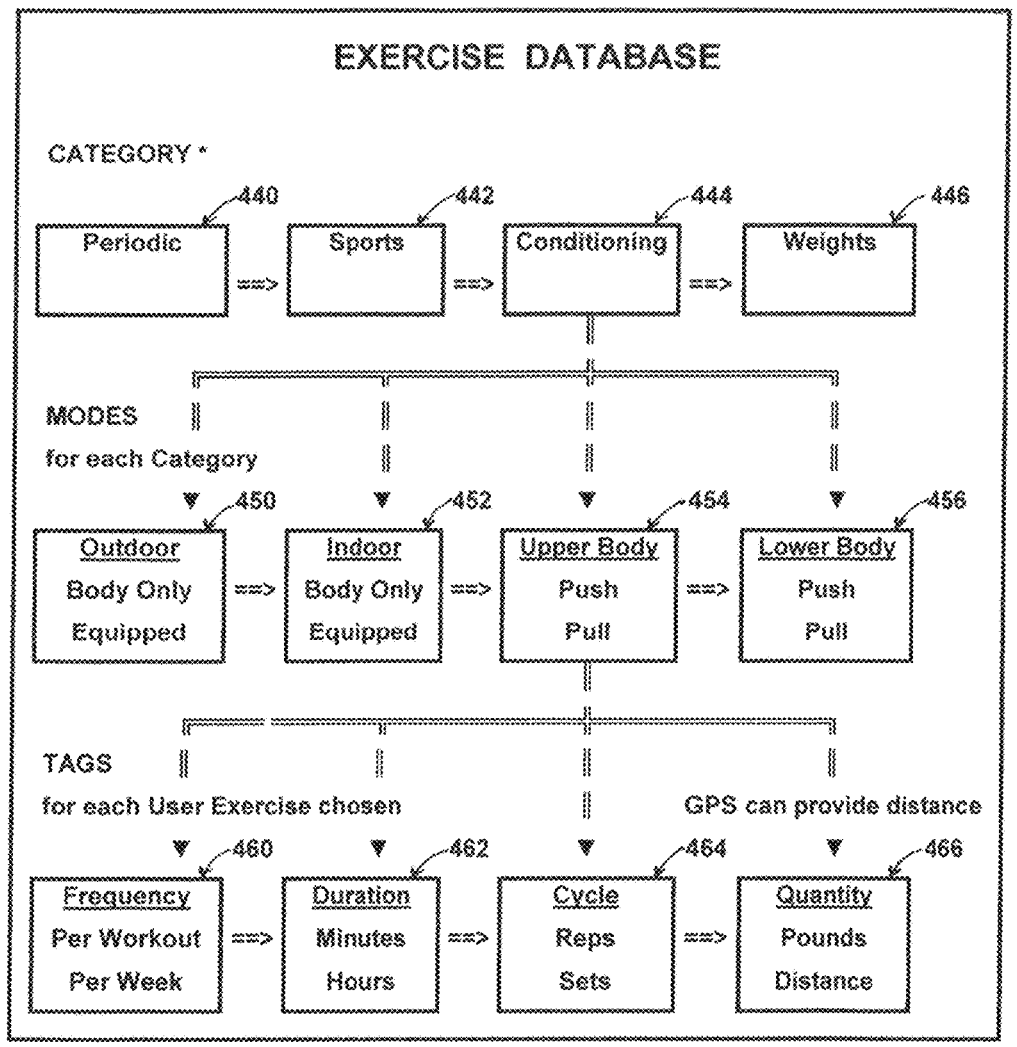
FIG. 3E shows an exemplary process for FIG. 3D by which the system captures, stores, and updates exercise data in the user's Exercise Database on a wide variety of exercises performed by a user daily or periodically, or otherwise for playing sports, non-competitive conditioning, or weightlifting.

*This chart illustrates how the system telescopes the large reservoir of global foods/exercises down several 10X levels to a small relevant number a user can use, reducing the size of the mobile computing device DB (e.g., an IPhone) down to what the user can still use offline.
** Global levels illustrate how the system efficiently strips out specialized items (like ethnic foods/exercises) from standard American foods/exercises, so the vast majority of users can scan faster through shorter, more familiar open-ended lists (specialized/ethnic choices are still available to the minority by typing them in).
*** Relevant levels illustrate how, despite the vast array of potentially better foods/exercises out there, human nature still tends to favor just "a precious few" - the goal of the Create mode here is to tease out the precious few from the user and gradually nudge him/her from a suspect few to the more relevant healthier many, as will next be described for Nutrition (FIGS. 3A-3C) and Exercise (FIGS. 3D-3F).

Turning back to FIG. 3A, once the user enters the above Minimum User ID data 306 (or if default data is utilized) in the Create Mode, UP can now establish his/her Ideal Weight via the data base illustrated in FIG. 13C, and can next calculate the initial baseline System Tracking Data 308 based on that weight:

Ideal Weight: in illustrative implementations, the data base illustrated in FIG. 13C zones in on an ideal weight for both Men and Women and for people with different body frames and vastly different levels of obesity. As in any system, the higher the level of precision to pinpoint correct ideal weight means the higher the level of precision for all calculations that follow (below)

Weight Loss Increments (or "deltas"): UP calculates a reachable weight "delta" within a periodic interval (week/biweek/month/etc.) based on his/her specified timeframe, all of which is precisely tailored to each user Recommended Daily Intake (RDI): UP calculates an RDI precisely tailored to each user per the RDI database in FIG. 2G1. This RDI differs from the USDA's ubiquitous "DV for a 2000 calorie diet" (that is primarily applicable to women @ 132 lbs or less). The system RDI can be fine-tuned to each user's age, sex, activity level, obesity level, current weight, ideal weight, and body frame, which applies to just about every medium- and large-frame Male/Female above 5' 2" in the Ideal Weight data base of FIG. 13C—which is a significantly high percentage of Americans. UP can still index user weight against the traditional USDA 2000-calorie DV baseline, but UP's personalized RDI is more relevant and more encouraging for most users of the system to achieve reachable weight goals.

Calorie Counters: UP maintains a set of running Calories IN/Calories OUT counters that keep track of running daily/weekly/monthly amounts of Calories IN (from food eaten by the user) versus parallel running amounts of Calories OUT (from exercise by the user) that can be selectively displayed or plotted by the user. UP maintains these counters based on food eaten (where each gram of protein or carbs=4 Calories, each gram of fat=9 Cals, each gram of alcohol=7 Cals, etc.) and based on user exercise to balance out the food eaten (where each pound worked off=3500 Calories). Thus, at any given time or for any given timeframe, weight loss can be easily calculated via the delta between Cals IN vs. Cals OUT:

Weight Loss Delta (lbs)=(Cals OUT−Cals IN)/3500 Cals per pound

Goal Percentage (%): Armed with these pairs of running Calorie Counters, at any given time or across any given timeframe, UP can now maintain a corresponding set of running Goal Percentages (%) with respect to the user's specific ideal weight and/or current weight increment above, as follows:

Current Goal (%)=current Weight Loss Delta/current Weight Increment

Ideal Weight Goal (%)=cumulative Weight Loss Deltas/(Baseline Weight−Ideal Weight)

In an illustrative implementation, the above Calorie Counters and Goal Percentages are displayed on the user's mobile computing device 1 screen as running display counters, or as more stimulating color X-Y plots of Weight across Time—e.g., as cumulative weight loss vs. successive weight increments.

User Profile Modify Mode: the above System Tracking Data 308 is initialized by the Create Mode at the user's declared Goal(s) and Weight, plus UP-calculated Ideal Weight. Beyond these initial baseline entries, all remaining user tracking functions—including successive weight increments, calorie counting, and goal percentages—are performed by the Modify Mode during subsequent UP passes, following the same process flow shown in the flowchart of FIG. 3A.

Parallel Audio/Visual Interface: As set forth above, in an illustrative implementation, all User Profile prompts and feedback, as well as all user choices for data entry and/or next course of action, are offered to the user via simultaneous, parallel synthesized voice and touch-screen video, to which the user may respond alternatively by voice or touch.

Turning back to FIG. 3A and the User ID entry processing, after the user has finished entering Reward as his/her final choice in Minimum User ID data 306, UP tests at 310 whether the user changed his/her current Weight, which is an expected response. If so, it sets the Weight Flag 312 for further processing by the mainline routine in FIG. 2A—if not, it proceeds to test at 314 whether the user changed his/her current Goal. If so, UP sets the Goal Flag 316 for the mainline routine (as above)—if not, it proceeds to test at 318 whether the user changed any other Minimum User ID data 306—e.g., any change to the user's height, or sex would be suspicious. If so, UP first warns the user as to the danger of such a change to his/her profile integrity and asks "Are You Sure?" to confirm that the change was intended (not shown). If so, it sets the ID Flag 320 for the mainline routine (as above) —if not, it proceeds to test at 322 whether the user has entered all Minimum User ID data 306. If not, UP prompts the user at 304 to "please enter all ID items" and returns to re-enter User ID data 306—if so, it proceeds to test User Health 324.

After finishing User ID processing, if the user hits any icon but "User Health" (NO out of 324), the UP tests for Create Mode at 326 and, if it is in not in the Create Mode, but is in the Modify Mode, advances to Nutrition 348 (NO out of 326). Otherwise, UP prompts the user to "please enter all Health items" at 328 and returns to re-enter User Health data 330, as will next be delineated item-by-item.

In the Create Mode, in an illustrative implementation, the user must select User Health to enter the following Minimum User Health data 306 for the system to optimally assist in recommending food/exercises that are not otherwise unsafe or even harmful. It is expected that individuals will be open and honest about their handicaps, ailments and injuries.

General Level of Health: in an illustrative implementation used to actively elicit from a user a rating defining the user's self-image of his/her own health, on a color-coded scale of Worst 1==>5 Best. In illustrative implementations, UP next may ask the follow-up "What level 5 and 10 year ago?" to glean a historical trend.

In illustrative implementations, each item below has "None" as the first answer to accelerate healthy users through this Health section as quickly as possible.

Injuries: In illustrative implementations, UP first asks whether a user's injury is permanent or temporary (with a date for expected recovery). It then asks what areas of the body are affected, such as skeletal, muscles, organs, nerves, brain, etc., followed up, as needed, by what limbs such as (right or left) hand/foot/arm/leg/torso/back/neck/etc. Such a body injury profile guides the system away from bad limbs to help the remaining good ones Ailments: In illustrative implementations, ailments such an diseases (cancer, diabetes, etc.), and allergies. UP follows the same inquiry process as that above to identify specific Injuries, except that ailments often imply a weakening of the entire body which can preclude, e.g., eating certain foods and nutrients, exercising outdoors, exercising the remaining healthy limbs (as above), etc.

Handicaps: In illustrative implementations, UP follows the same inquiry process as that above to identify specific Injuries except handicaps often imply a severe weakening of entire limbs or the entire body which can complicate any system trying to help them, e.g., mobility limited to a wheelchair, exercise limited to special gym equipment, etc.

Addictions/Health Impacting Bad Habits: Only addictions and habitual behavior that significantly affect body health and/or normal exercise—namely, smoking, drinking, and drugs—are embraced in illustrative implementations tracking these activities. Here, UP asks the simple question of frequency, "How often?" on a scale of Seldom 1==>5 Every Day. However, focusing on these three activities does not in any way preclude adding any number of other habitual behaviors that affect health and/or exercise to a lesser degree, or that involve fewer people.

Medications: Each of the above Health issues can require Meds that may be inconsistent with or interact with certain foods/nutrients/supplements the system might normally recommend. Therefore, UP asks in illustrative implementations for whatever Meds the user is taking regardless of the specific health reason, to avoid such unnecessary, potentially hazardous conflicts.

Historical Trends: Finally, for each of the significant injuries, ailments, handicaps, and bad habits, UP asks the follow-up "What level 5 and 10 year ago?" (optional) to glean a historical trend that may influence recommended exercises and/or diets.

In an illustrative implementation, once the user enters the above Minimum User Health data 330 in the Create Mode, UP can now establish the system baseline User Restrictions 332 based on, for example, the injuries/ailments/handicaps/bad habits/meds disclosed by the user, and set RED flags on all foods/diets and exercise regimes that should be excluded due to them, particularly during subsequent passes in the Modify Mode. In an illustrative implementation, these RED flags are backed up by a RED Zone Body chart (not shown) that flags affected body areas.

FIG. 3A User Health (continued): After the user has finished entering Medications as his/her final choice in Minimum User Health data 330, UP asks the user at 334 if he/she has any Weakness in any Limb (beyond the Health data 330) that could affect normal exercise regimes (i.e., any motion limited right/left, up/down, CW/CCW. If so, it sets the Weak Flag 336 (i.e., a RH/LH flag for each affected limb) for further processing by the mainline routine in FIG. 2A—if not, it asks the user at 338 if he/she similarly has any Limited Range of Motion (beyond the Health data 330). If so, it sets the Range Flag 340 for the mainline routine (as above)—if not, it proceeds to test at 342 whether the user changed any other Minimum User Health data 330—e.g., any change to the user's handicaps or permanent injuries would be suspicious. If so, UP first warns the user as to the danger of making such a change to his/her profile integrity and asks "Is this an update or a correction?" plus "Are You Sure?" to confirm that the unexpected or inconsistent change was intended (not shown). If so, it sets the Health Flag 344 for the mainline routine (as above)—if not, it proceeds to test at 346 whether the user has entered all the Minimum User Health data 330, which includes "None" as the most common answer for each Health item. If not, UP next prompts the user at 328 to "Please enter all Health items" and returns to re-enter User Health data 330—if so, it proceeds to Nutrition 348.

FIG. 3A Nutrition: As shown in FIG. 3A, in an illustrative implementation, if the user selects the Nutrition icon (YES out of 348), UP proceeds to capture high-level Nutrition inputs at 350—otherwise, it exits (NO out of 348) to Exercise at 354 that is explained in detail in conjunction with the description of FIG. 3D. As described above, a goal of the Create mode at 350 here is to encourage a user to enter certain favorites identifying his/her Top 5 favorite meals among Breakfast/Lunch/Dinner/Snacks/Drinks (which are the system's 5 Food categories). While picking out 5 favorites for each of the 5 categories is not required, in this example, UP encourages the user to specify at least his/her #1 "all-time" favorite items (per the Minimum User Click chart above) which, for Breakfast, could be as complex as a havarti cheese/egg soufflé with sauteed shrimp and avocado . . . or as simple as a piece of buttered toast.

Vitamins/Minerals: Similarly, in an illustrative implementation, a goal of the Create mode at 352 is to encourage a user to enter certain favorites identifying his/her Top 5 favorite supplements among Vitamins/Minerals/Herbs/Omega-3s/Antioxidants (which are the system's 5 supplement categories), following the same user input process as above. For Vitamins, this could be as complicated as all eight Vitamin E tocopherols and tocotrienols (each has alpha/beta/delta/gamma variations) or as simple as a One-a-Day multi-vitamin (the process for specifying Top 5 is described in detail next with FIGS. 3B/3C).

Color-Coded Foods/Nutrients: As shown and illustrated in FIGS. 2C/2D (above), in an illustrative implementation, all the elements of the entire system from top-to-bottom are color-coded with a 5-color rating of RED 1==>5 GREEN (beyond which lies a sixth "Blue Ribbon" category). Thus, in an illustrative implementation, each of the above Nutrition icons (from Breakfast==>Dinner Top 5 meals and from Vitamins==>Antioxidant Top 5 supplements) will always be displayed to the user in its system-rated color RED==>GREEN on the user's color screen. This reinforces the underlying "bad-to-good" nutritional value of each food or exercise that the user is presently engaged with or is planning to move up to.

Top-to-Bottom Color Codes: In an illustrative implementation, this color-code rating extends across the entire system—from top-to-bottom. For example, at the highest level, each meal (Breakfast/Lunch/Dinner) is color coded with a RED==>GREEN color based on the weighted-average color of all its food elements (drink/appetizer/entree/vegetable/dessert/etc). This same color rating extends all the way to the lowest level where, for example, each food item is color-rated WRT its cals/carbs/sugars/fiber/fats/cholesterol/protein/etc—as well as its total vitamins/minerals/omega-3s/antioxidants/etc—each nutrient individually.

Hence, to satisfy likely user curiosity, the inquisitive user can click on any color-coded icon (food/vitamin/exercise/etc.) to find out exactly what lower-level element (high LDL cholesterol/low protein/slow walking pace/etc.) caused the RED ALERT.

Moreover, this top-to-bottom color-coding serves to educate the user as to each item's "bad" RED elements that were otherwise "hidden" from his/her view prior to using this system—revealing why he/she should move up to the next-higher level food choice. Alternatively, it reveals what he/she has to do to correct and/or improve a RED exercise.

User Health/Attitude Profile: One significant function of storing a user's food/nutrient favorites is to piece together a revealing snapshot of the user's current health—and his/her collective attitude toward healthy eating via Top 5 Meals and adequate nutrition via Top 5 Vitamins—presumably formed over many years. Taken together with Top 5 Exercises (gathered via parallel FIGS. 3D-3F below) and a user history from "how much 5/10 years ago?" (gathered above), the resulting 5-10 year health/attitude profile of a new user allows the system to more accurately gauge just how much to soften (or harden) the resulting recommended diet plan for a pre-established "average" YELLOW male/female, to which the system will otherwise default. Such data, in an illustrative implementation, may be used as follows:

On the positive side: if the user reveals a long-term healthy diet profile, the system can more aggressively "harden" the recommendations toward the highest GREEN level foods to accelerate the user directly to his/her ideal weight—such "hardening" is especially important for already fit athletes, who easily qualify for this group.

On the negative side: however, if the user reveals a long-term unhealthy diet profile, in an illustrative implementation, the system may, for example, cautiously "soften" the recommendations toward the lowest RED level—such "softening" avoids overburdening an obese user with average goals that are beyond his/her physical reach and current diet attitude. Such a plan may be modified as desired to accelerate obese users towards goal achievement based upon a medical need to do so, or an indication from an analysis of performance data that the user is ready for more accelerated goal achievement.

For more details on how this strategy is fine-tuned, see the discussion on how food are adapted to each user by the Create mode in FIG. 3C.

Food Database: FIG. 3B is a modular block diagram for the Food Database which follows in FIG. 3C. The basic structure of the DB shown in FIG. 3C is a virtually 4-dimensional (4D) array, including:

[1] the top-level Categories (horizontal axis across FIG. 3C)

[2] the middle-level Dishes (vertical axis down FIG. 3C, grouped as 3 courses)

[3] an Open-Ended List for each mid-level Dish (into the paper in FIG. 3C)

[4] the bottom Tags attached to each open-ended List (orthogonal to above 3 axes)

As shown in FIG. 3B, in this illustrative implementation, the UP access sequence for this Food DB is broken into 5 major Categories: Breakfast 360/Lunch 362/Dinner 364 plus Snacks 384/Drinks 385 (not shown here for clarity, but as shown in FIG. 3C). UP accesses each of the 5 categories as follows:

[1] the top-level Categories (horizontal axis across FIG. 3C)
[2] the middle-level Dishes (vertical axis down FIG. 3C, grouped as 3 courses)
[3] an Open-Ended List for each mid-level Dish (into the paper in FIG. 3C)
[4] the bottom Tags attached to each open-ended List (orthogonal to above 3 axes)

The UP access sequence for this Food DB is broken into 5 major Categories: Breakfast 360/Lunch 362/Dinner 364 plus Snacks 384/Drinks 385 (not shown here for clarity) as shown on FIG. 3C. UP accesses each level as follows:

UP accesses these 5 Categories sequentially (as shown by the top arrows), overflowing into Snacks 384/Drinks 385 on FIG. 3C before exiting.

Next, for each of the 3 meal categories, UP cycles through the 3 Dishes: 1st Course 366/Entrée 368/3rd Course 370 (as shown by the middle arrows).

Within each of the 3 Dishes, UP cycles through 4 Meal Items that, taken together comprise 12 unique items for each meal (as listed at 366/368/370), the significance of which is explained in more depth in FIG. 3C (below).

Within each of the 4 Meal Items, UP cycles through the 3 Tags at the bottom: Add-Ons 372/Quantity 374/Nutrients 376 (as shown by the bottom arrows), which are selectively created as-needed to qualify or quantify the item.

Finally, the last Tag—Nutrients 376—is generated by UP as a helpful FYI for the user, with RED==>GREEN codes displayed with each nutrient to educate him/her as to the relative GREEN value or RED danger posed by that Meal Item, and the Meal as a whole (as discussed at Color-Coded Foods/Nutrients above).

Moreover, it is hard to grasp the significance of the first Tag—Add-Ons 372 —until the system calculates the total calories added to meal items by the Add-On examples (sauce/dressing/gravy/syrup/cream/etc.) that can downgrade an ordinarily healthy slice of turkey to RED ALERT, as will be discussed in depth next with FIG. 3C.

Food Database Meal Matrix: FIG. 3C is a modular block diagram of the Food Database accessed in FIG. 3B. For breakfast, lunch, dinner, snacks and drinks, examples of popular choices are displayed to the user so that the user may select from the open ended list and choose meals that need not be repetitively input. For example, the user need only define breakfast #1, lunch #3, dinner #5, etc., one time and then conveniently select such meals by identifying breakfast #1, lunch #3, or dinner #5. In this example, the user enters up to 5 favorites for each category, starting with his #1 favorite food, e.g., yogurt. FIG. 3C illustrates the same Food Database shown as a modular block diagram in FIG. 3B, formatted here into a 5×12 Meal Matrix that is virtually a 4-dimensional (4D) array of open-ended Lists (except for the 3C Snacks/Drinks) with the following 4 independent axes:

[1] the 5 Categories corresponding to horizontal Matrix columns 381==>385
[2] the 12 Dishes corresponding to vertical Matrix rows 387==>398, except that Snacks/Drinks (columns 384/385) are not indexed to the 12 Dishes (column 380)
[3] the 60 Open-Ended Lists corresponding to each cell in the 5×12 Matrix array, where each cell initially contains a popular example to stimulate User choices
[4] the 3 Tags attached to each of the 60 Open-Ended Lists (180 max Tags) where:

Add-Ons 372 initially contain a popular example, like sauce/dressing/syrup/etc.

Quantity Tags 374 are generated by the user after he/she eats each food/meal Nutrient Tags 376 are generated/displayed by the system upon user request Top 5 Favorite Meals: UP initially asks the user to enter up to 5 Favorites for each Category 381==>385, starting with his/her #1 favorite food, and optionally entering up to 4 or more favorites per category at user discretion. At any time from this juncture on, the user can conveniently select any "repeat" favorite by its sequence number among the Top 5 Favorite lists—for example:

Breakfast #1==>Lunch #2==>Dinner #3==>Snack #4==>Drink #5 which saves the user all the time and effort to re-enter the same Favorite food/meal This initial system/user interplay over Top 5 Favorites provides the opportunity for UP to find out exactly what the user's attitude toward food is, and perhaps even explain where all his/her excess weight (if any) came from—e.g., even if the user doesn't eat the favorites very often. Knowledge of the users urges may be significant in guiding the user towards a more healthy diet.

The system advantageously matches the 60 food examples shown in the initial matrix of FIG. 3C to the RED 1==>5 GREEN quality of food that the user, for example, identifies as favorites to eat.

Based on all the above User ID/User Health inputs (that will normally yield an ideal weight and target weight loss goal for the user) coupled with the skeletal user "5/10 years ago" history data, UP can gauge which initial 1==>5 level to display. That is, as an illustrative embodiment here, the 60 examples shown in FIG. 3C vary through all 5 color levels from RED 1 (e.g., malted Milk Shake) to 5 GREEN (e.g., Iced Tea with lemon). An illustrative strategy is to present most of these 60 examples at the 1==>5 food level the user can identify with and/or actively seeks out. By this illustrative strategy, UP may elicit a more realistic/honest answer from users than by suggesting they pick among "better" foods they know they really should be eating. In an alternative implementation, the system may suggest a range of better foods for the user to identify as favorites.

This initial Create mode strategy dovetails with the higher-order strategy of an illustrative implementation of the entire system to facilitate weight loss (or gain), which can be accomplished more effectively when the system knows the exact diet/exercise profile of the user:

at the obese RED extreme, in an illustrative implementation, UP will present all the customary RED foods that likely enticed certain users to become obese in the first place, to avoid wasting their time with GREEN foods they already ignore, and to otherwise establish an accurate RED baseline at the healthy GREEN extreme, UP will present all the high-caliber GREEN foods that fit athletes are already aware of and/or eating religiously, to avoid wasting their time with RED foods they already dislike, and otherwise establish an accurate GREEN baseline One such illustrative system strategy is to boot-strap each user from his/her current RED==>GREEN level (as just described) up the diet ladder, one notch at a time, as shown with the Meat Ladder below:

| MEAT LADDER | OBESE WEIGHT MAX =====> MIN | OVERWEIGHT MAX =====> MIN | HEALTHY BODY FRAME* MAX =====> MIN |
|---|---|---|---|
| Best GREEN Nutrients | Highest ==> Protein/Fiber/Omega-3/HDL/Antioxidants/Vitamins/Minerals/Potassium Lowest ==> Calories/Double Sugars/LDL/Saturated Fats/Trans Fats/Sodium | | |
| 6> BLUE | | | (3 ounce serving for all meats) 98 Cals/20.1 g Protein/1.3 g Fat ==> light Turkey |
| 5> GREEN | | | 97 Cals/19.7 g Protein/1.3 g Fat ==> light Chicken |
| 4> LIME | | | 106 Cals/17.1 g Protein/3.7 g Fat ==> dark Chicken |
| 3> YELLOW | | Round Steak <== 121 Cals/18.4 g Protein/4.7 g Fat | |
| 2> ORANGE | | Sirloin Steak <== 171 Cals/17.3 g Protein/10.8 g Fat | |
| 1> RED | Rib Roast <== 260 Cals/14.1 g Protein/22.2 g Fat | | |
| Worst RED Nutrients | Highest ==> Calories/Double Sugars/LDL/Saturated Fats/Trans Fats/Sodium Lowest ==> Protein/Fiber/Omega-3/HDL/Antioxidants/Vitamins/Minerals/Potassium | | |

*This is the MAX ==> MIN range for a small/medium/large frame Healthy User

As can be seen from the essential macronutrients database of FIG. 2D, the rib roast is high in calories, low in protein, and high in fat when compared to the light turkey shown in the above chart. The calories, protein, and fat parameters for rib roast are unhealthy and merit a red rating. In contrast, white meat turkey calorie, protein, and fat parameters are healthy and merit a blue rating. The diet ladder chart shows that the rib roast alternatives of sirloin steak, round steak, dark chicken, and light chicken provide increasingly healthy choices that a user may progress through on a stepwise basis to habitually consume more healthy products.

Thus, this Meat Ladder chart illustrates an illustrative system strategy of boot-strapping the user at any diet level—e.g., obese RED==>healthy GREEN—up the ladder, one step at a time—from the fattening RED rib roast or ORANGE sirloin steak, up the ladder toward the GREEN light chicken or ultimate BLUE light turkey This Meat Ladder concept illustrates how the system can make a user healthier: i.e., there is a similar 5-color food ladder for each one of the 60 Open-Ended Lists by which the system can improve a user's diet, one step along one ladder at a time.

In one implementation, the system operates to recommend healthier foods to a user as follows. In an illustrative implementation, after a user has selected a food such as "rib roast," the system will encourage the user to "step up the ladder" by selecting a healthier alternative that is next highest up the ladder of related foods, such as described in the meat ladder above. In this implementation, the healthier alternative is added to the users "favorites" list in a highlighted fashion ((e.g., displayed higher up the favorites list based upon a displayed color code indicating a "healthier choice" than the red colored rib roast) with a frequency count of zero indicating that the user has not selected the food at this particular point in time. However, the presence of the food in the user's favorites list will serve to encourage future selection by the user.

Turning back to FIG. 2F, as noted above, the illustrated top nutrition foods database identifies top foods and top related foods (best peers) from the same food family that may be used to encourage users to modify their diet to eat the identified high nutrition foods as part of breakfast, lunch and dinner and as possible alternatives to less healthy choices made by the user. This database illustrates various top rated, highly nutritious natural single foods widely-available from food stores and includes links identifying alternative related highly nutritious foods in the same or similar food groups.

Thus, one or more of the foods shown in FIG. 2F may be suggested to the user as an alternative to a less healthy choice in a similar manner to a user's choice of "rib roast" may lead to a display of the above meat ladder in the meat example shown above. In this example, FIG. 2F identifies Top 14 natural foods along with their best peers in the same food family—i.e., these 14 ultimate foods (and their best peers) are at the top of the ladder for many of the Open-Ended Lists.

FIG. 3D Exercise: The flowchart described above in FIG. 3A continues in FIG. 3D and focuses on the user profile exercise subsystem. As shown in FIG. 3D, upon exiting Nutrition at 354 (FIG. 3A), if user hits the Exercise icon (YES out of 400), UP proceeds to capture high-level Exercise inputs starting with Daily Activities at 406. Otherwise, UP exits (NO out of 400) to test Create Mode at 402 and, if it is in the Modify Mode, returns at 404 to the system Mainline at 25 (FIG. 2A). Otherwise (YES out of 402), UP returns the user to consider making initial data entries in Daily Activities at 406.

Although in this example there is no minimum required data here in Create Mode, as a purely "common sense" rule of data entry, in one implementation, UP obliges the user to at least consider each of the five Exercise categories of Daily Activities, Periodic Activities, Sports, Conditioning Exercise, and Weightlifting (406/410/414/418/428). Each of the exercise categories in FIG. 3D may be selected by a user in a display depicting the exercise categories identified above as icons that may be selected for data entry by the user. If the user does not see any applicable exercises therein, he/she can just quickly select "none" to proceed on.

Moreover, other than lifting weights, there are enough ubiquitous activities (e.g., "sit at work (perhaps the lowest level of activity)" or "walk outdoors"), that all but handicapped users are likely to do them. Forcing such an obligatory first look at each category, serves to introduce the user to the vast array of exercises he/she can get credit for.

As described earlier for Nutrition (FIG. 3A), a goal of the Create mode at 408 here is to encourage the selection of favorites from the user as to his/her Top 5 favorite exercises for each of the system's five categories. The user's favorite exercise list is initially built through processing described below in conjunction with FIGS. 5A and 5B regarding the user selecting the "activities," "sports," and "conditioning" icons, selecting favorites from these categories and generating color codes, and calories burned data associated with the exercise and characteristics of the user including the user's body weight. The favorites list continues to expand over time as the user actually performs new exercises or old exercises with new frequency, duration, cycle, or quantity tags. Such expansion simplifies the user's entry of exercise into the system.

While picking out 5 favorites for each category is entirely optional, UP encourages the user to specify at least his/her #1 "all-time" favorite exercise items (per the Minimum User Click chart above) which, for Daily Activities 408, could be as complex as "lifting a heavy load overhead" . . . or as simple as "sitting at a desk".

Similarly, the goal of Create mode at 424/426 is to encourage the selection of favorites from the user as to his/her Top 5 favorite conditioning exercises among indoor/outdoor regimes and upper/lower body weight lifts 428, following the same optional input process as above. For weightlifting 428, this could be as complex as "max bench press with 2 spotters" or as simple as "wrist curls with 25-lb bar" (the process for specifying Top 5 is described in detail next with FIGS. 3E/3F).

Color-Coded Activities/Exercises: as shown and illustrated in FIGS. 2C/2D/2E (above), in an illustrative implementation, all the elements of the entire system from top-to-bottom are color-coded with a 5-color rating of RED 1==>5 GREEN (beyond which lies a sixth Blue Ribbon rating which would be awarded for, say, a bench press that's 5% beyond the user's max). Thus, in an illustrative implementation, each of the above Exercise icons (from Daily==>Sports Top 5 activities and from Conditioning==>Weightlifting Top 5 exercises) will consistently be displayed to the user in its system-rated color RED==>GREEN on the user's color display screen. This approach reinforces the underlying "bad-to-good" performance value of each exercise that the user is presently engaged with or is planning to move up to.

In this example, color-code rating extends across the entire system, from top-to-bottom. For example, at the highest level, each workout (all sets/reps/weights combined) is color coded with a RED==>GREEN color based on the weighted-average color of all its separate lifts (for torso/upper limbs/lower limbs). This same color rating extends all the way to the lowest level where, for example, each set of a given lift is color-rated for its reps/weight level/rest interval WRT user capability.

Hence, in an illustrative implementation, to satisfy user curiosity, the inquisitive user can click on any color-coded icon (5-mile run, 100-lb lift, etc) to find out exactly what lower-level element (slow pace/weight too low/rest interval too long) caused the RED ALERT.

Moreover, this top-to-bottom color-coding serves to educate the user as to each item's "toxic" elements that were otherwise "hidden" from his/her view prior to using this system—revealing why he/she should move up to the next-higher level. In addition, it points to what he/she has to do to correct/improve a RED exercise.

User Health/Attitude Profile: the underlying motive for encouraging selection of the user's favorites is to piece together a revealing "snapshot" of the user's current fitness—and his collective "attitude" toward healthy lifestyle via Top 5 Activities and healthy conditioning via Top 5 Exercises—presumably formed over many years. Taken together with Top 5 Exercises (gathered via parallel FIGS. 3D-3F below) and a user history from "how much 5/10 years ago?" (gathered above), the resulting 5-10 year health/attitude profile of a new user allows the system to more accurately gauge just how much to soften (or harden) the resulting recommended exercise plan for a pre-established average YELLOW male/female, to which the system will otherwise default—for example:

On the positive side: if the user reveals a long-term healthy exercise profile, the system can freely "harden" the recommendations toward the highest GREEN level exercises to accelerate the user directly to his/her ideal fitness—such "hardening" is especially important for already fit athletes, who easily qualify for this group.

On the negative side: however, if the user reveals a long-term unhealthy exercise profile, in this example, the system will cautiously "soften" the recommendations toward the lowest RED level—such "softening" avoids overburdening an obese user with average goals that are beyond his/her physical reach and current exercise attitude.

For more details on how this strategy is fine-tuned, see the discussion of how exercise examples are adapted to each user by the Create mode in FIG. 3F.

Turning to a more detailed discussion of the flow between the blocks on FIG. 3D, there is no reference to the illustrative examples of typical activities/exercises here that are offered below as "popular examples" in the 5×10 Matrix Array of 50 Open-Ended Lists that, taken together, comprise the Exercise Database (discussed below with FIG. 3F). For any given Activity/Exercise mode, the user can say "none" or enter "other".

Daily Activities 408: upon entry (YES out of 406), UP initially offers the "To/From Work" choices to give the user extra credit for, say, walking to work—then offers the choices of what activities the user performs on a daily basis at work (or school) including at a minimum, "sit at desk", referenced to Indoor or Outdoor, where all user responses are merely his/her estimates of average hours per day. When the user is finished, UP next highlights the icon for Periodic Activities 410.

Periodic Activities 412: upon entry (YES out of 410), UP initially offers simple Home Tasks, such as "mow lawn" or "wash dishes"—then offers some low-energy/recreational Sports away from home—indexed to Indoor or Outdoor. When the user is finished, UP next highlights the icon for Competitive Sports 414.

Competitive Sports 416: upon entry (YES out of 414), UP initially offers Competitive Individual Sports, such as "Martial Arts" or "Tennis"—then offers high-energy Team Sports such as "Football" or "Basketball"—all referenced again to Indoor or Outdoor. UP next qualifies each sport as to its competitive level: training only/hobby or recreational/middle school/high school/college/sport club/semi-pro/pro—in order to establish a ball-park measure of the user's athletic fitness. When the user is finished, UP next highlights the icon for Conditioning Exercise 418.

Conditioning Exercise 424: if the user does not enter this Category (NO out of 418), UP prompts him/her at 420 with "any other exercise not identified yet?" and, if not, tests for Create Mode—if YES out of either test 420/422, UP returns to the user to Conditioning block 424. Either way, upon 424 entry (YES out of 418), UP initially offers Outdoor exercises, first using Body Only, then with Equipment. >Next, UP offers Indoor Strength/Endurance exercises, first using Body Only, then with indoor Equipment—followed by Stretch/Balance exercises like "Yoga"

Finally, UP offers Indoor Weight Training exercises, first for the Upper Body, then for the Lower Body—covering all the opposing muscle pairs (see FIG. 3H).

UP next qualifies each exercise as to its competitive level: (training only/hobby or recreational/middle school/high school/college/sport club/semi-pro/pro) so as to establish a ball-park measure of the user's athletic fitness. When the user is finished, UP next returns at 430 to the system Mainline Routine.

FIG. 3E Exercise Database: FIG. 3E is a modular block diagram for an illustrative Exercise Database which follows in FIG. 3F. Each category rotates through all four modes identified below. Tags are only attached to each exercise selected or added by the user. The basic structure shown for this DB in FIG. 3E reveals it is virtually a 4-dimensional (4D) array, as follows:

[1] the top-level Categories (horizontal axis across FIG. 3F)
[2] the middle-level Modes (vertical axis down FIG. 3F broken into 2 "forces" as described below in the mode description)
[3] an Open-Ended List for each mid-level Mode (into the paper in FIG. 3E)
[4] the bottom Tags attached to each open-ended List (orthogonal to above 3 axes)

UP access sequence for this Exercise DB is broken into 5 major Categories: Periodic 440/Sports 442/Conditioning 444/Weights 446 plus Daily (not shown here for clarity) as shown at 481 on FIG. 3F. UP accesses each level as follows:

UP accesses these 5 Categories sequentially (as shown by the top arrows), starting with Daily Activities 481 on FIG. 3F before entering Periodic 440 here.

Next, for each of the 5 exercise categories (including Daily Activities 481), UP cycles through the 4 Modes: Outdoor 450/Indoor 452/Upper Body 454/Lower Body 456 (as shown by the middle arrows).

Within each of the 4 Modes, UP cycles through 2 Forces that, taken together, comprise all unique types of exercise (as listed at 450/452/454/456), the significance of which is explained in more depth in FIG. 3F (below). With respect to the forces, for the outdoor mode and indoor modes, the forces are identified as body only forces, and equipped forces (force provided through the use of exercise equipment). For the upper body and lower body, the forces are categorized as push/pull forces. Within each of the 2 Forces, UP cycles through the 4 Tags at the bottom:

Frequency 460/Duration 462/Cycle 464/Quantity 466 (as shown by the bottom arrows), which are selectively created as-needed to qualify or quantify the item.

Finally, the last Tag—Quantity 466—includes horizontal ground Distance, which the system can optionally provide via GPS tracking if the user decides to carry his/her mobile computing device 1 equipped with GPS capabilities (e.g., an iphone) along on an outdoor walk/jog/run/skate/bike trip/ etc. Here at the lowest data level, each data item associated with each tag is also displayed with RED==>GREEN color codes to inform him/her as to the relative GREEN positive or RED negative value of that particular exercise parameter, and the Exercise as a whole (as discussed at Color-Coded Activities/Exercises above)

FIG. 3F is an illustrative Exercise Database Top 5 Matrix. In this example, the user enters up to 5 favorites for each category, starting with the exercise done most often (e.g., walk). From this juncture on, the user can conveniently select periodic exercise #1, sports #3, weights #5, etc. This is the same Exercise DB shown as a modular block diagram in FIG. 3E, formatted here into a 5×10 Exercise Matrix that is virtually a 4-dimensional (4D) array of open-ended Lists (except for 3D "To/From Work" 498) with the following 4 independent axes:

[1] the 5 Categories corresponding to horizontal Matrix columns 481==>485
[2] the 10 Modes corresponding to vertical Matrix rows 487==>496, except that To/From Work (column segment 498) is not indexed to the 10 Modes (col. 480)
[3] the 50 Open-Ended Lists corresponding to each cell in the 5×10 Matrix array, where each cell initially contains a popular example to stimulate User choices
[4] the 4 Tags attached to each of the 50 Open-Ended Lists (200 max Tags) where:
    Frequency Tags 460 initially contain a popular example like "3 times per week"
    Duration Tags 462 initially contain popular example like "60 mins per workout"
    Cycle Tags 464 initially contain a popular example like "3 sets @ 10 reps"
    Quantity Tags 466 initially contain popular examples like "100 lbs" or "1 mile" that are later modified or updated by the user after he/she completes a set or a run (or alternatively hits "done" to stop optional GPS tracking for a walk/jog/run/etc.)

Top 5 Favorite Exercises: UP initially asks the user to enter up to 5 Favorites for each Category 481==>485, starting with his/her #1 favorite, and optionally entering up to 4 or more favorites per category at his/her discretion. At any time from this juncture on, the user can conveniently select any "repeat" favorite by its sequence number among the Top 5 Favorite lists—for example: Daily #1==>Periodic #2==>Sports #3==>Conditioning #4==>Weights #5 which saves the user all the time and effort to re-enter the same Favorite exercise.

This initial system/user interplay over Top 5 Favorites provides an opportunity for UP to find out exactly what the user's attitude toward exercise is, and perhaps explain where all his/her excess weight (if any) came from—e.g., even if the user doesn't do the favorites very often, it is his/her urges that count. The system matches the 60 exercise examples shown in the initial matrix of FIG. 3F to the RED 1==>5 GREEN quality of exercise the user loves to do. Based on all the above User ID/User Health inputs (that will normally yield an ideal weight and target weight loss goal for the user) coupled with the skeletal user "5/10 years ago" history data, UP can gauge which initial 1==>5 level to display. That is, as an illustrative embodiment here, the 50 examples shown in FIG. 3F vary through all 5 color levels from RED 1 (e.g., walk slow) to 5 GREEN (e.g., sprint competitively). The strategy here is present most of these 50 examples at the 1==>5 food level he/she can identify with and/or actively seeks out. Hence, by this strategy, UP is able to elicit a more realistic answer from users than by suggesting they pick among "better" exercises they know they should be doing.

This initial Create mode strategy dovetails with the higher-order strategy of an illustrative implementation of the entire system to facilitate weight loss (or gain), which can be accomplished more effectively when the system knows the exact exercise profile of the user:

at the obese RED extreme, in an illustrative implementation, UP will present all the customary RED activities that may have contributed to the user's obesity in the first place, to avoid wasting their time with GREEN exercises they already ignore, and to otherwise establish an accurate RED baseline
    at the healthy GREEN extreme, UP will present all the high-caliber GREEN exercises that fit athletes are already aware of and/or doing religiously, to avoid wasting time with RED activities they dislike, and otherwise establish an accurate GREEN baseline.

One such illustrative system strategy is to boot-strap each user from his/her current RED==>GREEN level (as just described) up the exercise ladder, one notch at a time, as shown with the Walk/Run Ladder below:

| WALK/RUN LADDER | OBESE WEIGHT MAX ====> MIN | OVERWEIGHT MAX ====> MIN | HEALTHY BODY FRAME* MAX ====> MIN | |
|---|---|---|---|---|
| Best GREEN Parameters | Highest ==> Healthy/at or near Ideal Weight/toward Max Heart Rate (see FIG. 3G) | | | |
| | Modulators ==> Height vs. current Weight/Gender/Age/Obesity level/Fitness level | | | |
| 6> BLUE | 40 yards @ 6 seconds (or) 100 yards @ 12 seconds ==> | | | Fast Sprints |
| 5> GREEN | 1 mile @ 6 minutes (or) 5 miles @ 35 minutes ==> | | Fast Run | |
| 4> LIME | 5 miles @ 50 minutes ==> | | Slow Run | <== 1 mile @ 9 minutes |
| 3> YELLOW | | Slow Jog | <== 1 mile @ 11 minutes | |
| 2> ORANGE | | Walk/Jog | <== 1 mile @ 15 minutes | |
| 1> RED | Slow Walk | <== 1 mile @ 30 minutes | | |
| Worst RED Parameters | Highest ==> bad Health profile/Obese now/Obese 5-10 years ago/below Min Heart Rate | | | |
| | Modulators ==> Height vs. current Weight/Gender/Age/Obesity level/History/Health | | | |

*This is the MAX ==> MIN range for a small/medium/large frame Healthy User

This Walk/Run Ladder illustrates the prime system strategy of boot-strapping a user at any exercise level—e.g., obese RED==>healthy GREEN—up the ladder one step at a time—from the slowest RED walk time or ORANGE Walk/Jog time, up the ladder toward the GREEN fast run time or ultimate BLUE fast sprint time This Run/Walk Ladder illustrates how the system can make a user healthier: i.e., there is a similar 5-color exercise ladder for each one of the 60 Open-Ended Lists by which the system improves user exercises, one step along one ladder at a time.

Figure 4A:
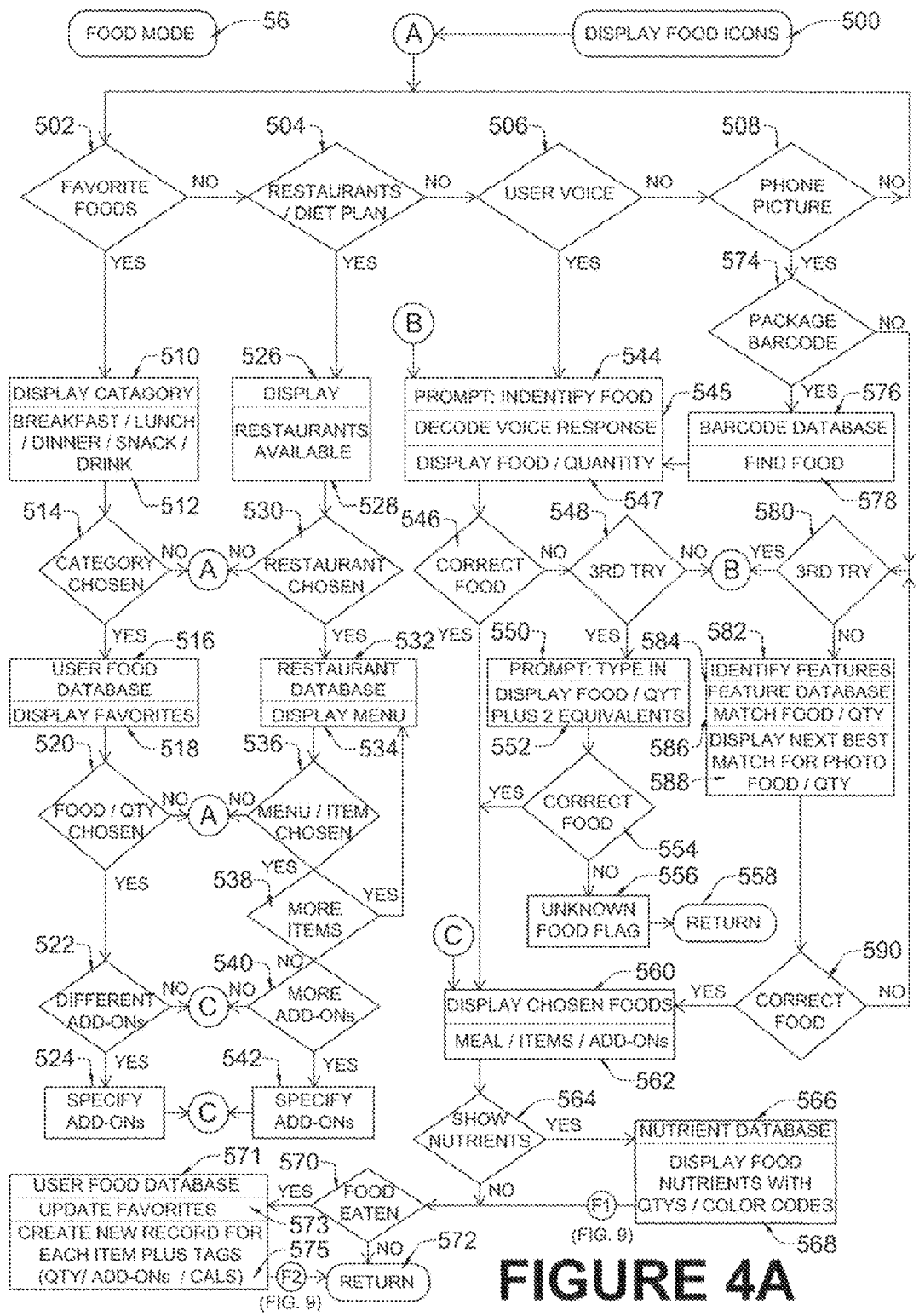
FIG. 4A is an illustrative flowchart for the system Food Mode depicting an exemplary implementation of 4 different ways the user can access his/her Food DB to view/modify its contents or add new items eaten to the DB.
Figure 5A:
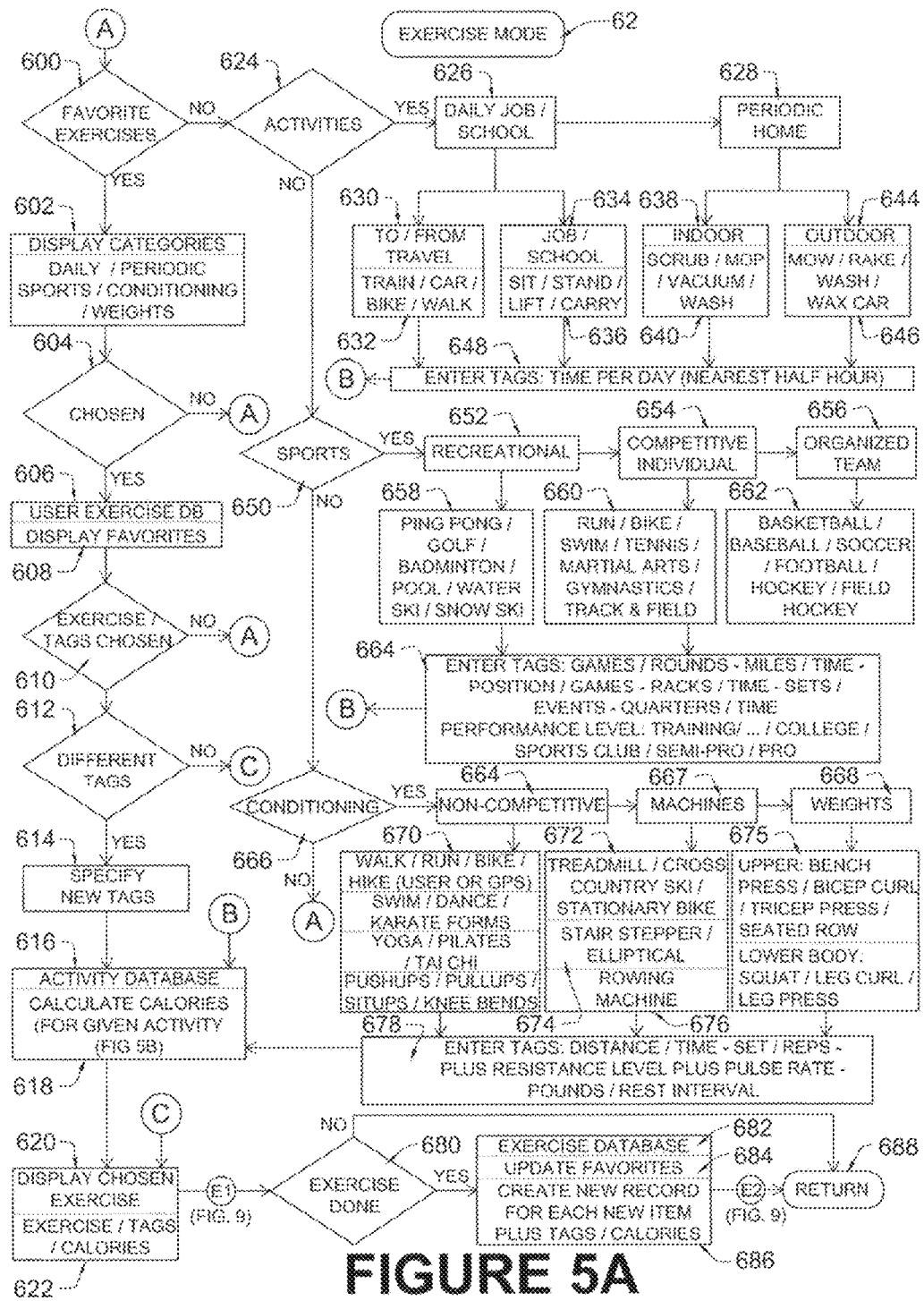
FIG. 5A is an illustrative flowchart for the system Exercise Mode depicting an exemplary implementation of 4 different ways the user can access his/her Exercise DB to view/modify its contents or add new exercises to the DB as he/she performs them.

FIG. 4A Food Mode: FIG. 4A shows an illustrative flowchart of an exemplary implementation depicting the steps involved in acquiring food consumption data in the system "Food Mode." Entry into this mode is triggered by the user selecting the Food Mode icon (56) in the mode selection display shown in FIG. 2B1, which in turn triggers the display of multiple food icons at the beginning of food mode processing (500). In this example, the display food icons processing (500) results in the display of the following illustrative food mode icons: "Favorite Foods" (502), "Restaurant Menu/Diet plan" (504), "User Voice Input" (506), and "Phone Picture Input" (508). The circled nodes "A," "B," and "C" in the center of FIG. 4A define iterative branch points back to blocks 502/544/560, respectively.

Initially, a check is made at block 502 to poll for the user selecting his/her "favorite foods" icon. As explained above for FIGS. 3A-3C, during the creation of a user profile, the user generates entries in the system Food DB that identify his/her favorite meals and/or favorite individual foods/snacks/drinks. This enables the system to acquire a baseline snapshot of the user's current eating inclinations and simplifies the user's future data entries. Each favorite food entry is stored locally (e.g., in memory 15 of the user's mobile computing device 1) and, in illustrative implementations, remotely at server 14.

If the check at block 502 reveals that the "favorite foods" icon was selected, the routine displays the various food categories (510) described above for FIGS. 3B-3C which, in this example, include breakfast, lunch, dinner, snacks, and drinks (512). A check is then made at block 514 to determine whether a food category has been chosen. If a category has not been chosen, the routine branches back to node A and displays the above-identified four icons.

If the check at block 514 reveals a category has been chosen, then the user food database (516) is accessed to, for example, obtain the user's favorite foods for breakfast, assuming the "breakfast" category was chosen. The user's favorite foods for breakfast are then displayed together with the frequency of consumption (518). The user may, for example, select favorite breakfast No. 1, (which may, for example, consist of one cup of Cheerios with whole-grain and 1/2 cup of skim milk), whereupon the associated tag information is displayed with associated color codes. Such tag information includes nutritional information (such as 140 calories, 2 grams of total fat, 160 mg of sodium, 1 g of sugar, etc.) that is accessed from Nutrient DB (566), as explained below.

It is noted that, every time the user eats a given food item, that item is added to the favorites list, together with an indication of the number of times such food has been consumed. By tracking the number of times an item is eaten, the system is able to rank favorites based on the user's frequency of eating that food item over time.

In illustrative implementations, the system operates to recommend healthier foods to a user. In such implementations, by way of example only, after a user has selected a RED food such as "rib roast," the system encourages the user to "step up the ladder" at least one rung by selecting a healthier alternative that is the next highest up the ladder of related foods, such as described in the exemplary Meat Ladder shown above. This healthier alternative is added to the user's "favorites" list in a highlighted fashion (e.g., displayed higher up the favorites list with a higher-level color code indicating a "healthier choice" than the RED color-coded rib roast) with a frequency count of "zero", until the user selects the recommended food which raises the count to "one". However, the presence of the food in the user's favorites list serves to encourage later selection by the user.

Turning back to the flowchart in FIG. 4A, a check is then made at block 520 to determine whether the user has chosen a both a food and quantity to be eaten. If the user has not made both selections at block 520 in a predetermined time period, the routine branches back to node A.

If the user has chosen a food and quantity as determined at block 520, a check is then made at block 522 to determine whether the user has selected a different add-on than the original favorite (if any). If the user has not selected a different add-on at block 522, the routine branches to node C at block 560.

If the user has decided to add a different add-on, such a new or additional add-on is then specified at 524 so that data can be accumulated for a new food record. For example, if the user had selected a meal including ham and eggs with the add-on "honey" on the ham, the check at block 522 gives the user an opportunity to select a different add-on for the ham and eggs at 524 such as "apple sauce". In an illustrative embodiment, the system provides an open-ended list of alternative add-ons for each food selected that is augmented by each new add-on declared by the user. Alternatively, the user may identify the add-on by voice input, as described earlier. The user's selection may in an illustrative embodiment be confirmed by a display to the user of the selection made, such as by a textual display of "apple sauce." In an illustrative implementation, the newly-selected add-on is next attached to the food item as a tag, as shown in FIG. 3B.

Once an add-on has been specified by the user or, if the user does not include a different add-on, the routine branches to block 560 at node C. As indicated at block 560, the chosen foods are displayed as a tentatively selected meal, items and add-ons, reflecting the user's selections (562). The meal referred to in block 562 is an aggregate of all the items constituting the meal. Furthermore, each item may have its own separate add-on (e.g., a sauce, dressing, butter, etc.).

In an illustrative implementation, the meal itself, each of the items in the meal. and each add-on has an associated color code that is displayed to inform the user as to, for example the relative healthiness of each meal/item/add-on to be consumed. In addition, in an illustrative implementation, a user may request to see the nutrient content of a food item/add-on selected, as indicated by the "show nutrient" check at block 564. Such a user selection may be prompted by, for example, a RED color code associated a selection, as would be the case with a rib roast or an ice cream sundae.

If the check at block 564 indicates that the user has chosen to see an item's nutritional content, the system then accesses the Nutrient Database (566) which displays all the food nutrients (and their quantities) associated with the item selected (at its quantity). All of this is displayed to the user together with associated color codes indicating the quality of nutritional content (568) via a call "F1" to the Calculate Calories utility subroutine shown in FIG. 9.

After the nutrient display, a check is made at 570 to determine whether the user has chosen to eat the food tentatively selected after reviewing the nutrient value and color code information displayed at 568. If the user chooses not to eat the food, the routine returns to the mainline in FIG. 2A (at 572).

If the user chooses to eat the food selected at 570, the user Food Database is updated at 571. If the item is a Favorite Food, the program (573) calls the Calculate Calories subroutine at "F1" (where the food's usage counter is incremented by one) and, upon its return, exits to the mainline at 572. If the item is not a Favorite Food, the program creates a new record for each item in the meal (including its associated quantity, add-on(s), and calories), appends the new record to the Favorite Food DB (with a usage count of zero), and makes the same "F1" call and final exit as above. In this manner, the system is able to sort and display the user's favorite foods according to the frequency he/she eats those foods.

In other words, any new food item, such as an old meal but with a new add-on, is added to the favorites list via creation of a new record—hence, the system creates a new record for each such item plus tags (575). The tags in this example identify the quantity of the food item consumed, together with any add-ons and their calories consumed, displayed separately on the same screen. The manner in which the total calories are monitored and tallied is discussed below in conjunction with FIGS. 7B and 9.

As shown in FIG. 4A, if the check at block 502 reveals that the user has not selected "favorite foods," the next check at block 504 tests whether the "restaurant/diet plan" icon has been selected. If so, the routine generates a display identifying the restaurants for which digitized menus are available (at 526) and/or a list of diet plans for which the system has a digitized compilation of acceptable foods contemplated by the plan (at 528).

The routine then checks at 530 whether a restaurant or diet plan has been chosen. If a restaurant/diet plan has not been chosen, the routine branches back to node "A" to poll for another mode selection. For convenience purposes, only restaurant menus are identified below without further reference to diet plans. It should be recognized that the description below equally applies to the user making selections from a diet plan, as discussed earlier with FIG. 2B2.

If a restaurant has been chosen at block 530, the routine accesses a restaurant database (532) and displays the menu for the selected restaurant (534).

A check is then made to determine whether the user has chosen a meal from the menu, or an identifiable a la carte item that is not associated with a meal from the menu (536). When a meal has been selected, the routine identifies the various items constituting the meal. In an illustrative implementation, such a meal is displayed with caloric information and with nutritional values associated with each of the meal items—including, e.g., main entree, plus side dishes, plus any add-ons, as delineated in FIGS. 3B-3C. The nutritional value of a selected meal is based on the total nutritional value of all the items constituting the meal.

If no meal or item is chosen by the user as indicated by the check at 536, the system branches back to node "A". If a meal or item has been chosen in accordance with the check at 536, then the routine checks at 538 whether the user desires to select more items. If so, the routine branches back to the displayed menu at 534. If no more items have been selected by the user, a check is made to determine whether additional add-ons to an item have been selected (540). If the user has chosen to modify the meal add-ons, then the user is asked to specify the add-ons (542) as explained previously in conjunction with blocks 522 and 524 in the "favorite foods" processing described above.

After add-ons have been specified by the user or, if no more add-ons were selected, the routine branches to branch point "C" at block 560 and processing continues as explained above in conjunction with the favorite foods processing at blocks 560 through 575 (including return 572). It should be understood that once the user selects a meal, e.g., at a restaurant, the selection made is added to the favorites list in the manner explained above and as indicated at block 575. Thus, the selection and data entry of the identical meal (at a later point in time) is significantly simplified for the user to choose and to enter due to the ever-expanding nature of the user's open-ended list of favorite foods.

If the user selects the "user voice" icon (506), the routine prompts the user to identify the food item to be consumed and the food quantity (544). The prompt may be verbal or displayed on the mobile computing device's display screen. The user may, for example, respond "chicken breast, 4 ounces." Upon the user articulating the food to be consumed, the routine analyzes and decodes the user's voice response (545). The routine then displays the identified food and the food quantity for user verification on, for example, the LCD display of the mobile computing device shown in FIG. 1 (547).

After the food and its quantity are displayed, the routine checks whether the user has confirmed that the system identified the food and quantity correctly (at 546). If the user indicates that the correct food was not displayed, the routine analyzes a 2nd and 3rd attempt to display the correct food and quantity. If the correct food is still not identified on the 3rd try (at 548), the user is prompted to type in the correct food and quantity (at 550). Prior to the 3rd try, if the correct food has not been identified, the routine branches back to node B and, once again, prompts the user to identify the food and quantity thereof at 544.

After the user types in the correct food, the system displays the food selected and its quantity at 552, where, in an illustrative implementation, the system also displays, for example, two foods that are equivalent in nutritional value to that chosen by the user. The two equivalent foods presented to the user are accessible from the Top Foods relational database schematically depicted in FIG. 2F. Thus, through a relational database implementation of the Top Foods database, a user's selection of walnuts may lead to an equivalent recommendation of almonds and pistachios. Moreover, in illustrative implementations, instead of presenting two foods that are merely equivalent to the user's selected food, the system may present foods that are related to the selected food, but even more highly nutritional, based on the needs of the individual user.

A check is then made at block 554 to determine whether the displayed food is the correct food. If so, the routine proceeds to display the chosen food at block 560 and processing continues in blocks 560 through 575 (including 572) in the manner described above. If the food is still not determined to be correct as a result of the check at block 554 an unknown food flag is set (at 556) and the routine returns (at 558) to the main routine in FIG. 2A.

As shown at block 508 in FIG. 4A, the system checks whether the user is entering food data via the camera on the smart phone or other personal computing device. A user may choose the camera-based food data entry mode under circumstances, for example, where packaged foods are used containing a barcode that, e.g., identifies the meal contained in the package and a wide range of nutritional information as described herein. In illustrative implementations, packaged meals may be generated together with barcodes that are tailored to the goals described in the subject specification.

If the phone picture icon 508 is selected, a check is then made to determine whether the user has chosen a packaged meal having a barcode (574). If so, the barcode is decoded and a Barcode Database (576) is accessed to find the food and its quantity (578). The food is then displayed at block 547 and processing continues as explained above, beginning at block 546 through 575 (including 572). In an alternative implementation, instead of using a Barcode Database 576, the system may utilize, for example, prepackaged lunches and dinners, each of which is identified with a barcode that may be a two-dimensional barcode such as a QR code. A QR code may be used to store and/or otherwise identify both the food consumed, portion size, and nutritional information including calories, fat, sugar content, and any other quantity the user, a physician or nutritionist desires to monitor.

If the check at block 574 indicates that a barcode package is not involved, the routine branches to a check at block 580 to determine whether the correct food has been identified. In this mode of operation, the user's mobile computing device camera is utilized to take a picture of a meal item or items. The digital image taken is used to determine the food and quantity based on an analysis of the picture taken. In an illustrative implementation, the image processing may be utilized in conjunction with specially designed plates of a known diameter having, for example, concave portions or built-in containers of a predetermined size that provide a known portion size of a meat, vegetable, and/or other food.

The image analysis reveals certain food identifying characteristic features of the food (582) and accesses a Food Feature Database (584) that correlates a given food with a set of food features. Such features include characteristics of the outer surface of the food and may include interior cross-section features of the food. With respect to the food outer surface, the routine looks for matches in the database with respect to food shape, surface textures, striations and food colors, and then matches such data to stored data relating to characteristics of various foods. Thus, the combination of various surface textures, striations, color and shape obtained from the digital image analysis is used to identify a particular food item. For example, a precooked hamburger or hot dog may be identified and indexed in the database based upon a combination of their visual characteristics of: 1) an identifiable round shape, 2) a predetermined surface texture, and 3) typical range of colors. Food quantity assessments (in ounces) are based on various visual characteristics (586) such as size and shape. Based upon such pattern matching data, the routine displays the best match for food and food quantity after considering, for example, the best 2 or 3 matches in the database (588). In an illustrative implementation, both the best match and the next best match for the digital food image may be displayed and the user may select the correct match, via, for example, a touchscreen selection.

A check is then made at block 590 to determine whether the displayed match with the mobile computing device's camera generated digital image for food and quantity identified the correct food and quantity. If the correct food is identified processing continues at block 560 as explained above, until the routine returns to the mainline routine at block 572.

If the correct food was not identified, the routine cycles back through blocks 580 and 582 and again accesses the Feature Database (584) to display the next best match for the photo once again checking for whether the correct food was displayed (590). If, after the third try (580), a correct match has not been found, the routine branches to node B and prompts the user to verbally identify the food and quantity (544). The previously described processing cycle then continues which, as described above, may ultimately prompt the user to type in the food and quantity (550). Processing continues as described above until the routine returns at block 572 to the mainline routine of FIG. 2A.

FIGS. 4B1 and 4B2 identify and illustrate the contents of the publically-available USDA Nutrient Database that may be utilized in whole or in part to implement the system Nutrient Database 566 in FIG. 4A. In an illustrative implementation, the nutrient values illustrated in FIG. 2D are accessible via the publicly-available National Nutrient Database, maintained by the Nutrient Data Laboratory of the USDA (Release 25, September 2012), or a subset thereof.

FIGS. 4B1 and 4B2 show for each identified nutrient number, the nutrient name and the number of foods in the database that contain it—e.g., for nutrient number 208, the USDA database provides the number of calories (energy) contained in 8,194 foods.

The USDA DB identified in FIGS. 4B1 and 4B2 includes nutrients that are generally self-explanatory, including most of the Macronutrients and Micronutrients delineated in FIGS. 2D1 and 2D2, respectively—however, for clarity, the common name/mnemonic for several nutrients has been added. It is also noted that the USDA DB includes total lipid (fat) information @ nutrient #204 (found in all 8,194 foods) and that, for clarity here, this "fat" category is later broken down into its constituent "Fatty Acid" subcategories, as follows:

- Saturated Fatty Acids (SFAs) @ #606, then non-sequentially through #654
- Mono-Unsaturated Fatty Acids (MUFAs) @ #645, then sporadically through #859
- Poly-Unsaturated Fatty Acids (PUFAs) @ #646, then sporadically through #858
- Trans Fatty Acids (TFAs) @ #605, plus #693 and #695

FIG. 4C includes an illustrative side-by-side comparison of the nutritional content for foods that are unhealthy choices (center columns) versus foods that are healthy choices (right-hand columns). In the example shown in FIG. 4C, the nutrient, mineral, and vitamin content in "Seasoned Fries" from T.G.I. Friday's and a "Big Mac" from McDonald's is compared with Sockeye Salmon and Turkey Breast. Looking at the boldface highlights, the unhealthy food is rated "Red" for many nutrients (center columns) and the foods that are highly nutritious are rated "Green" for many more nutrients (RH columns). Hence, FIG. 4C illustrates how the illustrative implementations described herein and their associated color codes help a user recognize exactly why salmon and turkey are healthier choices, based on their superior levels of nutrients, minerals, vitamins, and essential amino acids, e.g.:

- WRT protein, the Sockeye Salmon/Turkey Breast provide 56 g/67 g, whereas the Seasoned Fries/Big Mac respectively provide only 9 g/26 g of protein
- WRT fats, the Sockeye Salmon/Turkey Breast are limited to 15 g/5 g, whereas the Seasoned Fries/Big Mac respectively provide 34 g/33 g of fat
- Far worse, WRT saturated fats, the Salmon/Turkey are limited to 2 g/1.3 g, whereas Seasoned Fries/Big Mac provide 6 g/14 g, which is the bane of the American diet
- Again worse, WRT sodium, the Salmon/Turkey have radically lower 295/219 mg, whereas Seasoned Fries/Big Mac have 842/1007 mg, another bane of today's diet
- As for hard-to-find Selenium (that is vital to activating Vitamin E as a catalyst), the Salmon/Turkey have 81/67 micrograms, in stark contrast to the negligible selenium found in Seasoned Fries/Big Mac, which have only 9/0 micrograms Additionally, FIG. 4C shows that Sockeye Salmon and Turkey Breast provide 18%-83% more than the recommended daily allowance (RDA) of the nine essential Amino Acids for an exemplary 220-pound man. Smaller individuals would require proportionately less of these 9 essential Amino Acids to meet and exceed their RDA provided by the very healthy sockeye salmon and turkey breast (e.g., half as much—110 grams—for a 110-pound woman).

FIG. 5A Exercise Mode: FIG. 5A is an illustrative flowchart delineating the sequence of operations involved in the "Exercise Mode." Entry into this mode is triggered by the user selecting the Exercise Mode icon (62) in the mode selection display shown in FIG. 2B1, Upon entry into the Exercise Mode in this illustrative implementation, the routine displays the following four icons: "Favorite Exercises," "Activities," "Sports," and "Conditioning." The user has the option of selecting any one of these four exercise modes.

The routine initially checks whether the user has selected the Favorite Exercises mode (at 600). If the check at 600 indicates it was selected, the routine displays the favorite exercises categories of daily, periodic, sports, conditioning, and weights (602) as previously described, for example, in conjunction with FIG. 3D. The routine next checks at 604 whether any of these categories was chosen by the user. If not, the routine branches back to node A to determine whether the user has selected an exercise mode other than favorites.

If the user has chosen favorites, the routine accesses the Exercise Database as illustrated in FIG. 3F (at 606) to display each of the user's favorite exercises from the chosen category, together with associated tags of, for example, frequency, duration, cycle, quantity, calories burned, and the associated color code as shown in part in FIG. 3E (at 608). The calories burned are calculated at 616 using the approach described below that calculates calories at 618 using, for example, the Calorie Coefficient Database shown in FIG. 5B.

The illustrative implementations contemplate a wide range of tags that are associated with various exercises, as shown for example in FIG. 3D. The exercise frequency tag defines frequency as times per workout or times per week. The exercise duration tag tracks the time of exercising in hours, minutes, and even down to seconds where necessary (e.g., for sprints and other quick-burst track events). The exercise cycle tag keeps track of repetitions and sets for quick-burst events. The exercise quantity tag tracks pounds in weightlifting exercise and distance in a walking, running, biking or swimming context. The associated "calories burned" tag is ultimately calculated for every chosen exercise of a measurable duration and quantity (e.g., time and distance and/or sets and pounds).

The routine next checks at 610 whether the user has selected a favorite exercise together with its associated tags. If an exercise plus tags has not been selected, then the user has decided to exit out of the favorite exercises mode and the routine branches back to node A. If the user has selected an exercise as indicated by the check at block 610, then the routine checks at 612 whether the user has elected to modify the tags associated with the exercise. For example, the user may have decided to modify the frequency, duration, cycle, or quantity associated with the selected exercise. A user may increase, for example, the reps for a bench press from 6 to 10 reps, or the weight from 100 to 150 pounds, thereby indicating a change in the "cycles" or "quantity" tag shown in FIG. 3E; or the user may increase the time for a run from 1 to 2 hours, or the frequency from 2 to 3 times a week, which similarly changes the "duration" or "frequency" tag.

If the check at block 612 indicates the user decided to modify one or more of the tag parameters associated with the exercise, the user must next specify the new tags (at 614). If a different tag has not been entered, as indicated by the check at 612, the old exercise record remains unchanged and the routine branches to node C to display the original favorite exercise, tags and calories that will be burned upon completion of the exercise. Since no new tag has been selected, the originally-calculated calories burned and the original color code still apply to the user's chosen favorite exercise. Otherwise, if a new tag has been specified at 614, the routine proceeds to calculate calories burned (at 616). The calories burned is calculated by multiplying the user's body weight by a calorie coefficient for a given activity (at 618) as is described in detail below.

FIGS. 5B1 and 5B2 delineate an illustrative portion of an activity database based on calories per user activity for an exemplary user. The database was excerpted from the government-funded database published in the latest "Compendium of Physical Activities" by Ainsworth et al. (2011), as updated by Arizona State University in August 2012, which is hereby incorporated herein by reference. As shown in the database excerpts in FIGS. 5B1 and 5B2, the database provides an associated calorie coefficient for the exemplary user for a 30-minute timeframe across a wide range of activities. The calories burned during the identified activities are calculated by multiplying the user's body weight times the identified calorie coefficient.

The illustrative database shown provides calorie burned data for an exemplary user identified in FIG. 5B1 as a healthy, large-frame 6' 3" American male, age 25 who weighs 200 pounds. As set forth at the top of FIG. 5B1, the data shown for an exemplary 200-lb 6'3" male may be modulated by the identified percentages (e.g., per pound, per inch, per year, etc.) to embrace a wider range of users depending upon the user's weight, height, age, and gender. Using these and similarly-patterned clusters of percentages for other weight ranges centered, for example, at 80/110/150/250/300 pounds, a stepwise-linear Activities Database has been developed for a comprehensive range of users from the "Compendium of Physical Activities" (cited above), as will be appreciated by those skilled in the art.

As shown in FIGS. 5B1 and 5B2, activities are characterized by various parameters that further qualify the activity by specifying, for example, resistance, speed, or load level associated with the activity. Examples of qualifiers for an activity of carrying a load upstairs include carrying a load of 1 to 15 pounds upstairs, carrying 16 to 24 pounds upstairs, etc. For the activity of bicycling, illustrative qualifiers are leisure cycling speeds of 5.5 mph and 9.4 mph. Similarly, qualifiers for jogging, running, walking include a range of different speeds in miles per hour which reveal a non-linear increase in calories burned as speed is increased. In this illustrative DB excerpt, various universally popular categories of activities are walking, running. swimming, biking, gym, and sports The database shown in FIGS. 5B1 and 5B2 may be used to encourage users to step up from a minimally strenuous exercise such as walking at 2 mph to burning more calories by walking at 2.5 mph, and then 5 mph. Similar to nudging a user to step up a "Meat Ladder" from rib roast to light turkey meat (as described above) to eat additional more nutritious food with less calories, a user may be encouraged here to step up an "Exercise Ladder" by advancing through stages of walking faster from 2 to 2.5 mph, then running at 4 mph, at 6 mph, up to 7 mph, to get more aerobic exercise and burn more calories.

In illustrative implementations when a user changes an exercise tag such as those shown in FIG. 3E, the number of calories burned during exercise likewise changes. Such is evident from the calorie coefficient database shown in FIG. 5B1 by observing the difference in the calorie coefficients (per 1/2 hour) between carrying a 1 to 15 pound load upstairs to carrying a 25 to 49 pound load. Since the calories burned equals the body weight times the calorie coefficient, the calories burned (per 1/2 hour) for a 200-pound male is 219 calories carrying a 1 to 15 pound load upstairs versus 350 calories carrying a 25 to 49 pound load upstairs.

Turning back to FIG. 5A, when an exercise tag changes, the calculated calories burned will likely change and a new trial record must be created (at 618) for potential storage in the Exercise Database, as will be explained in more detail below in conjunction with blocks 682, 684, and 686.

Figure 9:
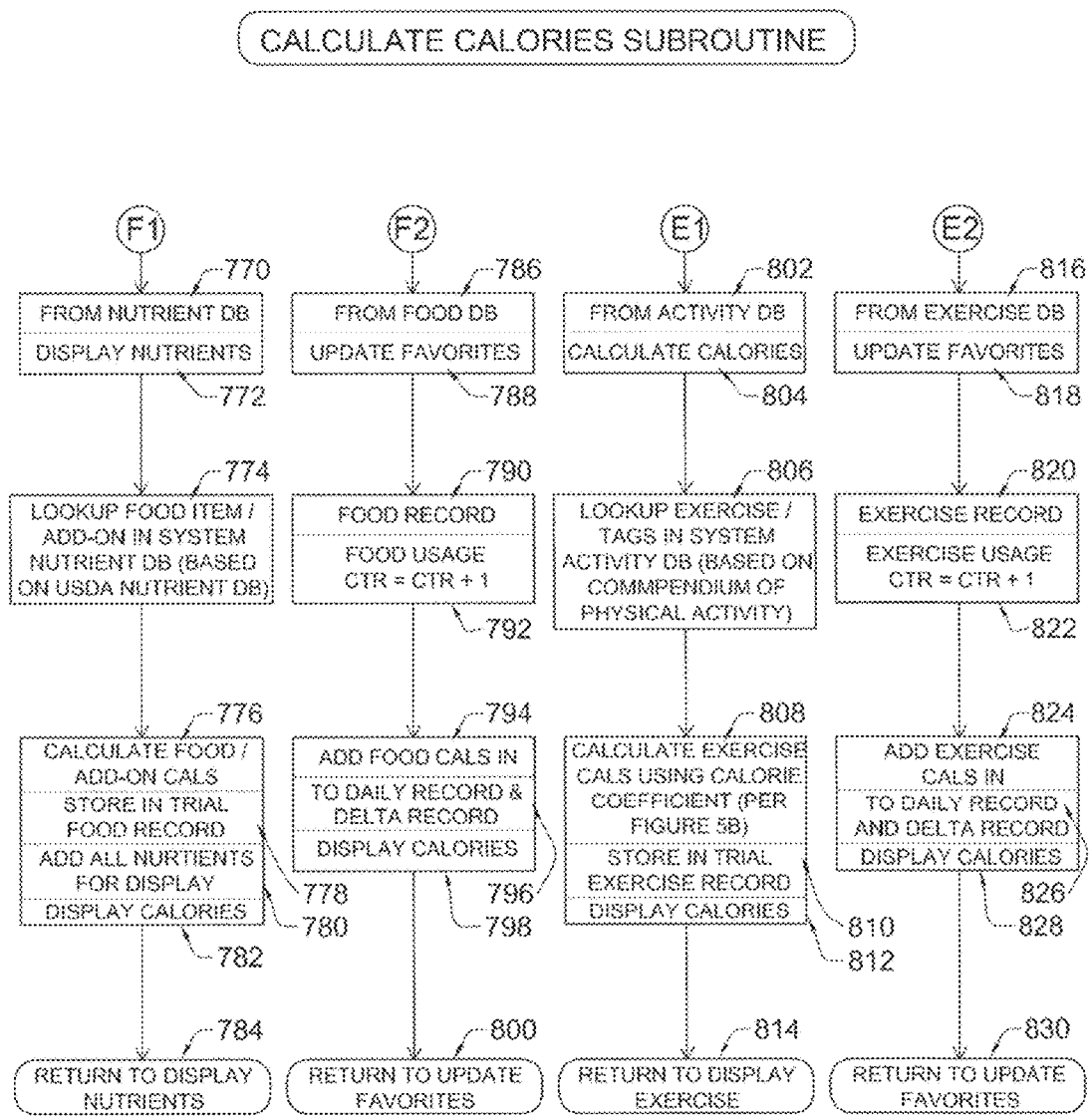
FIG. 9 is an illustrative flowchart of a utility subroutine dedicated to performing lookups on the system Nutrient DB or Activity DB, in order to calculate calories associated with food or exercise, respectively, and if appropriate, to update the Daily/Delta Records of FIGS. 7B3 and 7B4, respectively.

Thereafter, the system displays the chosen exercise together with all the associated tags as described above (at 620) including the calories burned for the given exercise activity (at 622) via call "E1" to the Calculate Calories utility subroutine (shown in FIG. 9). The calories burned values for a given exercise activity must be tallied to define the user's total calories burned during all exercise activities during any given timeframe chosen to be monitored, e.g., daily, aggregated to weekly, next aggregated to monthly, etc.

The routine then checks at 680 whether the user has actually completed the exercise or is merely contemplating performing it. If the user does not perform the chosen exercise, the routine returns to the mainline routine in FIG. 2A (at 688). If the user performs the chosen exercise as indicated by the check at block 680, the Exercise Database is updated (at 682), in a manner described further below, by updating the favorites (at 684), creating a new record for each item plus associated tags and calories (at 686) by calling the Calculate Calories utility subroutine at FIG. 9 (which also increments the record's usage counter) via the "E2" call following block 684. Thus, if a previously-stored favorite exercise is modified by, for example, increasing the pounds utilized during weightlifting, a new record is created in the user's Exercise DB to reflect the change in the tag quantity, which in turn results in a modified "calories burned" output. Any new exercise performed by the user in any of the exercise modes triggers appending the trial record discussed above to the user's open-ended list of favorite exercises to enable fewer user data entry operations.

If the favorite exercises icon was not selected at block 600, the routine checks whether the "Activities" mode (624) was selected for entry of activities that occur on a daily basis (626) or on an as-needed periodic basis (628).

In an illustrative implementation, if the Activities exercise mode is selected at block 624, under a "Daily" heading, two daily icons are displayed: To/From Travel (630) and Job/School (634). Additionally, under a "Periodic" heading, two periodic icons are displayed: Indoor (638) and Outdoor (644).

If the "Daily" To/From Travel icon is selected, a user will have a choice of selecting a range of travel options including, for example, train, car, bike and walk. Thus, in this fashion, a user receives credit for calories burned, for example, while bicycling or walking to work as a daily activity. In an illustrative implementation, the user is informed not to redundantly enter walking or bicycling to and from work as both a daily activity and, for example, a conditioning exercise so as to duplicate the calories burned totals entered into the system. Alternatively, while the system registers that travel to and from work or school is done by car, only a minimal amount of calories burned is attributed to such minimal activity.

Additionally, in the example shown in FIG. 5A, if the daily Job or School icon is selected, such common activities as sitting, standing, lifting, carrying, etc. are displayed to the user (636). Thus, in this fashion, users with physically strenuous jobs requiring extensive lifting and/or carrying, such as FedEx delivery, trash pickup, home building, brick laying, etc., will be awarded full credit for their effort. Even users who stand at their job all day will get more credit than the minimal credit for those who, for example, sit at their desk.

Similarly, with respect to "Periodic" activities, if the indoor icon (638) is selected, the routine displays an array of periodic home activities such as, for example, scrub/mop floors, vacuum rugs, and wash dishes. If a user selects periodic home outdoor activities, an array of periodic home outdoor activities (644) are displayed including, for example, mow/rake grass, wash/wax car, mulch/weed garden (646). Although such common activities are often dismissed as mundane, users here will get full faith and credit for their extra diligence.

If any one of the icons 630, 634, 638, and 644 are selected and the user chooses an activity displayed as a result of selecting a given icon, the user then enters tags associated with the activity, as described above, defining the time per day, for example, to the nearest half hour (648). After the tags have been entered, the routine proceeds to node B at block 616 to calculate the calories burned and completes the processing described above with respect to blocks 616 through 622 and 680 through 688.

If the user did not select the Activities icon (624), the routine next checks whether the user has selected the "Sports" icon (650). If so, the routine displays a Recreational Sports icon (652), a Competitive Individual Sports icon (654), and an Organized Team Sports icon (656).

If the user selects the Recreational Sports icon (652), an array of recreational sports options is displayed to the user (658). For example, the user may select ping-pong, golf, badminton, pool, water skiing, snow skiing, etc. If the user selected Competitive Individual Sports icon (654), an array of competitive individual sports icons are displayed including for example run, bike, swim, tennis, martial arts, gymnastics, track & field, etc. (660). If the Organized Team Sports icon (656) is selected, an array of organized team sports is displayed to the user (662). For example, as shown in block 662, the user may select basketball, baseball, football, soccer, hockey, field hockey, etc. If the user has selected any of the sports activities shown in the open-ended lists represented in block 658, 660, or 662, depending upon the sports activity chosen, the user may add a wide variety of qualifying tag information tailored to the individual activities (664). For example, as indicated by the illustrative list below, a user may specify racks (pool), rounds or holes played (golf), miles run/elapsed time, games/sets/time (tennis), events (gymnastics), quarters/time of play (football), team position (e.g., running back, QB, pitcher, goalie), etc. Additionally, in an illustrative implementation, since calories burned are modulated on user performance levels, the routine asks the user to declare his/her involvement at one of the following performance levels: training, recreational, middle school, high school, college, sports club, semi-professional, professional, etc. After a tag entry by the user (664), the routine proceeds to calculate calories for the given activity at block 616 and to complete the processing at blocks 616 through 622 and 680 through 688.

If the Sports icon was not selected as indicated by the check at block 650, the routine next checks whether the user has selected the Conditioning icon (666). If it was not selected, the routine branches back to node A at block 600.

If the Conditioning icon was selected, icons for "Noncompetitive" Conditioning (664), "Machine" Conditioning (666) and "Weight" Conditioning (668) are displayed. If the user selects the Noncompetitive Conditioning icon (664), a wide array of noncompetitive activities are displayed for user selection. For example, the user is presented with an array of open-ended lists of such exercises, including walk, run, swim, bike, hike, climb, dance, karate forms, Yoga, Pilates, Tai Chi, etc. (at 670)—plus shadow boxing, skip rope, push-ups, pull-ups, sit-ups, knee bends, jumping jacks, alternating-leg lunges, etc. (also at 670) which are vital to properly warmup before any athletic exercise, especially weightlifting.

With respect to linear-motion activities such as walking, running, biking, hiking, and even swimming (with proper waterproofing), the user may initiate a GPS-based exercise mode (64) shown in FIG. 2B, where, for example, the distance traveled can be automatically tracked by the user. As indicated above, the GPS subsystem of a computing device (e.g., an iPhone) is utilized to track distance and to provide the exercise "quantity" tag. If GPS is utilized, the system acquires and stores user position coordinate information based on GPS data input to GPS receiver 5 via GPS antenna 7 shown in FIG. 1. In illustrative embodiments, mobile computing device 1 may be equipped with a pedometer 13 to provide an input relating to the number of steps taken by user. In addition to tracking the number of steps taken by a user over time, the pedometer input may be utilized by the system to provide an additional indication of calories burned and distance traveled as, for example, an independent backup check on distance traveled that was calculated from the GPS data. Furthermore, the pedometer input may be used to credit the user with exercise, for example, from running in place, running up/down steps, using a stair stepper machine, or other relatively stationary exercise where the user is not traversing a typical linear path. Moreover, the steps the user takes over a given time period in this fashion may independently be used to calculate the calories he/she burned during exercise.

In an illustrative implementation, after acquiring user position and/or pedometer data, the routine displays the user position together with progress data on the user's screen display. The progress data may, for example, include a wide range of data regarding the run including the distance traveled in real time, the pace of the activity, whether the pace is faster or slower than the average pace during the past week's exercise session, etc. In various implementations, the user (or a simulated "avatar" of the user) may be visually depicted traversing the path defined by the GPS data while engaged in the walking, running, or bicycling activity. In this fashion, a user may view his or her position in real-time during, for example, a walk, run, or bicycling exercise routine through the city or suburban path chosen by the user, while, for example, listening to selected music, audio books or other entertainment or educational media. In certain embodiments, the pace of the user may be monitored and a simulated "personal trainer" may prompt the user to, for example, adjust the pace (up or down) as appropriate based upon age and health-related criteria. In an illustrative implementation, the user is prompted to provide a walk, run, or bicycling activity start signal to, for example, indicate that the current exercise is a walk, run, or bicycling exercise session and to signal that the exercise session has commenced.

Additionally, in an illustrative implementation, with respect to, for example, non-competitive activities, the system determines a wide range of parameters regarding the activity including various pace-related parameters, the distance traveled since the beginning of the exercise and the length of time of the exercise. In an illustrative implementation feedback is provided to the user to, for example, indicate that the 30-minute run was faster than his/her last run, or the fastest run of the week based upon stored historical exercise data. In addition, in an illustrative implementation, information regarding the speed of the run and the calories burned during the run are displayed to the user.

Figure 10:
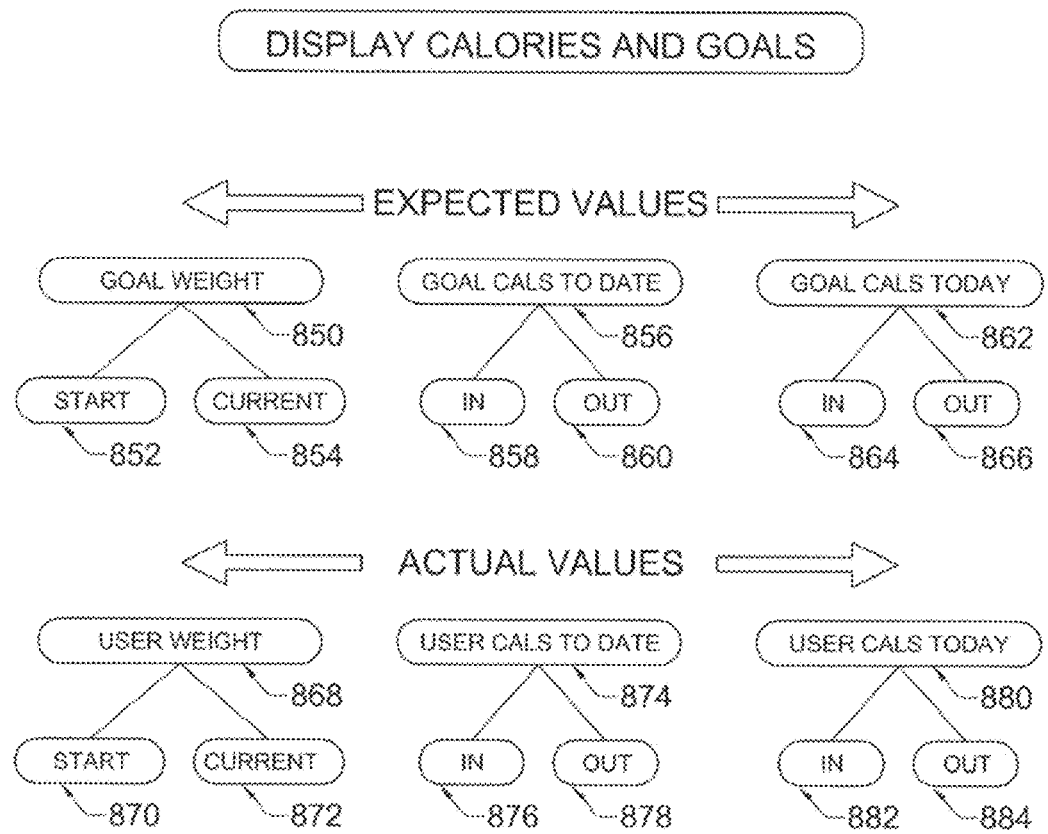
FIG. 10 is an illustrative format for displaying calories to the user as pairs of "expected values" versus "actual values" in 3 areas: net calorie accrued today, net calories accumulated from day one to date, and goal weight vs. actual weight, using the Daily/Delta Records of FIGS. 7B3 and 7B4.

In certain illustrative embodiments, assuming the exercise took place after lunch, the system may, for example, display to the user the amount of calories that may be consumed at dinner to meet current goals, based upon the calories consumed at breakfast and lunch minus the calories burned during the exercise, as is conveniently tracked via the running display counter of cumulative "User Cals Today" shown in FIG. 10.

If the user has selected the Machine Conditioning icon (666), an array of exercise machines are displayed to the user that may be selected (672). For example, the system provides the user with the ability to select treadmill, cross-country ski, stationary bike, stair stepper, elliptical, rowing machine, etc. In an illustrative implementation, if the system does not already have stored information regarding the machine being utilized, in an illustrative implementation, a user prompt is generated for the user to input the specific brand of exercise equipment being used. Additionally, if the machine generates an array of workout information, the routine may capture data from identified equipment by, for example, prompting the user to verbally indicate the data output from the equipment such as the amount of calories burned, the distance traveled, the level of difficulty or resistance, and other significant data relevant to defining and/or delimiting the machine-guided exercise. In certain illustrative implementations, the user may capture a displayed array of output data using the computing device's camera. Many machines provide a display of identified data such as calories burned, miles traveled, etc., that may be captured via a camera, via verbal user input, or via a wireless communication link with compatible exercise equipment that has been expressly designed to transmit data to, for example, smart phones.

If the user selected the Weight Conditioning icon (668), an array of weightlifting exercises are displayed to the user that may be selected (677). For example, as shown in block 677:

- with respect to upper body weightlift exercises, the user can select, inter alia: bench press, overhead press, incline press, dumbbell press, tricep press, tricep press-downs, bicep curls, wrist curls, standing cable pulls, seated rowing, etc.
- With respect to lower body weightlift exercises, the user can select, inter alia: squats, weighted lunges, leg curls, leg extensions, weighted back extensions, calf press, seated leg press, incline leg press, vertical leg press, etc.
- As with the other exercise categories above, there is an open-ended list of weightlift exercises dedicated to each motion of the torso and each limb (forward/back, up/down, and CW/CCW rotation as appropriate),
- This includes exercises for both limbs (arms/hands, legs/feet) working together and independently isolated, which can be adapted to the user's unique needs (e.g., a weak limb or one with limited range of motion, as declared by the user)
- This also includes sequentially-paired exercises for opposing muscle groups (e.g., chest/upper back, stomach/lower back, biceps/triceps, quads/hamstrings, thigh subduction/abduction, forward/reverse wrist rolls, etc)

For most weightlifting exercises, there are four parallel options that each have their advantages and disadvantages, which include:

- Free Weight Barbells: working with a barbell provides a real two-hand (or two-leg) challenge that quickly reveals any weakness in one limb or the other —hence, a lifter gets the best advantage out of maintaining RH/LH equilibrium —however, at higher weights, presses/squats require a spotter for safety reasons
- Free Weight Dumbbells: working with one or two dumbbells provides the best mechanism to strengthen the inevitable weaker RH or LH arm/shoulder/hand —however, they only benefit the arms and can still harm a user at higher weights
- Weightlifting Machines: working with machines provides the most convenient way to emulate most free weight lifts but without the instability or the spotter —however, it is much more difficult to isolate/strengthen a weaker limb, and without the pressure of maintaining weight equilibrium, the torso gets left out
- Isolated versus Combined Lifts: since two hands are always better than one, most users can lift a barbell with much more than twice what either arm or leg can lift separately with dumbbells or machines, mostly because the torso helps—however, over time, isolated lifts strengthen the weak side of a combined lift so that both lifts are essential to optimizing overall strength of the entire body
- Therefore, for any given weight exercise, the system offers all 4 options above, side-by-side on the user screen, wherever practical and/or possible, taking into account a 20% differential from free weight levels up to higher machine levels, using back-to-back opposing-muscle lifts to optimize available blood flow, and the user's unique needs (e.g., a weak limb and/or with limited range of motion)

After the selection of the non-competitive, machines, or weightlifting conditioning exercise, the user enters any of a wide array of tags (678). Such tags may include distance, time, sets, repetitions, etc., depending upon the activity selected. As explained above, the distance information and time information may be provided by the system when operating with the use of the computing device's GPS subsystem. Additionally, resistance levels may be entered with respect to the various machines identified. Further, with respect to weightlifting, the user may, for example, enter pounds, pulse rate, and rest interval information.

After the tags have been entered (678), the routine proceeds to node B at block 616 to calculate the calories burned and completes the processing as described above with respect to blocks 616 through 622 and 680 through 688.

Food and Exercise Recommendations—Stepping Up the Ladder

In certain illustrative implementations, it is contemplated that the system described herein will play an active role in encouraging users to eat and exercise in a healthier fashion than they have done in the past. With respect to both healthy food intake and optimum exercise routines, many individuals benefit from a highly structured system in which some of the individual's food and exercise choices are selected for them. It is contemplated that certain illustrative implementations will advantageously utilize food and exercise ladders of the type described herein to encourage users to "step up the ladder" so that they can find out for themselves the joy of eating and exercising in a healthier fashion over time.

For example, the Meat Ladder shown above illustrates how the system can make a user healthier by way of better nutrition:

| MEAT LADDER | OBESE WEIGHT MAX =====> MIN | OVERWEIGHT MAX =====> MIN | HEALTHY BODY FRAME* MAX =====> MIN | | |
|---|---|---|---|---|---|
| Best GREEN Nutrients | Highest ==> Protein/Fiber/Omega-3/HDL/Antioxidants/Vitamins/Minerals/Potassium Lowest ==> Calories/Double Sugars/LDL/Saturated Fats/Trans Fats/Sodium | | | | |
| 6> BLUE | | | (3 ounce serving for all meats) 98 Cals/20.1 g Protein/1.3 g Fat ==> | | light Turkey |
| 5> GREEN | | | 97 Cals/19.7 g Protein/1.3 g Fat ==> | light Chicken | |
| 4> LIME | | | 106 Cals/17.1 g Protein/3.7 g Fat ==> | dark Chicken | |
| 3> YELLOW | | | Round Steak | <== 121 Cals/18.4 g Protein/4.7 g Fat | |
| 2> ORANGE | | Sirloin Steak | <== 171 Cals/17.3 g Protein/10.8 g Fat | | |
| 1> RED | Rib Roast | <== 260 Cals/14.1 g Protein/22.2 g Fat | | | |
| Worst RED Nutrients | Highest ==> Calories/Double Sugars/LDL/Saturated Fats/Trans Fats/Sodium Lowest ==> Protein/Fiber/Omega-3/HDL/Antioxidants/Vitamins/Minerals/Potassium | | | | |

*This is the MAX ==> MIN range for a small/medium/large frame Healthy User

This Meat Ladder chart illustrates an illustrative system strategy of boot-strapping the user at any diet level—e.g., obese RED==>healthy GREEN—up the ladder, one step at a time—from the fattening RED rib roast or ORANGE sirloin steak, up the ladder toward the ultimate GREEN light chicken or BLUE light turkey. Moreover, in illustrative implementations, there is a similar 5-color food ladder for each one of the 60 Open-Ended Lists by which the system can improve a user's diet, one step along one ladder at a time.

Similarly, the exercise ladder shown above illustrates how the system can make a user healthier by encouraging better exercise or at least some exercise:

| WALK/RUN LADDER | OBESE WEIGHT MAX =====> MIN | OVERWEIGHT MAX =====> MIN | HEALTHY BODY FRAME* MAX =====> MIN | | |
|---|---|---|---|---|---|
| Best GREEN Parameters | Highest ==> Healthy/at or near Ideal Weight/toward Max Heart Rate (see FIG. 3G) Modulators ==> Height vs. current Weight/Gender/Age/Obesity level/Fitness level | | | | |
| 6> BLUE | | | 40 yards @ 6 seconds (or) 100 yards @ 12 seconds ==> | | Fast Sprints |
| 5> GREEN | | | 1 mile @ 6 minutes (or) 5 miles @ 35 minutes ==> | Fast Run | |
| 4> LIME | | | 5 miles @ 50 minutes ==> | Slow Run | <== 1 mile @ 9 minutes |
| 3> YELLOW | | | Slow Jog | <== 1 mile @ 11 minutes | |
| 2> ORANGE | | Walk/Jog | <== 1 mile @ 15 minutes | | |
| 1> RED | Slow Walk | <== 1 mile @ 30 minutes | | | |
| Worst RED Parameters | Highest ==> bad Health profile/Obese now/Obese 5-10 years ago/below Min Heart Rate Modulators ==> Height vs. current Weight/Gender/Age/Obesity level/History/Health | | | | |

*This is the MAX ==> MIN range for a small/medium/large frame Healthy User

This Walk/Run Ladder illustrates the system strategy of boot-strapping a user at any exercise level—e.g., obese RED==>healthy GREEN—up the ladder one step at a time—from the slowest RED walk time or ORANGE Walk/Jog time, up the ladder toward the GREEN fast run time or ultimate BLUE fast sprint time. This Run/Walk Ladder illustrates how the system can make a user healthier. In an illustrative implementation, there is a similar 5-color exercise ladder for each one of the 60 Open-Ended Lists by which the system improves user exercises, one step along one ladder at a time.

Regarding food intake, in an illustrative implementation, the system provides the user with a scheduled diet to consume for a prescribed time period. In an illustrative implementation, the user is provided with (e.g., by display or email) a "Grocery List" of foods to be obtained at the market, for example, for consumption during the following one week or two week time span. The grocery list is based on a projection of foods needed to create 3 meals, snacks and drinks for each day based on the user profile information including the user's favorites list and the user's selected diet plan with caloric intake projected over time.

As indicated above, in an illustrative implementation, the system operates to recommend healthier foods to a user as follows. After a user has selected a food such as "rib roast," the system encourages the user to "step up the ladder" by selecting a healthier alternative that is next highest up the ladder of related foods such as described in the meat ladder above. In this implementation, the healthier alternative is added to the users "favorites" list in a highlighted fashion ((e.g., displayed higher up the favorites list based upon a displayed color code indicating a "healthier choice" than the red colored rib roast) with a frequency count of zero indicating that the user has not selected the food at this particular point in time.

In illustrative implementations, the grocery list for the next two weeks is based at least in part on healthier entries added to the user's favorites list to encourage the user to step up the ladder. Thus, the list of foods to purchase for the next week would be based on what was consumed the previous week but also factors in the step ladder by adding foods to purchase for the next week including some foods on the next rung up the ladder. Since many people do better during dieting when some of their choices are made for them, the system prepares a daily diet menu that the user can follow and creates a "Grocery List" so that the user will know what foods and amounts to obtain such that the daily menus can be followed. In such an approach, planned visits to restaurants may be factored into the foods needed calculations for the next two weeks.

These healthier entries may be automatically added to the grocery list based upon any of a variety of reasonable approaches. For example, the generated grocery list may be based in large part on the favorite meals recently consumed by the user as indicated by the Food Database 571 (FIG. 4), and be based in part on replacing a small percentage of the user's favorite choices with healthier alternatives as indicated by the relevant food ladder. In one certain implementation, if, for example, the user has had difficulty achieving weight loss goals, the next generated "grocery list" should include an increasingly larger number of healthier alternative selections that are chosen to aid progress towards goal attainment.

In certain illustrative implementations, a similar approach is also applied to exercise by having the system generate an "exercise prescription" for the user. In such an implementation, the system projects, for example, a two week user's exercise plan by identifying the exercise activities that the user should be trying to do over a future period of time. Such a projection would be based upon the user's current exercise favorites (e.g., compared to his/her original Top 5) and on the caloric expenditure requirements determined by the system based on the user's profile and goal data.

In such an implementation, the system generates a plan that the user sees over time (e.g., by display or email). A chart may be generated that defines the recommended exercise plan for a projected 2-week month, or 6-month period, as illustrated for an exemplary overweight American male in FIG. 7A.

As indicated above, the database described in conjunction with FIGS. 5B and 5C may be utilized to generate the exercise prescription to encourage users to step up from a minimally strenuous exercise such as walking at 2 mph to burning more calories by walking at 2.5 mph, and then 5 mph. Similar to the desirability of a user progressing through a meat ladder from rib roast to light turkey to eat more nutritionally with less calories as described above, a user may be encouraged to step up the "exercise ladder" by progressing through walking faster from 2 to 2.5 mph to running at 4 mph and then 5 mph, or even 6 mph.

As with the food entries, the healthier exercises may be automatically added to the exercise prescription based upon any of a variety of reasonable approaches. For example, the generated prescription may be based in large part on the favorite exercises recently performed by the user as indicated by the Exercise Database 682 (FIG. 5A), and be based in part on replacing a small percentage of the user's favorite choices with healthier alternatives as indicated by the relevant exercise ladder. In one implementation, if, for example, the user has had difficulty achieving weight loss goals, the next generated "exercise prescription" should include an increasingly larger number of healthier alternative selections in light of the user's profile that are chosen to aid progress towards goal attainment.

In this fashion, the user may plan for exercise by knowing that he/she would need to set time aside, for example, four, 30 minute periods on the elliptical this week and four, 40 minute periods next week. Such an "exercise prescription" generated in light of one or more exercise ladders will change dynamically based on how well the user did during the previous timeframe.

Figure 6A:
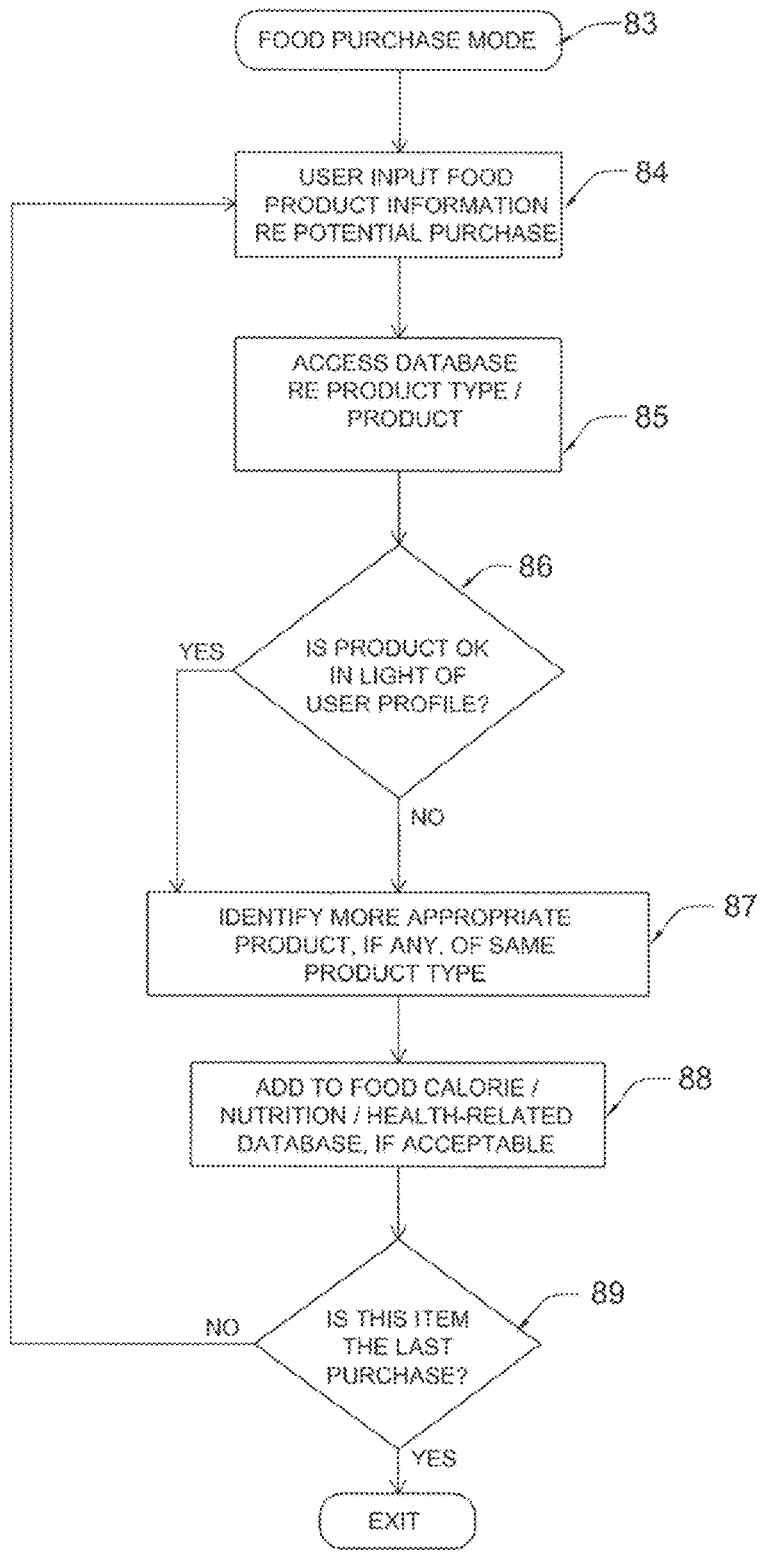
FIG. 6A is a flowchart delineating the sequence of operations performed in an illustrative implementation during food purchase mode at a grocery store or restaurant.

FIG. 6A is a flowchart delineating the sequence of operations performed in an illustrative implementation during the "Food Purchase" mode that may, for example, be utilized in a grocery store or restaurant environment. While the flowchart depicted in FIG. 6A is tailored to applications in a grocery store context, modifications for use in restaurant ordering of foods will be apparent to those skilled in the art particularly in light of the description below. As applied in a grocery store context, upon entry into the Food Purchase mode (83) in response to a user selecting the Food Purchase mode icon 60 shown in FIG. 3, the system prompts the user to input food product information. The user may, for example, verbally indicate that "Honey Nut Cheerios" has been selected for purchase (84). In a restaurant context, a user will be prompted to identify the name and location of the restaurant and identify the entree selected.

The routine then, using speech recognition software 8, decodes the input product information and accesses the server 14 database to acquire nutritional information regarding the product and any closely-related products (85). Similarly, in a restaurant context, in one illustrative implementation, the server 14 database stores menus and nutritional information data regarding selections from the menu in the users geographical area as determined by the mobile computing units GPS subsystem. The server 14 then accesses nutritional information regarding the user's selected entree and entrees that are in the same family of food selected by the user. In one illustrative example, if the user selects a fish entree, the system will access and display all available nutritional information regarding the selected entree and all other fish alternatives on that menu, together with their associated color codes, to inform the user of his/her immediate options to eat the worst RED 1$\Longrightarrow$5 best GREEN choices (if any are available).

As indicated at block 86, a check is then made to determine whether the product selected is acceptable in light of the user's profile. In the present example, if the user's profile indicates that the user is a diabetic, the system proceeds to identify a more appropriate product of the same product type (87). Thus, using the example of a request for Honey Nut Cheerios, the database in server 14 is accessed and the routine determines that at least two alternative products may be better alternatives since Honey Nut Cheerios has 9 g of sugar, whereas the original Cheerios has 1 g of sugar and Multi-grain Cheerios has 6 g of sugar. For a diabetic, the routine may only identify original Cheerios as an alternative. For a user without sugar-related problems, in this illustrative example, the routine would nevertheless display the original Cheerios and multigrain Cheerios as alternatives of the same product type. In addition, in certain implementations, basic nutritional information for each alternative may be displayed. As shown in FIG. 6A, whether or not the selected product is appropriate in light of the users profile, healthier alternatives are proposed. Analogous operations of presenting various menu alternatives may be performed in a restaurant context as will be appreciated by those skilled in the art.

Thereafter, the food purchasing mode routine adds the selected product/entree to the food caloric, nutritional and health related portions of the database associated with server 14, if the product/entree is acceptable for consumption by the user (88). Products/entrees which are identified as not being acceptable based on input from the physician's data processing center 20 shown in FIG. 1 will include products/ entrees that contain ingredients to which the user is allergic or are otherwise unacceptable in light of health-related profile information.

A check is then made at block 89 to determine whether the item selected is the last item to be purchased. If so, the routine exits. If other items remain to be purchased, the routine branches back to block 84 when user is again prompted to input food product information.

Figure 6B:
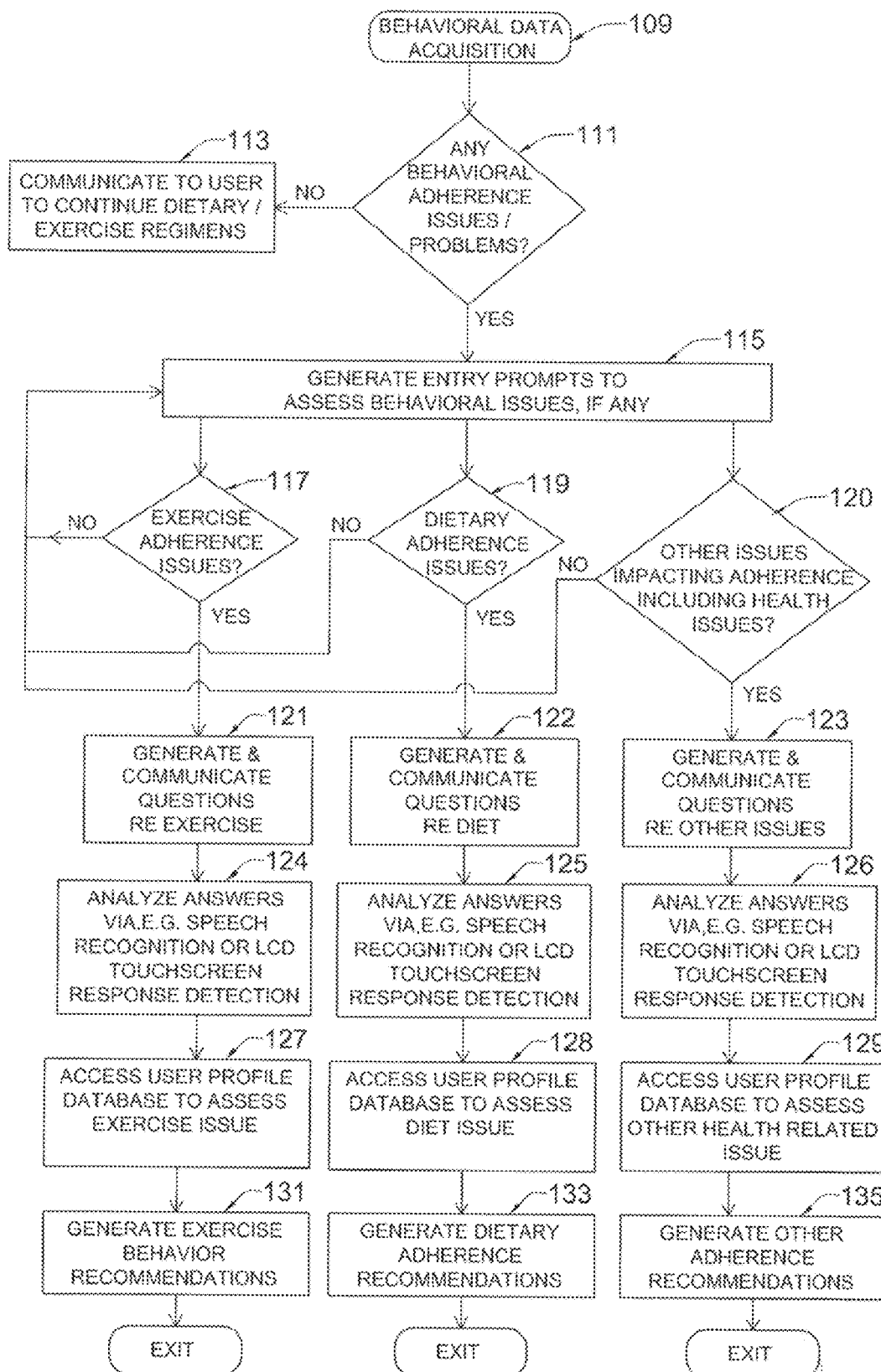
FIG. 6B is an illustrative flowchart delineating the sequence of operations involved in a behavioral data acquisition mode.

FIG. 6B is an illustrative flowchart delineating the sequence of operations involved in behavioral data acquisition. Upon entry into behavioral data acquisition processing (109), the mobile computing device 1 initially prompts the user to input whether the user is experiencing any behavioral adherence issues or any other problems adhering to the dietary protocol or exercise regimen or otherwise needs help of any kind (111). If the user fails to indicate any issues, the mobile computing device 1 prompts the user to continue his or her current behavioral and adherence regimen through a user (e.g., Iphone) display or digitally synthesized verbal message (113).

In an illustrative implementation, if the user's response indicates a behavioral issue, the mobile computing device 1 generates and displays a sequence of prompts (115) to elicit a response from the user identifying the area(s) of behavioral difficulty as being in a particular category or categories, such as dietary adherence, exercise adherence and/or other issues that impact adherence (including, but are not limited to, difficulties caused by symptoms from diabetes, chemotherapy, physical disabilities, etc.).

For each category in which an adherence issue is identified (117, 119, 120), the mobile computing device 1 generates and communicates in an appropriate sequence one or more questions specific to each identified category by LCD display and/or digitally synthesized verbal message (121, 122, 123). Although not represented in the simplified flowchart, as will be appreciated by those skilled in the art, once the system determines that no further adherence issues remain to be processed, the behavioral adherence mode processing ends.

If, for example, the user identifies a dietary behavioral adherence assessment problem, the system may respond with a series of questions and prompts such as: Are you hungry? At certain times? Are you feeling tired, stress, bored? Are you going long periods of time without eating? Are you eating too much at a particular meal time? Are you snacking in between meals?

If the user identifies that he or she is having trouble adhering to an exercise regimen, the system may respond with a series of questions such as: Are you having trouble finding time for exercise? Are you getting short of breath during exercise? Are you straining muscles during exercise?

The user responds to these questions via LCD display touch screen selection and/or speech input that is analyzed by speech analysis software 8 (124, 125, 126).

The mobile computing device 1 accesses the user profile and associated database(s) to assess exercise, behavioral, nutritional and other related data (127, 128, 129). In illustrative embodiments, mobile computing device 1 then displays results to the user pertaining to behavioral issues and provides feedback regarding the identified issues with, for example, suggestions to address the identified issues (131, 133, 135). An evaluation of the user's responses may lead to any of a wide range of dietary and exercise-related behavioral recommendations such as: "Add a piece of fruit at 4 pm", "Stay occupied with a project or activity after 8 pm", "Eat some protein with each meal," "Eat smaller portion meals every 3 hours," "Stop exercising if you feel faint and see your physician," "Slow down your run to a 11 minutes per mile pace," "Increase your distance run by 1/4 mile per day until you reach a distance of 3 miles," or step up one or more food and/or exercise ladders as explained in detailed above, etc.

In illustrative implementation, under circumstances where a user's issue suggests that the user is not sufficiently motivated to address his or her obesity or overweight condition, a wide range of motivational information may be displayed to the user. In addition to positive reinforcement in light of prior weight loss accomplishments documented by the system, may be displayed to the user to emphasize the significant increase in risk associated with being obese and/or overweight. An illustrative risk table of the type that may be displayed is shown in FIG. 6C, where the reticent obese user will discover that the traditional bane of Type 2 Diabetes for obese people at 1020% higher risk (than a healthy person) actually comes in at 2nd place behind Esophageal Cancer at 1520% higher risk.

In an illustrative implementation, a generated behavioral recommendation at blocks 131, 133, and 135 includes links to behavioral web sites and to blog sites where the user is able to interact with others having similar dietary and/or health problems while trying to lose weight, maintain weight loss, successfully complete exercise regimens and combat health issues through dietary and exercising lifestyle changes.

FIGS. 7A1-7A4 are an illustrative implementation of a user database format to record weight loss for a system-derived weight progression plan adapted to each user's profile and goals. The illustrative weight loss plan database format stores user data from a "start" point when the user begins the program (689), through a series of system-programmed weight loss deltas (693), until the user reaches his/her goal (697). In an illustrative implementation, the system categorizes user's weight in a category from Obese==>to Healthy (690) at a level within that category from Min==>to Max (691) plus the color associated with his/her category from Red==>Green (692) at the start date when the user first signed up for the weight loss plan.

The user database format examples shown in FIGS. 7A2-7A4 show three typical transitions for users of the present system with color codes reflecting their cumulative progress:

FIG. 7A1: user weight loss database format
FIG. 7A2: from RED obese==>to YELLOW overweight
FIG. 7A3: from YELLOW overweight==>GREEN to healthy
FIG. 7A4: from GREEN healthy==>to BLUE RIBBON ideal weight These 3 examples use the database format shown in FIG. 7A1 with typical exemplary data values. Accordingly, each of the database format fields are identically numbered but contain different data values pertinent to each example.

The database format shown in FIG. 7A1 additionally includes a set of "weight loss deltas" (693) that in this example are four sets of (unspecified) weeks over which the user's goal is to be reached. It should be noted that, if desired, there may be more than four such "deltas" defined in increments of time other than weeks. As shown in FIG. 7A1, each of the deltas 1-4 (694) define a number of pounds to be lost during each increment of time (695) as will be illustrated below. The weight loss delta portion of the database format also stores the color code (696) as it hopefully transitions from Red towards Green during deltas 1-4. It should be understood that the weight loss plan may be modified at any time to adjust the delta periods as well as the delta subgoals, e.g., to keep the goals achievable in response to the user's mid-stream progress (or lack thereof).

The goal portion (697) of the database format includes, for example, the user's goal weight (698), the timeframe (699) over which the goal is to be reached, the category (701) to be reached when the goal is attained, and the level reached (703) within that category when the goal is reached. Additionally, the database format specifies the reward (705) that the user is targeted to receive for reaching the goal. It should be understood that such rewards may be allotted upon the user meeting the expected goal increment at the end of each of the deltas specified in weight loss deltas (693), or alternatively that each delta subgoal reached can be rewarded with another smaller reward.

As delineated above, FIGS. 7A2-7A4 show three examples of use of the database format as applied to an exemplary user transitioning all the way from mid-range obese to his/her ideal weight. In the illustrative example, the exemplary user could be one individual transitioning from obese to ideal weight. However, it should be recognized that the example shown in FIGS. 7A2-7A4 may otherwise represent three distinct individuals. In fact, the 40-pound weight loss depicted in the first example is a notable accomplishment in and of itself.

The hypothetical user in the example is a postulated as a large-frame obese American male who is 5 foot, 9.4 inches tall and weighs 236 pounds. As shown in the first example in FIG. 7A2, the user is categorized as a mid-range plus obese person whose weight goal has been set to be 196 pounds in six months, which still is in an "overweight" category at a maximum level. As shown in the first example, the weight loss deltas (696) set intermediate weight goals of losing 13/11/9/7 pounds in 7/6/7/6 weeks, respectively. Thus, at a minimum, the system will prompt users to enter their current weight at least as of the end of each of the delta periods. During this time frame if the user achieves such weight loss, the users color code changes from red to orange to yellow as shown. In the first example, the user's goal is to lose the 40 pounds necessary to reach 196 pounds in six months and to reach the MAX edge of the "overweight" category in this timeframe. In fact, according to the CDC, the average weight for the American male as of 2010 is 196 pounds at a height of 5 feet, 9.4 inches. Thus according to this example, it would take at least six months to bring an obese 236-pound male back to the American average of 196 pounds at a height of 5' 9", which is right at the MAX edge of the "overweight" category (as shown in FIG. 13C2).

The reward (705) for attaining the goal is set to be 4 iTune song selections selected for example by analyzing the user's iTunes playlist as described further below during rewards processing. If desired a reward may be allotted at the end of the successful completion of an intermediate subgoal defined by one of the weight loss deltas (693). For example, if the hypothetical user after seven weeks lost 13 pounds and then after six more weeks lost 11 pounds, the system will automatically download a selected song performed by one of the user's favorite artists at the end of the 7th week and the 13th week, respectively.

In the second illustrated example in FIG. 7A3, transitioning from overweight to healthy, the hypothetical user's goal is to lose 20 pounds, from the starting weight of 196 pounds to an end weight of 176 pounds, within a 6-month timeframe. During the second set of weight loss deltas (693), the user is targeted to lose 6/5/5/4 pounds at the end of 7/6/7/6 week increments, respectively. If the user successfully meets these intermediate subgoals the user will transition from yellow==>to lime==>to green color code ratings and, thus, be targeted to receive a reward of 4 downloaded movies or books.

In the third illustrative example in FIG. 7A4, transitioning from healthy to ideal weight, the hypothetical user's goal is to lose 10 pounds from the starting weight of 176 pounds to an ideal weight of 166 pounds within a 3-month timeframe. During the third weight loss deltas (693), the user is targeted to lose 4/3/2/1 pound at the end of 5/3/2/2 week increments while transitioning between green==>to aqua==>to blue color code ratings. In this example, the blue-green color "aqua" is added as an incentive for highly motivated users trying to shed the last few pounds up to their ideal weight. For this latter example, in recognition of the arduous difficulty of an obese individual reaching his "ideal weight", the system, in concert with cooperating restaurants, may reward the user with a wild salmon dinner (e.g., in certain implementations with the purchase of a 2nd entree).

FIG. 7B illustrates user database formats to provide baseline weight loss records that document a user's food and exercise history from start to the end of the goal period. Such records provide the user's data trail for every current day X within each of deltas 1-4, where the days in the delta period run from day 1, . . . X, . . . N, where N is the last day in a delta period. Thus, the baseline records shown in FIG. 7B provide the data that is monitored by the system in order to determine whether our hypothetical user described in FIG. 7A was able to meet his initial six-month goal of losing 40 pounds on a day by day basis. The baseline records in FIG. 7B provide a mechanism for tracking food and exercise on a daily basis by creating a new record every time a food is consumed or an exercise is performed, leading to a "calories IN" for each food item consumed and a "calories OUT" for each exercise performed. While many of the data fields in the records of FIG. 7B remain unchanged, information such as the calories in, calories out, quantity information, and cumulative totals vary widely over time.

The Exercise Record in FIG. 7B1 is created for each new exercise or each old exercise with a new tag. Each exercise and food record is created on a trial basis until the exercise is performed or the food is consumed. Such is the case since the user may be considering either exercise or food to determine whether a given exercise will burn a certain number of calories or a given food/meal contains less than a certain number of calories. Field 702 in the Exercise Record identifies each exercise (e.g., bench press) with its category (weightlifting) and its mode (upper body push), as shown at 428 in FIG. 3D, at 454 in FIG. 3E, and in the Weights column 485 of FIG. 3F's Exercise Matrix. The Exercise record for the identified exercise item likewise stores the calories burned (Cals OUT) at 704, and its associated exercise tags at 706. As also shown in FIG. 3E, a Quantity tag 708 identifies, for example, a number of pounds lifted or distance run; a Time tag 710 identifies the duration of the exercise in hours (e.g., for workouts or marathons) and/or minutes (e.g., for treadmill sessions or miles run) and/or seconds (e.g., for quick-burst events like sprints and dashes). Likewise, a Cycle tag 712 may be included to define the number of sets performed, the number of repetitions performed per set, or other such data. The exercise record also includes a Usage Counter 714 to keep track of the frequency the exercise has been performed. Moreover, WRT exercise usage counter 714, if the same exercise is performed (or WRT the food usage counter 732, if the same food is eaten) the same old record may be updated by simply incrementing the usage counter+1. The Other Tags/Qualifiers field 716 is available to track, for example, a handicap or physical limitation the user may have that limits his/her exercise capabilities (e.g., due to a weak limb or one that has limited range of motion). The exercise record also includes a Dates field 718 to register each date the exercise was performed.

The Food Record shown in FIG. 7B2 is created for each new food or each old food with a new tag. Field 720 in the Food Record identifies each Food (e.g., Turkey Breast+ gravy) with its meal (Dinner) and its dish (Poultry), as shown at 368 in FIG. 3B and in the Dinner column 383 of FIG. 3C's Meal Matrix. The Food Record for the identified food item likewise stores the calories consumed (Cals IN) at 722, and its associated food tags at 724. As also shown in FIG. 3B, a Quantity tag 726 identifies, for example, a number of ounces/pounds in the portion entered by the user (e.g., 7.7 ounces) and a Nutrient tag 710 delineates the nutrients that are provided (adjusted to a 7.7 oz portion), e.g.:

Calories: a minimum 325 Calories IN (16% DV) for its portion size

Protein: a maximum 67 g Protein (134% DV) and maximum Amino Acids e.g., all 9 essential Amino Acids @ 108%-183% of RDA for a 220-lb male Fats: a minimum 1.3 g of Saturated Fat (6% DV) and minimum 0.05 g Trans-Fat Minerals: a minimum 219 g of Sodium (9% DV) with maximum 4 mg zinc (27% DV) and 67 mmg of hard-to-find Selenium (96% DV)

Vitamins: 26 mg of Vitamin B-3 Niacin (130% DV)

All the above data was excerpted from the USDA Nutrient DB (see FIG. 4B) and was delineated in the side-by-side comparison with salmon (see FIG. 4C)

Additionally, the food tag field includes an Add-on Calories tag 730 to define the number of calories attributable to add-ons (e.g., gravy). As explained above, in connection with the exercise record, the food record additionally includes a Usage Counter 732 to identify the number of times a user consumes the given food (e.g., Turkey Breast). A field defining other tag qualifiers 734 is provided, for example, to identify a user's food allergy. A date field 736 is provided for identifying each date the food was eaten—from the first time until the last—to provide a history of food consumption. By providing the dates each food was consumed, the system is able to identify good and bad patterns, such as the fact that the user generally eats a large steak twice a week, thereby contributing to an already problematic high cholesterol problem. In an illustrative implementation, armed with this or similar data, the system is able to recommend healthier alternatives (for example, smaller portions with lower cholesterol) to proactively address the issue in real time before further damage is done.

In order to track progress towards a user's goal on a daily basis a daily record is maintained and updated with every user's use of the system. As shown in FIG. 7B3, a Daily Record is maintained by providing cumulative daily totals of the food record's Calories IN 722 and the exercise record's Calories OUT 704, i.e, once it is confirmed that the record has advanced beyond the trial stage where the user is merely considering eating a food or doing an exercise. Once the user has confirmed eating the food or doing the exercise, the respective calories are added into the daily record's food Calories IN field 742 and the daily record's exercise Calories OUT field 744, as described above WRT the Food Mode and Exercise Mode (via Calculate Calorie calls F2 in FIG. 4A and E2 in FIG. 5A, respectively). The daily record likewise includes, with the user's cooperation and entry of the user's current weight (748) and the current date (750).

The Daily Record also includes an Expected Weight Loss in field 740 which the system calculates for the current day X (as defined at the top of FIG. 7B). For example, here is how the Expected Weight Loss is calculated for the 1st Delta in FIG. 7A2: the 1st Delta projects an expected loss of 13 pounds across seven weeks; if the current day X is the completion of the 21st day, the expected weight loss is 3/7ths (43%) of the projection for delta 1 (13 pounds) or as a simple equation: 3/7×13 lb=5.6 lb expected weight loss by day 21 of 49 days. Based on the cumulative calorie data in the daily record fields Cals IN 742 and Cals OUT 744, a calculated weight loss (gain) field 746 is formulated by a generic equation: Weight Loss (lbs)=(Cals OUT−Cals IN)/3500 calories/lb, where 3500 cals/lb of body fat is modulated by user weight, age, sex, activity level, and obesity level.

The baseline records in FIG. 7B also include a Delta Record which is updated daily. The delta record includes a Cumulative Expected Weight Loss field 752 that records the expected weight loss totals for each day accumulated across the delta (day 1 to day X, the current day) that is used as a reference. The delta record also includes for the delta period at issue, a cumulative food Cals IN field 754, a cumulative exercise Cals Out field 756 and a calculated weight loss (gain) 758 that utilizes the data in field 754 and 756 to determine a calculated weight loss or gain up to the current day X in the period at issue (based on the difference between calories OUT and calories IN divided by 3500 calories, as just described above). The delta record also includes a current weight field 760 (and current date field 762). that is entered by the user (preferably on a daily basis) to provide the system with accurate weight loss data that is not otherwise derived from cumulative food and exercise inputs.

Minimizing the Size of System Databases: to minimize the physical size of the system databases over many years of anticipated exponential growth, the record structure has been built like an "Egyptian pyramid" for each user:

FIGS. 7B1/7B2: the structure is large and volatile at the base of the pyramid where one record arises from every new/unique Food and Exercise transaction; volume is minimized by incrementing a usage counter for each repeated item; and any variations in "tags" associated with the same food/exercise are merely tacked onto the variable-length original record to avoid making another record; nutrients are stored once (in mg/100 g units) and scaled up/down to portion size FIG. 7B3: the structure is steady and predictable in the middle of the pyramid where just one small record emerges per day for all Food/Exercise transactions; fixed disk space can be allocated yearly since the DB only grows 1 record/day; the resulting DB allows the system to display cumulative weight vs time plots FIG. 7B4: the structure is small and pointed at the top of the pyramid where just one record carries all the cumulative data for each successive delta; thus, only the original plus 4 delta records are generated for any given weight plan; the resulting DB allows quick display of weight vs time plots across all 4 deltas which simplifies any statistical analysis across the entire population of users FIG. 8A illustrates an exemplary user profile record format. FIGS. 8B and 8C respectively illustrate a user's Food Record format and Exercise Record format that also may be part of the user's profile or, alternatively, may be stored locally as databases on the user's mobile computing device, e.g., an iPhone. The illustrative user profile record formats 720, 728, and 760 shown in FIGS. 8A through 8C are initially populated during the create user profile processing described above in conjunction with, for example, the flowchart depicted in FIGS. 3A and 3D.

As shown in FIG. 8A, the user profile record format 720 includes a user ID data list 723 that, for example, is stored as a set of fixed length data records and specify an identified data item 721 and at least one qualifier 722. The identified data items 721 shown in FIG. 8A are illustrative only and may be expanded or contracted to meet the needs of a given implementation. The illustrative data items are largely self-explanatory and are only briefly described.

The user ID data list 723 includes a user ID number that is assigned by the system to uniquely identify the user. Further, a revision level data item is included that identifies the number of times that the user has revised his or her user profile. The original user profile created by the user when first using the weight and exercise tracking system described herein, forms the baseline record for the user and is preserved intact.

The date and/or time the user initially begins using the system and a device number, a unique identifier identifying the user's portable computing device (such as a cell phone serial number), are also stored. The identification of, for example, a cell phone serial number permits added security features to be included in illustrative implementations. The user's email address may be acquired to serve as an alternative communication link and to, for example, communicate with the user to, for example, enabling the system to confirm that changes made to the user's profile were actually made by the authorized user.

The system also records in the user's profile, the user's name (e.g., while a name like "John" may be accepted, the system may also use a unique numeric modifier to distinguish John Smith from John Doe), sex, age, height, wrist size, and waist size. As explained herein, measurements of wrist size may be simply made by users with a string and a ruler and permits the system to identify the appropriate category for the user's body frame. The user's waist size permits the system to determine whether the user should be characterized as, for example, overweight or obese.

The exemplary list of data items 721 include an ID flag that identifies any change that is made in the user data item list so that the system may, if desired, challenge any such change. In an illustrative implementation, any time a change is made in the user profile, the data is recorded as a subsequent revision of the user's profile, e.g., Rev 2 is a revision of Rev 1.

The user ID data list 723 includes various weight related entries such as weight0, weight5, weight10 which respectively store the user's current declared weight, the user's weight five years ago and the user's weight 10 years ago. The user profile also stores the user's ideal weight by accessing the ideal weight database shown in FIG. 13C using the data entered including the user's gender, weight, height, wrist size, and waist size. In certain implementations, the user ID data list 723 includes a weight flag to indicate whether the user has modified his or her entered weight. In other alternative implementations, the user's current weight may be stored in memory locations other than the user's profile for generating the weight displayed in FIG. 10. The user ID data list 723 also includes a defined set of goals that the user defines during the processing at block 308 of FIG. 3A. A user may, for example, define a goal of losing or gaining weight including a specific goal weight (goalW).

In certain illustrative implementations, such a user specified goal weight may be used to set the user's original goal weight. In other illustrative implementations, particularly those in which the user has selected no weight goal, the ideal weight database illustrated in FIG. 13C may be used to set an initial goal. In yet other instances, a physician, nutritionist, personal trainer or other third party may have set a weight goal for the user.

Turning back to FIG. 8A, in addition to a weight goal, the system may, in illustrative implementations elicit further user goal information which is recorded by the system. For example, the user may, for example, in response to system queries indicate a goal of getting stronger (goalS) that may be attained by increasing the weight used during the user's top-five weightlifting exercises. Thus, in an illustrative implementation, an assessment of the user's top-five weightlifting exercises may be used to assess the user's baseline level of strength. Moreover, such an assessment can be used to define a reasonable approach that may be used to increase strength such as by increasing the initial weight used for bicep curls from 20 pounds to 30, 35, and 40 pounds over time.

Similarly, a user's indicated goal of increasing endurance (goalE) may be specified in response to system queries (e.g., "Is your goal to increase endurance?") and attained by assessing the user's top-five endurance exercises.

For example, endurance may be enhanced by increasing the distance run, cycled, or swum during one or more of the user's top-five endurance exercises. A goal of getting healthier (goal H) may be specified in response to system queries (e.g., "Is your goal to get healthier?") and may be attained by assessing the user's top-five foods/meals and, for example, by recommending alternative foods high in vitamins and health promoting nutritional parameters. Further, a goal of dropping bad habits and/or treating addictions (goal D) may be identified in response to system queries (e.g., "Is your goal to increase endurance?" and "what is your bad habit or addiction?") which can be attained by, for example, monitoring and rewarding the user's progress with respect to not smoking, not drinking, not using drugs, food addictions, etc.

The user ID data list 723 also includes a goal date for achievement of a defined goal and may be set by the user or system. A goal flag is set upon any change in an identified goal. Thus, if the user defines a new goal weight, the system re-calculates any prior plan for goal attainment to take into account a new endpoint.

As shown in the FIG. 8A illustrative implementation, the user ID data list 723 also specifies three levels of rewards to be applied to the associated user for reaching both the users final goal and any of a number of various subgoals. In this example, the system identifies a "rewardDS" that is the lowest level reward which is triggered by a user reaching one of the four weight loss Delta subgoals, such as is described in FIGS. 7A1 through 7A4. The system also identifies a "rewardFG" that is the highest level reward for reaching the user's overall final goal. Additionally, the system also identifies a "rewardBR" that is a "Blue Ribbon" reward recognizing that the user, for example, exceeded his or her final weight loss goal by 10%. Alternatively, the "rewardBR" may be reserved to users who achieve their ideal weight has specified by the ideal weight database shown in FIG. 13C.

As illustrated in FIG. 8A the user profile record formats 720 also includes a list of user health data 724. Such user health data includes the user's own impression of his/her general level of health (level 0), and his/her declared level of health, 5 years ago and 10 years ago (level 5 and level 10). In an illustrative implementation, a user may characterize his general level of health on a scale of 1 to 5 that may be stored as a fixed length record. By having multiple levels relating to the current general level of health and past levels of health permits the system to determine whether the user perceives his/her general level of health as improving or declining over time, which may affect, inter alia, the severity and/or intensity of exercises suggested for the user.

The user health data list 724 also provides for variable length records which allow a user to define, for example, his or her handicaps. Thus, a user may, for example, indicate that he or she is confined to a wheelchair, lacks a specified limb, has limited eyesight, etc. In an illustrative implementation, for each of the specified handicaps the user is asked whether the handicap has existed for five years or 10 years to determine, inter alia, how recently the user might have eaten typical foods and/or performed typical exercises. The user health data list 724 also includes an ailment data item, wherein the system records whether the user is suffering from, for example, asthma, allergies to specific foods, etc. in the period of time over which the user has been suffering from such ailments. Moreover, the ailment data item may be used to indicate that the user is a diabetic, has high blood pressure, cardiac issues etc. The health data list 724 also includes a data item entry for injuries 1 to N to identify temporary health issues, such as a sprained ankle or a separated shoulder, which usually heals over a short time.

The user health data list 724 also includes a Weak Flag that is set for each weak limb (or associated muscle, such as a hamstring). Such a flag is set if, for example, a user identifies a weak left or right arm that cannot exercise to the same extent as its counterpart, e.g., many right-handed tennis players have weak left arms. Similarly, a Range Flag is similarly set if, for example, a user identifies a limb or (or associated muscle) that has a limited range of motion. Given such limitations, the system would not recommend exercises that involve movement beyond the limited range, or that require equal pressure, e.g., on a loaded barbell—i.e., in this case, the system would recommend isolated exercises (described above) where, for example, the weaker arm would use a lighter dumbbell.

In an illustrative implementation, the user health data list 724 also includes a data item for the user to identify a range of habits including but not limited to smoking, drinking, drug issues, food addictions etc. Additionally, a user's medications are identified that, for example, are utilized to treat any of the identified ailments and injuries. The list of medications may, for example, be analyzed by the system to determine whether such medications will present normal weight loss or tend to trigger increased weight gain. If such is the case, the system may recommend alternative medications or alter goals in light of such a medication.

The user health data list 724 also includes a data item "Restrict F" to identify foods excluded due to food allergies, ailments, or any other condition identified by the user. For example, a user who identifies a peanut allergy may identify specific peanut containing foods that should be excluded. Moreover, in an illustrative implementation, the system may access well-known sources for a list of foods that should be avoided in light of the given allergy to identify foods that may be unknown to the user that may cause issues in light of an identified allergy. Further, the user's health data list 724 includes a "Restrict E" data item that identifies specific exercises that are either limited or excluded in light of handicaps, ailments, or injuries identified by the user.

Food-related restrictions may be stored in the user's profile based upon information received directly or indirectly from a participating physician and/or nutritionist and/or healthcare provider including any thresholds for the user including but not limited to caloric intake, grams of saturated fat, grams of trans fat, milligrams of cholesterol, milligrams of sodium, grams of carbohydrate dietary fiber, grams of carbohydrate sugar, grams of protein, amounts by percent of daily requirement of Vitamin A, Vitamin C, Calcium and Iron, amount of exercise energy expenditure and other variables related to specific medical, nutritional and other needs of the user. Moreover, based upon input received directly or indirectly from a physician, restrictions that are stored in the user's profile may be placed on both food and exercise for users suffering from cardiac issues. Checks are made to ensure that any health-related nutritional and exercise thresholds have not been exceeded. Examples include excess sugar consumption by users who have diabetic or borderline diabetic issues, excess sodium in those with hypertension, excess potassium and protein in those with renal disease and exercise limitations in the user with cardiovascular disease.

In illustrative implementations, based directly or indirectly on input from a physician, food consumption and exercise thresholds may be dynamically changed in the user's profile as necessary. Exercise, for example, may increase from an expenditure of 300 calories per day, 3 times per week early in the process to 500 calories per day, 5 times per week with light weights by the end of the active weight loss process. Calories may be advanced at this point from, for example, 1200 per day to 1500 per day. In illustrative implementations, such restrictions may be identified in the user's profile in the variable length food and exercise restriction segment thereof. As another example of dynamic regimen changing, if a behavioral issue exists such that the user is not doing well adhering to the initially prescribed dietary regimen, an assessment of the issues contributing to the adherence problem can be made and the dietary regimen might be changed based upon an analysis in conjunction with the FIG. 6B behavioral processing, for example, by increasing calories or adding more fruit to help the user improve adherence.

FIG. 8B illustrates a portion of the user profile/food record format 720 that stores the user's top five favorite foods and/or meals 729. In any illustrative implementation, it should be understood that, while the user profile record format specifies the user's Top 5 favorite foods/meals as shown in FIG. 8B, such data is stored both locally (e.g., in the user's iPhone) and remotely (in the system server 14) as a separate Food Record database. It should also be noted that, while the system encourages the user to enter all the food data he/she can as a meal or as separate items, all such data entered and stored (e.g., in the record format of FIG. 8B) is ultimately converted and stored as individual food items in the food record format of FIG. 7B2, one record per item (plus tags and add-ons).

In an illustrative implementation, the same storage format and sequencing is used for recording the user's Top 5 favorite foods/meals is also used for recording everyday food consumed by a user at, for example, a restaurant via the Food Mode process of FIG. 4A. In this example, a user is initially prompted to enter his or her most favorite food/meal. The system maintains a list of favorite breakfasts, lunches, and dinners entered by a user (including all add-ons) such that, for example, the user may identify his top favorite breakfast as "breakfast number 1" for ease of subsequent data entry. Such a favorites list with add-ons is displayed to the user so that he/she can quickly and accurately select a predefined meal that he/she habitually consumes for convenient entry into the system. Once the user realizes that every food/meal entered gets offered back to choose again and again, he/she will be more inclined to enter more foods/meals from then on.

As illustrated in FIG. 8B, after certain favorite-related entries are provided by the user (730) as explained below, the system determines and stores in the user profile, calories consumed 741, the amount of macronutrients (carbs, proteins, etc.) 742, and the amount of micronutrients (vitamins/minerals) 743. Storing such nutritional information in association with the user's profile permits efficient, local, off-line accessing of such information whenever such favorite items are consumed. As shown in FIG. 8B, the user's entries are totaled (736) so that the total nutritional impact of the user's selections is appreciated by the user in real time.

In addition to the amount of calories, macronutrients, and micronutrients, the system associates color codes with the user's profile that may be stored in a linked shadow database. As illustrated in FIGS. 2C-2E, in an illustrative implementation, every food/nutrient and exercise/activity is assigned a color code reflecting its relative value "Worst 1==>5 Best" that is linked to the User's profile and/or food database. As a rule of thumb, in an illustrative implementation, every food color code has the same bad==>good value applicable to all Users, whereas all exercise color codes are only bad==>good with respect to each individual's capabilities and user profile in FIG. 8A.

The color codes assigned to each of the foods/add-ons and macro-/micro-nutrients are mapped (as numbers 1==>5) into a "shadow" DB correlated 1-for-1 with this DB. The shadow DB provides instantaneous access to associated color codes, since each code is the exact same relative displacement within that DB as its parent data item in the above FIG. 8B related DB. (As a system-level programming note that can be appreciated by those skilled in the art, such a fixed "relative displacement" is easily incorporated for color code access made via software instructions, but it is far more efficiently enabled by "indirect addressing" offsets imbedded in the hardware instructions.) This shadow DB requires minimal disk space since, in an illustrative implementation, only single-digit numeric codes (and no text) are stored therein. The shadow database, in an illustrative implementation, occupies the lowest level of a hierarchical database system in which color codes are associated with each selected food and exercise item. Thus, each time a food item is identified and accessed, an associated color code from the shadow database is automatically retrieved and displayed therewith in a manner that can be appreciated by those skilled in the art.

While most of the data items referenced in FIG. 8A are fixed length data items, the data items shown in FIGS. 8B and 8C relate to variable length open-ended lists of items. For example, a favorite meal identified by a user may include a main course of beef and any number of a wide range of vegetables such as green beans, spinach, squash, etc., an add-on sauce, and a variable number of drinks. Thus, the data records are open-ended and variable length, where each of the fields in the record is a variable length field, as is indicated, for example, by the data flow in FIG. 3B. In an illustrative implementation, for each user dish chosen, the tags indicated in FIG. 3B (which have the greatest variability, e.g., as independent add-ons) are stored in an associated separate database, such that the dishes are stored in one segment of the database and the tags are stored in another cross-referenced segment of the database in a variable-length format.

FIGS. 8B/8C here have a dynamic variable-length database structure in an effort, for example, to minimize the size of the User Profile DB:

- all food/exercise data with wide-ranging values are variable-length open-ended lists, rather than fixed choices
- all individual text fields are also variable-length, rather than widened them out to the maximum text value
- all but the 1st DB segment are variable-length, e.g., adding up to 5 Favorites per each category
- for quick "burst-energy" exercises like sprints and weightlifting, the record is extended by modular data for 1==>N Trials/Sets (see the cyclical format)

The following is an exemplary sequence of DB segments with their respective variable lengths, if any:

| DB Segment | Variable Length |
| --- | --- |
| [1] FIG. 8A: User ID (per FIG. 3A) | None - all data items appear in short fixed-length fields |
| [2] FIG. 8A: User Health (per FIG. 3A) | Every data item except the fixed-length first item, General Level of Health |
| [3] FIG. 8B: Top 5 Favorite Foods | All 12 Dishes, plus Snacks/Drinks, and Vitamins/Minerals |
| [4] FIG. 8C: Top 5 Favorite Exercises | All 5 Categories, plus increasing Goals/Sets @ different Trials/Reps |
| [5] FIGS. 8A/8B/8C: Color Code "shadow" DB | Exact same variability as data items in segments [2]/[3]/[4] above |

As indicated in FIG. 8B, the user identifies a category 738, add-ons 739 and a quantity 740. It is noted that the breakfast, lunch, and dinner columns in the food database illustrated in FIG. 3C correspond to categories B/L/D (breakfast/lunch/dinner) 738 and the associated add-ons 739 (which may include any number of additional add-ons beyond the two shown in FIG. 8B). With respect to the categories 738, in an illustrative implementation, the cycle of 12 dishes identified in rows 732 to 734 repeats up to five times each for the user to select his/her Top 5 breakfasts, Top 5 lunches, and Top 5 dinners. It is noted that, in an effort to be as user-friendly as possible in this very first user contact, the system will accept as many as 10 or as few as one Top item that the user is willing to share—the more he enters, the better the system will know him.

In an illustrative implementation, in completing his or her user profile, the user is prompted to select a category of favorites such as B or L or D, and then select any desired add-ons (739) and quantities (740). Thus, if for example the user chooses the category lunch (738), the user may select beef, chicken, fish, or a vegetable (733) together with desired add-ons (739) and then add any desired dishes from rows 732, 734. The user may next select a similar set of Top 5 snacks and/or drinks indicated in row 735. Once the user selects a particular category such as drinks, a user will be presented with popular examples such as coffee and cream as shown in the food database of FIG. 3C to stimulate his/her participation. With respect to snacks and drinks (735), these items also constitute open-ended lists that store from 1 to N items the user may consume.

Furthermore, in an illustrative implementation, the system next prompts the user to enter his/her favorite vitamins/minerals/omega-3 s/antioxidants/herbs/etc. which are stored as an open-ended list for each category, such as is shown in FIG. 2E. In an illustrative implementation, system recommendations may be provided to the user with respect to additional vitamins or minerals, depending upon the user's identification of vitamins and minerals taken on a regular basis.

FIG. 8C illustrates a portion of the user profile/exercise record format 760 that stores the user's top five favorite exercises and/or activities 747. In any illustrative implementation, it should be understood that, while the user profile record format specifies the user's Top 5 favorite exercises/activities as shown in FIG. 8C, such data is stored both locally (e.g., in the user's iPhone) and remotely (in the system server 14) as a separate Exercise Record database. It should also be noted that, while the system encourages the user to enter all the exercise data he/she can as a circuit set or as separate items, all such data entered and stored (e.g., in the record format of FIG. 8C) is ultimately converted and stored as individual exercise items in the exercise record format of FIG. 7B1, one record per item (plus tags).

In an illustrative implementation, the same storage format and sequencing is used for recording the user's Top 5 favorite exercises/activities is also used for recording everyday exercise performed by a user at, for example, at home or at a gym via the Exercise Mode process of FIG. 5A. In this example, a user is initially prompted to enter his or her most favorite exercises/activities. The system maintains a list of favorite activities, sports, and conditioning exercises entered by a user (including all tags) such that, for example, the user may identify his top favorite activity as "Activity number 1" for ease of subsequent data entry. Such a favorites list with tags is displayed to the user so that he/she can quickly and accurately select a predefined exercise that he/she habitually performs for convenient entry into the system. Once the user realizes that every exercise/activity entered gets offered back to choose again and again, he/she will be more inclined to make the effort to enter more exercises from then on.

FIG. 8C illustrates a portion of the user profile/exercise record format 760 that stores the user's top five favorite exercises and/or activities 747. In any illustrative implementation, it should be understood that, while the user profile record format specifies the user's Top 5 favorite exercise/activities as shown in FIG. 8C, such data is stored both locally (e.g., in the user's iPhone) and remotely (in the system server 14) as a separate Exercise Record database.

The entries in the user profile/exercise record format 760 are provided by the user except for the Cals OUT that are calculated by the system.

As can be seen from FIG. 8C, the categories 754 parallel in many respects to the modes of activities identified, for example, in FIG. 3D and in the FIG. 5A Exercise Mode flowchart. Thus, in entering his or her top five favorite exercises/activities, the user selects activities from the following categories: Daily Activity 748, Periodic Activity 749, Sports (Competitive and Noncompetitive) 750, Conditioning (Noncompetitive) 751, Weightlifting (Noncompetitive) 752, and multiple trials/sets 1 to N (of quick "burst energy" exercise) 753.

With respect to the categories 748 to 753, the data entry cycle repeats up to five times for each of the Daily, Periodic, Sports, Conditioning, and Weights exercises. As shown in FIG. 8C, each of the Daily Activity 748, Periodic Activity 749, Sports 750, and Conditioning 751 categories is characterized as being either an indoor or outdoor activity. Additionally, each exercise is qualified by the user specifying a level within the identified category and a specific exercise item such as riding a bicycle to work, playing golf, football, running, using the stair stepper or doing bicep curls (755). Further, each such activity/exercise is qualified by entries defining appropriate quantities for the identified activity (pounds/distance, quarters/distance, resistance, etc.) 756, time/duration 757, frequency 758, cycle information including goals/sets, trials/reps (759), and calories burned (Cals OUT) 760 that are calculated as shown and described WRT the Exercise Mode flowchart in FIG. 5A.

Periodic activities 749, as described above in conjunction with FIGS. 3D and 5A, include various indoor and outdoor activities that may be performed either at home or away from home. Indoor activities include, for example, vacuuming, washing floors, and playing pool. Outdoor activities include, for example, washing a car, mowing the lawn, etc.

In an illustrative implementation, all competitive and noncompetitive sports are grouped together in a Sports category 750. where each team sport is further qualified by the user's position on a team such as goalie, pitcher, quarterback, guard etc. This is because the position on a team may significantly impact the calories burned during participation in sport. For example, an outfielder in baseball burns significantly less calories than the team's pitcher. Furthermore, each sport is qualified by the user's level of competition, which in turn will trigger changes in the Cals OUT calculation. For example, a professional soccer player will inevitably burn more calories playing soccer than a middle school player. Such levels of competition include, for example, training only, recreational, middle school, high school, college, club sport, semi-professional and professional. Cycle information is also recorded, if pertinent to the sport at issue focusing on, for example, goals, sets, planned attempts/trials, and or number of actual repetitions completed. For example, a 260-lb weightlifter tries to bench press 200 lbs for 3 sets of 5 reps—he manages to complete the first 2 sets without a problem but, as lactic acid builds up, he fails on the 4th rep of the 3rd set. Using the cyclic "Multiple Sets" provision of the Exercise DB here, this would end up as a parent Bench Press record with set tags 1/2 showing Pass and tag 3 showing Fail.

With respect to conditioning activities 751, a wide range of activities summarized in conjunction with FIGS. 3D and 5A is contemplated including indoor activities such as situps, push-ups, and Pilates. Indoor activities using machines such as a stationary bicycle, treadmill, rowing machine, stair stepper etc., are also tracked. A wide range of outdoor conditioning activities are also contemplated for tracking including walking, jogging, running, swimming, skating, etc. As shown in FIG. 8C, such activities are qualified by specifying such quantities as the distance run and the resistance level set on the equipment. Additionally, the time participating in the identified activity is entered together with the frequency per day or per week. Cycle information is also recorded if pertinent to the conditioning activity including the user's goals, sets, planned attempts/trials, and or number of actual repetitions completed.

The Exercise Mode routine in FIG. 5A (which makes each record for the Exercise database here) also tracks weightlifting exercises 752. Such activities are identifed in FIGS. 3B and 5A as described above. For example a user who performs bench presses would have such exercise categorized as an "upper body" exercise activity at the "level" of "body only" and with "bench press" identified as the exercise item. In this example, the user then identifies the amount bench pressed under quantity, e.g., 200 pounds (as just described in the dynamic Multiple Sets example above). To complete the cyclic Multiple Set records, the user also enters whether he Passed or Failed the lift, his rest interval between sets, and his final pulse rate in response to display of his Target Pulse Range calculated @ 60-85% of the predicted MAX heart rate for his age—i.e., Target Pulse Rate=(60-85%)×(220−age) for any healthy user at age 20==>70. At different times thereafter, the user also identifies the time spent bench pressing and the number of times per week such an exercise is performed. The system, utilizing a database of the nature shown in FIG. 5B, calculates the calories burned during such an activity and stores such a value in the Cals OUT field 761 associated with this weightlifting exercise.

The multiple trials/sets entry 753 permits the system to handle "burst-energy" exercises below 1/2-hour to extend the tracking system across the entire sports spectrum, i.e.: from slow "low-energy" exercises greater than 30 minutes==>to "quick-burst" acts of less than 30 seconds. This format for repetitive "sets" of a given lift may be applied to ALL likewise-repetitive "trials" for increasing Track & Field "goals" in the sports record 750:

e.g., short races/sprints/shotputs/throws/vaults==>for a single BEST/MAX goal e.g., pole vaults/high jumps/long jumps==>for an increasing-level BEST/MAX goal. That is, for such a given track and field event, the goal is to reach a MAX height/distance in the trials allowed.

In an illustrative implementation, the tracking of weightlifting may be expanded from exercise record 752 via the use of the multiple trials/sets entry 753 (see the dynamic Multiple Sets just described in example above). If, as in the earlier example, the user completed the 5th repetition of bench pressing 200 lbs, the user will be credited with passing the trial. Additionally, in an illustrative implementation the user's target pulse range based upon age limitations is identified together with the pulse rate achieved during the exercise. Rest interval information between repetitions is also identified. Such information is recorded for each of multiple trials and sets. The system may then recommend to the user, the parameters of the next set based on the user's performance of the just completed set. Thus, such timely interactive information allows the system to dynamically recommend increasing/decreasing the amount of weight being bench pressed, decreasing the rest interval, increasing/decreasing the number of repetitions etc.

In this fashion, in an illustrative implementation, such a weightlifting training protocol permits the system to act as a "personal trainer," interactively guiding the user through a rigorous weightlifting workout in real time. In an illustrative implementation, through the use of databases stored locally in for example, a 64 GB local cell phone memory, such personal trainer functionality may be accomplished off-line without any internet link to the remote server.

The inherent advantages of this efficient, dynamic DB format are:

ALL exercises can be tracked . . . from longest/slowest==>to shortest/fastest the DB's compact size allows, in an illustrative implementation, the whole DB to be locally stored in the user's smartphone this enables the user to access/update the DB in real-time, without being online with a server enabling full functionality inside a gym or other location where there's often no signal the system provides real-time feedback to the user, e.g., based on the results of previous N–1 set (pass/fail, rest interval, pulse rate, etc), the system can adjust optimal weight/reps for sets N/N+1/etc so as not to "kill" user enthusiasm.

FIG. 9 is an illustrative depiction of a calculate calories subroutine. The calculate calories subroutine has four distinct subroutines, each having a respective entry and exit point associated with nodes Food1 (F1), Food2 (F2), Exercise (E1), and Exercise2 (E2). Each of these four subroutines calls a common subroutine to display calories that is shown in FIG. 10.

Beginning with the F1 subroutine, this subroutine is executed to perform the functions shown in FIG. 4A associated with the Nutrient Database 566 and the function of displaying food nutrients with quantities and color codes 568. As shown in FIG. 9 when the Nutrient Database is accessed (770) to display nutrients (772), the system looks up both the food item and the add-on in the system Nutrient Database which in turn is based on data obtained from the USDA Nutrient Database (774). Thus, the calorie data contained in the USDA nutrient database is stored, for example, in a database resident at server 14 shown in FIG. 1.

Thereafter, as indicated at block 776, the calories contained in the food and add-on are calculated to factor in the quantity of food and convert to the unit of measure being tracked by the system based upon the data been entered by the user (e.g., 8, 10, 12 ounces). Such a calculation is necessary to scale the user's portion up/down to match the unit measure of the USDA database calorie data which is in milligrams per 100 grams (mg/100 g). Once the food and add-on calories are each calculated, the associated values are stored in a trial food record (778). The data is not permanently entered into the system until it is confirmed that the user is past the consideration stage and has consumed the food. The food being consumed together with all nutrients, such as grams of proteins, are displayed to the user (780), and the calories consumed are also displayed (782). Thereafter, the routine returns to block 568 of FIG. 4 (which called subroutine F1) in light of the completion of the processing associated with the display of food nutrients with quantities and color codes.

As previously described in conjunction with FIG. 4, after the completion of processing associated with block 568, the system checks to determine whether the food has been eaten at block 570 and, if so, the user food database is updated by updating the user's favorites and creating a new record. The processing associated with the user Food Database at block 571 is performed in this example by calling the F2 subroutine. As shown in FIG. 9, utility subroutine F2, which is called from the Food Database block 571, operates to update the user's food favorites. In so doing, the food record shown in FIG. 7B is updated/created (790) in the food record's food usage counter (732) in FIG. 7B is incremented by 1 (792). Thus, if the food at issue is consumed for the first time, the previous count in the food usage counter will be zero, resulting in the current usage counter state being incremented to "1."

Thereafter, the food calories in (i.e., consumed) are added to both the daily record and the Delta record (796) shown in FIGS. 7B3/7B4, respectively. The calories are then displayed (798) and the routine returns to the calling routine in FIG. 4 to update favorites at block 573.

Turning next to the Exercise1 subroutine (E1), this utility subroutine is called during the processing previously described in FIG. 5A. Initially, the activity database is accessed (616) to begin calculating calories burned for a given activity using the calories burned and/or the calorie coefficient data in the calorie coefficient per user activity database illustrated in FIGS. 5B/5C (806). The E1 subroutine looks up the exercise as further specified by the associated tags in the system Activity Database, which is illustrated in FIGS. 5B/5C and is based on the "Compendium of Physical Activities" published by Ainsworth et al. (2011), as updated by Arizona State University in August 2012.

Thereafter, the calories burned during exercise are calculated using the calorie coefficient obtained from the database illustrated in FIG. 5B in 5C (808). The calories burned are determined by the user's body weight times the calorie coefficient. The calories burned are then stored in a trial exercise record (810) and the calculated calories, together with the associated exercise tags including the color code, are displayed (812). The subroutine then returns to FIG. 5A to display the chosen exercise (620), enabling the performance of this display function. A check is then made to determine whether the exercise was done (680) as previously described in conjunction with FIG. 5A. If so, the update favorites processing commences.

Update favorite processing (684) calls the Exercise2 subroutine (E2). Upon the initiation of E2 (816), the routine accesses the exercise record shown in FIG. 7B (820) to increment the exercise counter by one (822). Thereafter, the exercise Cals IN from the calculation in subroutine E1 at block 808 are added to the baseline records of FIG. 7B (821) including the daily record and the delta record (826). Thereafter, the calories and other associated exercise data are displayed (828) and the routine returns to the update favorites processing at block 684 (830).

FIG. 10 is an illustrative display for depicting to the user certain calorie and goal information. The display chart shown in FIG. 10 applies to any goal over any given time where the current value for the current day X lies somewhere in between start day 1 and a goal day N (expressed as 1, . . . X, . . . , N). The meaning of "to date" in FIG. 10 is the cumulative value of the variable across time from the starting date in the program to the current date.

The display in FIG. 10 displays expected calorie values based on goal calculations and actual calorie values accumulated from calories consumed and calories burned (today and to date), all of which can be compared on the LH side to the current actual weight measurement input by the user. Alternatively, instead of cumulative calorie levels, the display could show the calculated weight (or loss or gain) resulting from the cumulative calories OUT versus calories IN. Either way, the net result here is that the user now can, at a glance, compare the actual weight he/she just entered today with both the expected weight he/she was supposed to reach by today and the actual weight (calculated from his/her exercises versus foods eaten) that should have resulted by today.

The display shown in FIG. 10 may, for example, be designed to illustrate performance during one of the four Delta periods described above in conjunction with FIG. 7A. With respect to the user's goals, under the "goal weight" display, the user starting weight, such as 300 pounds is displayed (852). Additionally, in an illustrative implementation, associated with the "Goal Weight" heading, the delta period is identified together with the goal weight calculated for achievement at the end of such a delta period, e.g., 285 pounds. Further, the user's expected current weight, such as 290 pounds, is displayed (854). Additionally under the "calories to date" heading the total expected calories IN (858) and the total expected calories OUT (860) are displayed. Further, under the expected values portion of the display in the "goal cals today" heading, the expected goal for the calories in (864) and calories burned/out (866) for the current day are identified.

In this example, with respect to the "actual values" for user weight (868), the user's starting weight is again identified at (870) for comparison with his/her actual current weight displayed at (872). In this fashion, a user can see his/her actual current weight and compare the actual calculated weight with the current expected weight for goal achievement at block 854. In an illustrative implementation, this display may be augmented with the color codes associated with the user's weight loss progress to date, visually depicting the degree of progress. Additionally, under the "user cals to date" heading (874), the actual total number of calories consumed (876) and the total calories burned (878) during the delta period to date are identified for comparison with the calculated calories IN and calories OUT for goal achievement.

In an illustrative implementation, this display may be augmented with the color codes associated with the user's progress to date regarding calories consumed and burned, visually depicting the degree of progress. Finally, under the "user calls today" heading, the actual calories consumed (882) and the total calories burned (884) during the current day are displayed for comparison with the calculated calories IN and calories OUT for goal achievement for the current day. In an illustrative implementation, this display may be augmented with the color codes associated with the user's performance during the current day regarding calories consumed and burned, visually depicting the performance.

Figure 11:
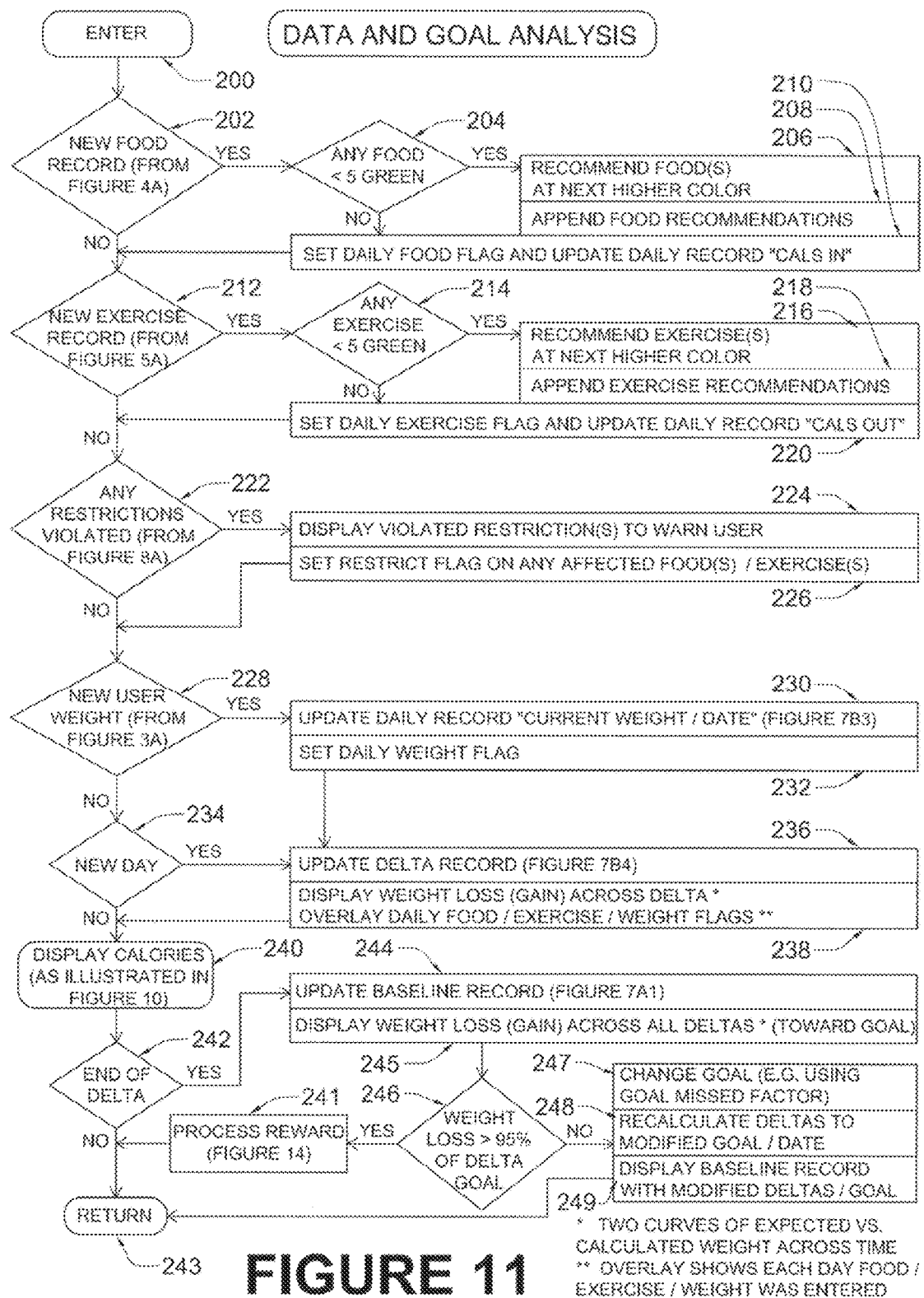
FIG. 11 is an illustrative flowchart for reviewing and/or adjusting a user goal that is triggered by any incremental progress indicated by the user toward that goal, including any food eaten or any exercise done, and further including any new weight reported or any food/exercise restriction violated.

FIG. 11 is a flowchart delineating the sequence of operations involved in data and goal analysis. The data and goal analysis subroutine is entered (200) upon being called by various routines described herein that implement the functionality identified in the figures referenced below. The data and goal analysis processing in FIG. 11 occurs upon the generation of any new food record (202), any new exercise record (212), any violation of user restrictions (222), or any new weight being entered by the user (228).

A check is initially made at block 202 to determine whether any new food record has been generated. If so, then a check is made at block 204 to determine whether the food consumed by the user had an associated color code other than Green (where the value 5 indicates the healthiest food color coded Green as explained above). If any food in a meal being consumed is other than the healthiest food (as indicated by Green), the previously described "stepping up the ladder" processing is initiated. Thus, as indicated at block 206, the system recommends food(s) at the next higher color code value to encourage the user to eat in a more healthy fashion. After recommending an alternative food to the user, the food recommendation is stored in a shadow database location associated with the food record (208). Thereafter, a daily food flag is set and the daily record shown in FIG. 7B3 is updated. The daily food flag indicates that a food record was constructed on the current day. Additionally, the cumulative "Cals IN" entry in the daily record shown in FIG. 7B3 is updated (210).

After the processing at block 210, or if the check for a new food record indicates that there is no new food record to process, a check is made at block 212 to determine whether there is a new exercise record to process. If so, a check is made at block 214 to determine whether any associated exercise was performed that has an associated color code other than Green (and therefore has an associated value less than 5). If any exercise is performed other than the healthiest rated exercise for the user (as indicated by the "Green" color code value 5), as indicated at block 216, the previously described "stepping up the ladder" exercise processing is performed. Thus, if a new exercise record indicates that the user ran 2 miles in 30 minutes that might be classified as a "Red" color code, the user will be, for example, encouraged to run at a somewhat faster pace to reach a pace that would be classified using an "Orange" color code instead of the original Red color code. Thus, as indicated at block 216, the system recommends one or more exercises at the next higher color code value to encourage the user to exercise in a healthier fashion.

After recommending an alternative exercise to the user, the exercise recommendation is stored in a shadow database location associated with the exercise record (218). Thereafter, a daily exercise flag is set and the daily record shown in FIG. 7B3 is updated. The daily exercise flag indicates that an exercise record was conducted on the current day. Additionally, the cumulative "Cals OUT" entry in the daily record shown in FIG. 7B3 is updated (220).

After the processing at block 220, or if the check for a new exercise record indicates that there is no new exercise record to process, a check is made at block 222 to determine whether any of the user's restrictions have been violated. The user's profile record format 720 is monitored to, for example, check the foods excluded in light of the data item RestrictF stored in the user health data list 724 shown in FIG. 8A. Additionally, the user's health data list 724 is monitored to determine whether specific exercises were limited or excluded as indicated by data item RestrictE. If it is determined that a new food record or new exercise record violates any known restriction, then a warning display is generated to warn the user that a restriction has been violated (224).

In illustrative implementations, it is contemplated that this warning system can be used to warn the user about a wide range of health related issues. For example, the system can warn an unwary user that a food contemplated for consumption includes a peanut-based oil to which the user is allergic. Similarly, a user may be warned that a food to be consumed includes a sufficient amount of sugar to raise a concern in light of the user's indicated issue with diabetes. Moreover, a user may be warned if a food or exercise record indicates consumption of a food or participation in exercise that does not comport with the user profile's designation of handicaps, ailments, injuries, habits, or medications. A warning may be generated, for example, if a food or beverage (such as alcohol) to be consumed is not appropriate in light of medications taken. In illustrative implementations, such restriction information may be based on input received from the user, or from other sources in implementations in which, for example, a physician, nutritionist, or other third party is actively participating to provide professional input. In certain illustrative implementations, based, for example, on input from a physician, food consumption thresholds, exercise thresholds and behavioral parameters may be either maintained or dynamically changed as needed. Exercise, for example, may increase from an expenditure of 300 calories per day 3 times per week early in the process to 500 calories per day, 5 times per week with light weights by the end of a certain active weight loss process interval. Calories may be advanced at this point from, for example, 1200 per day to 1500 per day. In another example, if a behavioral issue exists such that the user is not doing well adhering to the initially prescribed dietary regimen, an assessment of the issues contributing to the adherence problem can be made and the dietary regimen might be changed for example by increasing calories or adding more fruit to help the user improve adherence.

In such implementations where a physician, nutritionist or other third party is providing input (either directly or indirectly through the user), the routine accesses the user's profile to assess health-related information received directly or indirectly from a participating physician and/or nutritionist and/or healthcare provider including any generated thresholds for the user including but not limited to caloric intake, grams of saturated fat, grams of trans fat, milligrams of cholesterol, milligrams of sodium, grams of carbohydrate dietary fiber, grams of carbohydrate sugar, grams of protein, amounts by percent of daily requirement of Vitamin A, Vitamin C, Calcium and Iron, amount of exercise energy expenditure and other variables related to specific medical, nutritional and other needs of the user. For example, a physician may place both food and exercise restrictions on users suffering from cardiac issues. Checks are made to ensure that any health-related nutritional and exercise thresholds have not been exceeded. Examples include excess sugar consumption by users who have diabetic or borderline diabetic issues, excess sodium in those with hypertension, excess potassium and protein in those with renal disease and exercise limitations in the user with cardiovascular disease.

In an illustrative implementation, such restrictions received either directly or indirectly from a physician may result in a goal weight modification recommended by the system to either increase the amount of weight that should be lost, or slow down the rate at which weight should be lost to decrease stress on the user.

Turning back to FIG. 11, the system sets the restrict flag on any affected food(s) or exercise(s) that triggered a restriction warning (226). Such a restrict flag is thereafter associated by the system with any violating food or exercise.

After the processing at block 226 of the restriction-related content of FIG. 8A, or if the check for a restriction violation indicates that there is no known violation to process, a check is made at block 228 to determine whether a new user weight has been entered by the user. In certain illustrative implementations, the user is prompted to enter his or her weight at desired intervals such as on a daily or weekly basis.

If a user has entered a new weight, the newly entered weight is stored in a record associated with the user's profile shown in FIG. 8A and the daily record shown in FIG. 7B3 is updated to reflect a new "current weight/date" (224). Thereafter, in this illustrative implementation, the daily weight flag is set (232), after which, the delta record in FIG. 7B4 is updated (236).

After the delta record has been updated, the system displays either a weight loss or weight gain across the current delta time frame (238). In an illustrative implementation, such a display includes two curves of expected weight over the "delta" time period (the user's weight expectation based on goals that have been set) and calculated weight over the delta time period (the user's weight based on calories burned less calories consumed), and the user's actual reported weight over this time frame so that the user can see his or her progress over time and assess the accuracy of the user's reported calories consumed and calories burned. Additionally, in an illustrative embodiment, an overlay is created to display daily food, exercise, and weight flags so that the user can see, for example, the regularity with which food and exercise entries have been made. In an illustrative implementation, if there are major gaps in the exercise flag entries, the system generates a display encouraging the user to exercise more often.

If the check at block 228 indicates that a no new weight has been entered by the user, then a check is made at block 234 to determine whether the current day is a new day. If the current day is a new day, then the updating and display processing at blocks 236 and 238 is performed. The completion of processing after block 238 completes the updating of the baseline records shown in FIG. 7B.

After the processing at blocks 236 and 238, or if the check at block 234 indicates that the current day is not a new day, the display calories and goals illustrated in FIG. 10 is generated and displayed to the user.

After the calorie and goal related display has been generated a check is made at block 242 to determine whether the current day is the last day of a delta period that is used for goal assessment.

If the current day is the last day of the delta period, then the baseline record shown in FIG. 7A1 is updated to record the delta weight loss achievement (244). Additionally, a display is generated to show the weight loss or weight gain across all the deltas relating to the user's goal (245). In an illustrative implementation, such a display includes, for example, expected, calculated, and actual weight across time and an overlay showing each day that food, exercise, and weight has been entered by the user over the delta time period. A display that shows, for example, sparse exercise entries may serve to explain to the user why his/her current goal has not been met.

A check is then made at block 246 to determine whether a user's goal has been met. It should be recognized that the system may require, for example, 100% achievement of a goal weight loss before a reward is targeted for downloading to user. However, in this example, a reward trigger signal is generated if the user achieved 95% of the assigned goal for any delta period based on the check at block 246. Thus, the check at block 246 may be used to determine whether the user's overall weight loss goal has been met or whether an interim "subgoal" has been met to indicate whether or not the user is on track to reaching his or her overall goal.

The specific percentage assigned as the proper "reward" percentage may vary based on many factors including the user's past weight loss history, how close or how far the user is from his or her ideal weight, the user's overall general health, and other factors targeted to providing the individual user with the optimum amount of effective motivation and encouragement.

Figure 14:
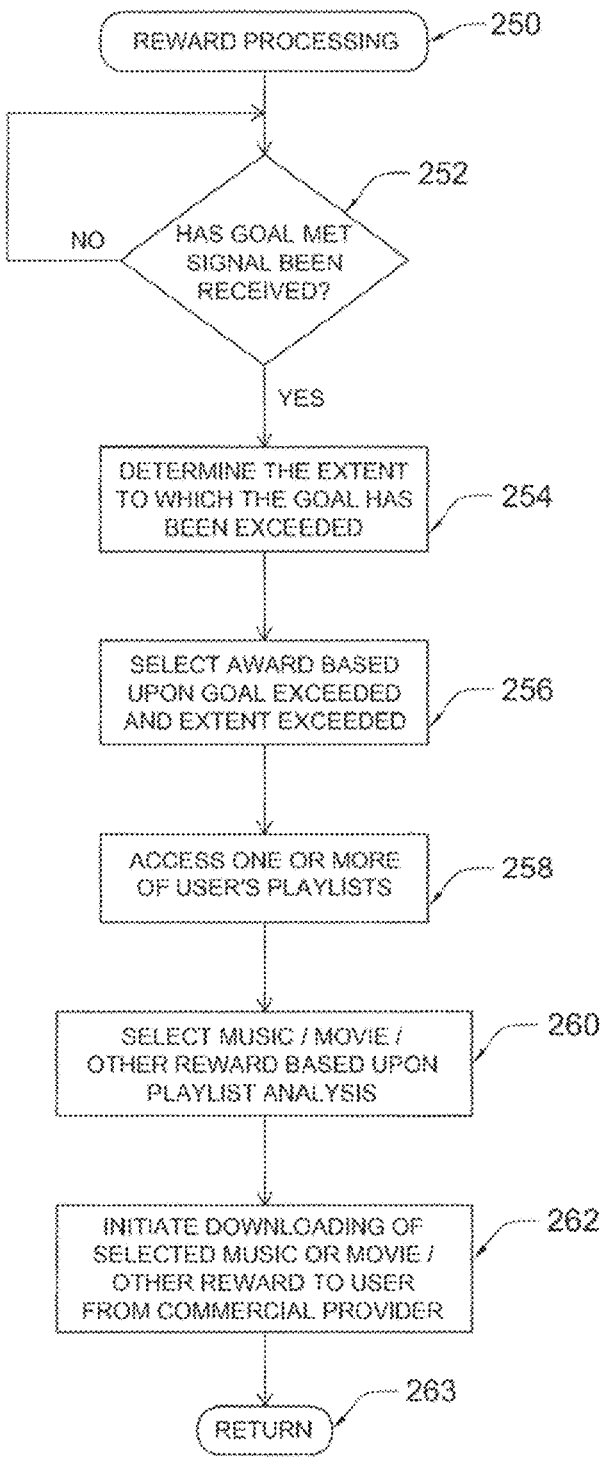
FIG. 14 is a flowchart delineating the sequence of operations performed in an illustrative implementation during reward processing.

If the check at block 246 indicates that the required percentage of the user's goal has been met, the routine generates a goal has been met signal and transmits such a signal together with goal achievement data to the reward processing routine (241) illustrated in FIG. 14 and then returns to the calling routine (243).

If the check at block 246 reveals that the user has achieved, for example, less than 95% of the assigned "delta" subgoal, processing is initiated to determine whether there is a need, for example, to change the final goal or current subgoal that is lower than the originally set goal depending on various factors, including the degree to which the goal has been missed and whether the initially assigned goal or subgoal is appropriate for the user given the user's food consumption and exercise performance history.

Daily caloric goals with their associated nutritional requirements may require modification at various points during the weight loss process. These adjustments may be made as a function of the weight loss progress (or lack of progress) as determined by the check at block 246. Alternatively, goals may need to be changed to address issues associated with recently developed medical conditions, such as diabetes or hypertension. Exercise goals may need to be changed as the process progresses. Typically, the amount of daily exercise will need to increase as weight comes down or specific alterations in type and duration of exercise will be needed based on the progress (or lack of progress) of the user. The specific goals of exercise may change throughout the process from predominantly aerobic, calorie burning exercise at the beginning of the weight loss endeavor to an exercise regimen that includes more muscle building activity and less aerobic activity as a user approaches his/her weight goal and transitions into a weight maintenance mode. New goals are displayed to the user on the user's mobile computing device display as indicated at block 249. Food or exercise related warnings are displayed to the user (e.g., as indicated at block 224).

In an illustrative implementation, the existing goal may be lowered by a desired increment, for example, 5% or 10% (247). In an illustrative implementation, such processing includes prompting the user to indicate if any new unreported injuries, ailments, or handicaps have arisen that contributed to the failure to meet a goal or subgoal. If so, the user is prompted to modify his or her user profile to result in a modified new goal. Such new user profile data may in turn create new food consumption and exercise related thresholds that may serve as new restrictions recorded in the user's profile.

Thereafter, the subgoal values for the delta periods shown in FIG. 7A1 are recalculated and modified to reflect the new goal weight loss and/or new goal anticipated achievement date (248). Thereafter, a new baseline record as illustrated in FIG. 7A1 is displayed with the modified, recalculated delta values and goals (249) and the routine branches back to the calling routine (243).

In illustrative implementations, after the goal analysis has been completed (during the processing at blocks 241, 246, 247-249), the routine generates feedback to the user regarding whether goals have been met, and provides recommended adjustments that may need to be made with respect to food consumption or exercise completion, and/or any warnings regarding exceeding physician's/healthcare provider's set thresholds for such health-related parameters as sugar intake, daily calorie intake, etc. Behavioral recommendations are also generated as needed taking into consideration caloric, nutritional, exercise and other parameters. In an illustrative implementation, for those who are grossly overweight or those who are attempting to stop smoking, congratulatory progress statements are forwarded with regularity as daily goals are met.

FIGS. 12A and 12B are described below and show two methods that may be used in determining a user's frame size to help converge on the ideal weight of a user for any given height that may be used in determining a user's weight loss goal. As an overview, FIG. 12A shows a rule-of-thumb wrist measurement that is relatively accurate, and is otherwise quite simple for most users to execute—often within 30 seconds. In contrast, FIG. 12B shows the original Met Life elbow method (circa 1942) that was quite accurate (but only when perfectly executed), but was otherwise quite difficult for most users —largely due to the uncertainty of what the correct elbow circumference was. Hence, the present app asks the user to perform the simpler wrist method.

As noted above, FIGS. 12A and 12B show two methods that may be used in determining a user's frame size to help converge on the ideal weight for any given height. Bone mass and muscle mass all play a part in determining optimal weight. This is why ideal weight charts have a range of ideal weights for height.

As shown in FIG. 12A, the first method of determining frame size by measuring wrist size is an easy method to utilize. The chart shows how small/medium/large frames can be differentiated based simply on wrist size. As an intersect between the sexes, at the height of 5'5", a man's medium frame equals a woman's large frame, which reinforces the need to keep Men's weight profiles separate from Women's. It is noted that for wrist sizes over 5' 5" height, Women's Large frame=Men's Medium frame.

FIG. 12B is a table correlating medium frames with the breadth of the elbow. Measuring the breadth of the elbow is harder but gives better accuracy. The chart in FIG. 12B shows the limits of the medium range based on elbow size, beyond which is large frame and below which is small frame. This original Met Life procedure was very accurate but hard to follow, so it tended to be glossed over, making the rule-of-thumb Wrist method even more appealing. As an intersect between the sexes, within medium frames, the elbow size of a man as short as 4' 10" is equal to the elbow size of a woman over 6 feet tall, which reinforces the need for an accurate DB that can discriminate down to frame sizes. It is noted here that, as an anomaly for Medium Frames, the elbow size of Women over 6' 0"=Men at 4' 10"-4' 11."

The elbow size measurement involves the following steps:
  Start in a standing position:
  Hold out your arm so that it's horizontal and parallel to the floor
  Make sure that your palm is facing upward
  Then bend your elbow so your forearm is at ninety degrees to the floor
  Use your index finger and thumb of opposite hand to find the narrow part of your elbow joint
  Use your finger and thumb like a gauge to find the breadth of your elbow
  Do this by measuring the gap in between them with a ruler or measuring tape.

Figure 12C:
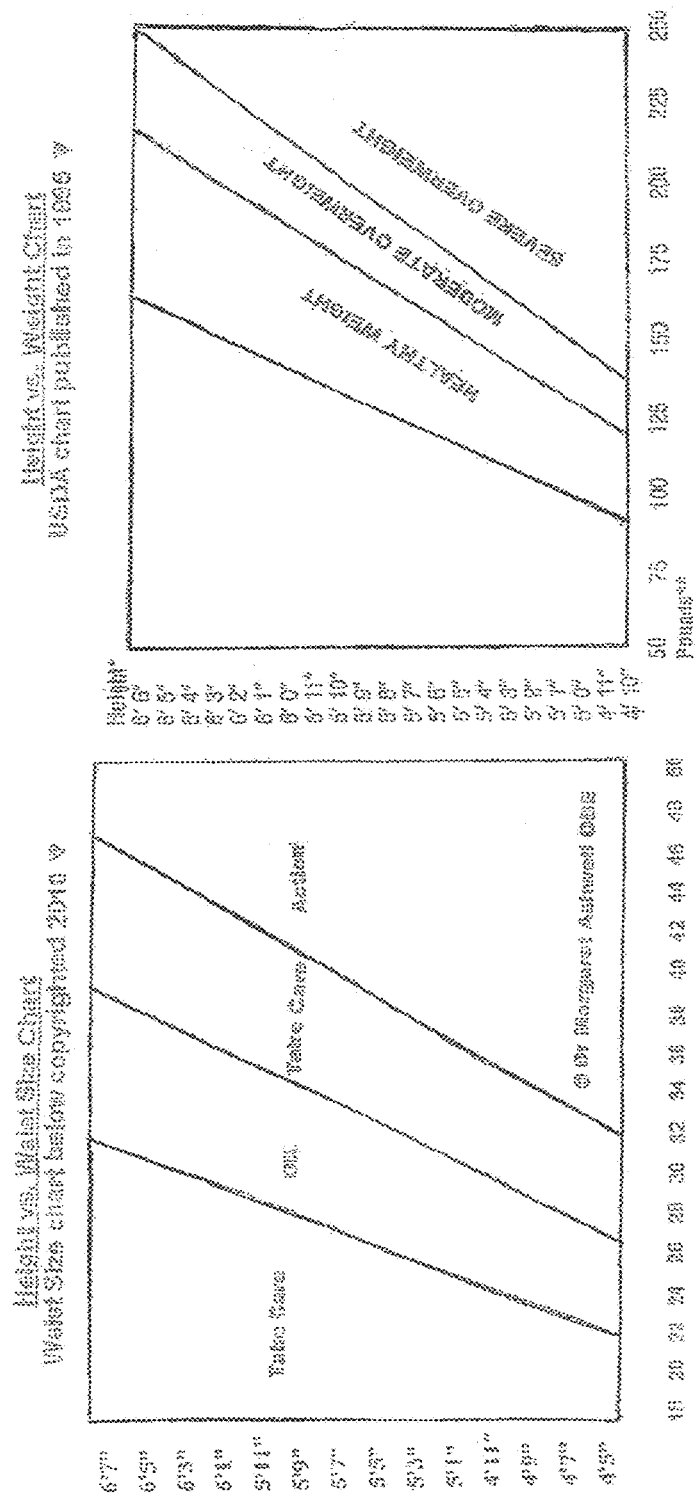
FIG. 12C shows a chart correlating waist size vs. height with underweight, healthy weight, moderate overweight and severe overweight (obese), as defined by the 4-zone USDA chart (1995) reflecting current BMI thresholds.

FIG. 12C provides a simple, efficient rule-of-thumb method for determining a user's obesity level from the size of his/her waist, much like the wrist circumference method above, and just as easy to measure in one minute. FIG. 12C shows a 2010 chart (LH side) that demonstrates how Waist Size plots virtually identical to Weight in the popular 1995 USDA chart (RH side). This variation is a further example of how pervasive the USDA chart has become across 15 years. Just as the USDA chart plots height vs weight, the Waist Size chart plots height vs waist size, yielding a chart that is remarkably similar in the 3 boundary lines, and the configuration of the 4 weight slices they demarcate:
  the RH severe overweight slice==>matches the LH "Action" slice
  the RH overweight slice==>matches the LH "Take Care" slice
  the RH healthy weight slice==>matches the LH dark "OK" slice
  the RH underweight slice==>matches the left-most "Take Care" slice
  the RH height runs 4' 10"-6'6"==>the LH height runs 4'5"-6'7"
  the RH weight runs 50-250 lbs==>the LH waist size runs 18-50"

In the USDA Chart generated in 1995, BMI has been utilized to determine the line between obesity and healthy weight. However, using BMI as the determining factor belies the significance of the underlying BMI equation (weight/height$^2$×703) and the fact it ignores the huge weight-per-height gap between Men and Women that was prominently declared for 50 years by its predecessor, the Met Life Table. In fact, the oversimplified BMI calculation itself (weight/height$^2$×703) is fatally flawed in that it does not require any measurement of actual body fat, but rather, wrongly assumes any excess weight above average for a given height is due to fat rather than muscle.

Given that the general definition of obese (for the Met Life table) is someone whose weight is 20% more than their ideal weight, this basic BMI flaw alone inflates the obesity rate of most countries by adding virtually every muscular athlete with <20% body fat to its obesity group—men and women who are by definition among the healthiest specimens on the planet—a factor that is partially accounted for by Met Life's wise expansion into body frames and frame overlaps.

Figure 13A:
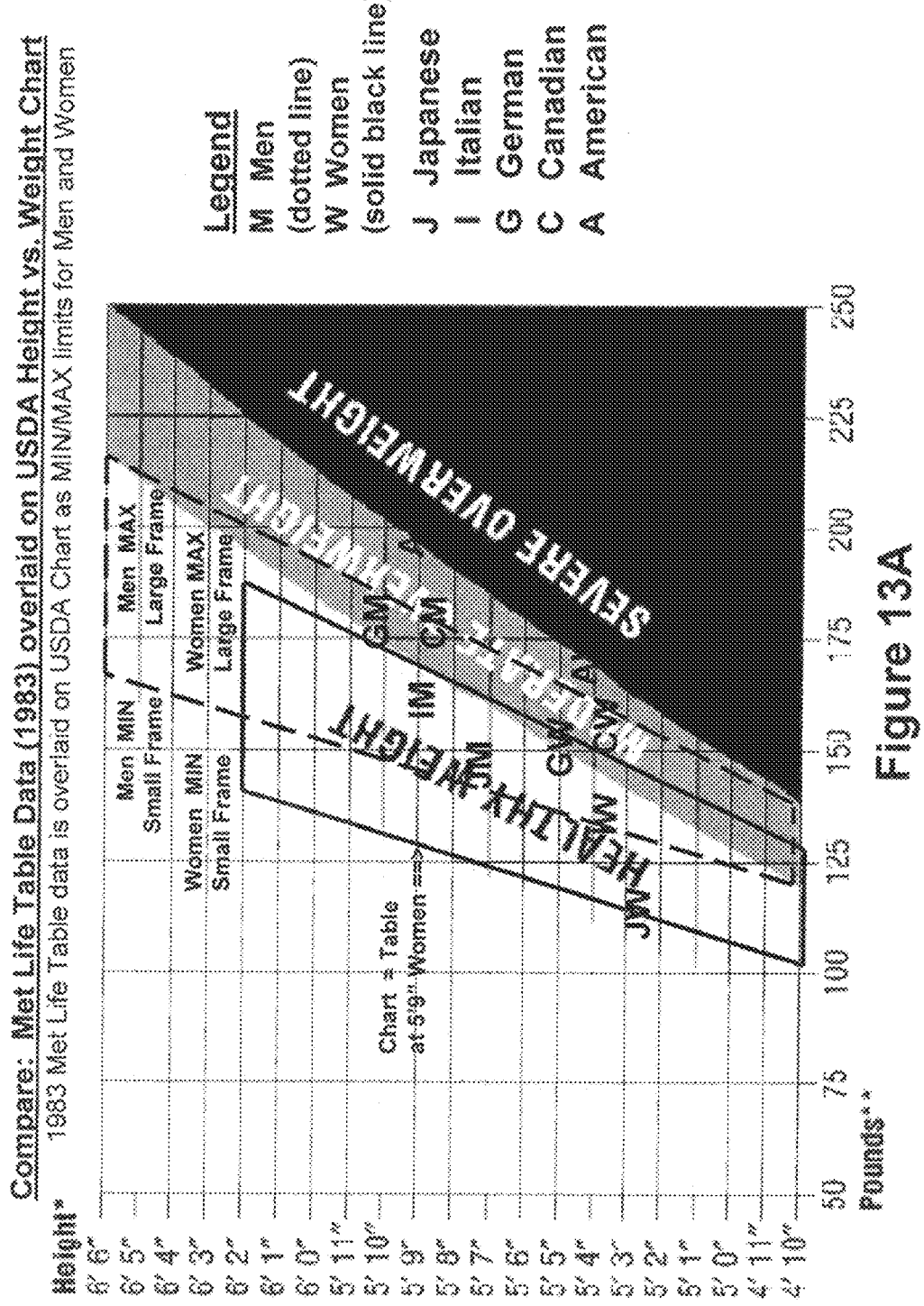
FIG. 13A shows an overlay of profiles for both men and women in the world-standard Met Life Table (updated 1983) on the 4-zone world-standard BMI Chart (by the USDA 1995) that reveals how far apart the two baseline standards are for tall women and all men, as confirmed by an additional overlay of men and women (average height/weight) from 5 modern industrialized countries.
Figures 13C1, 13C2:
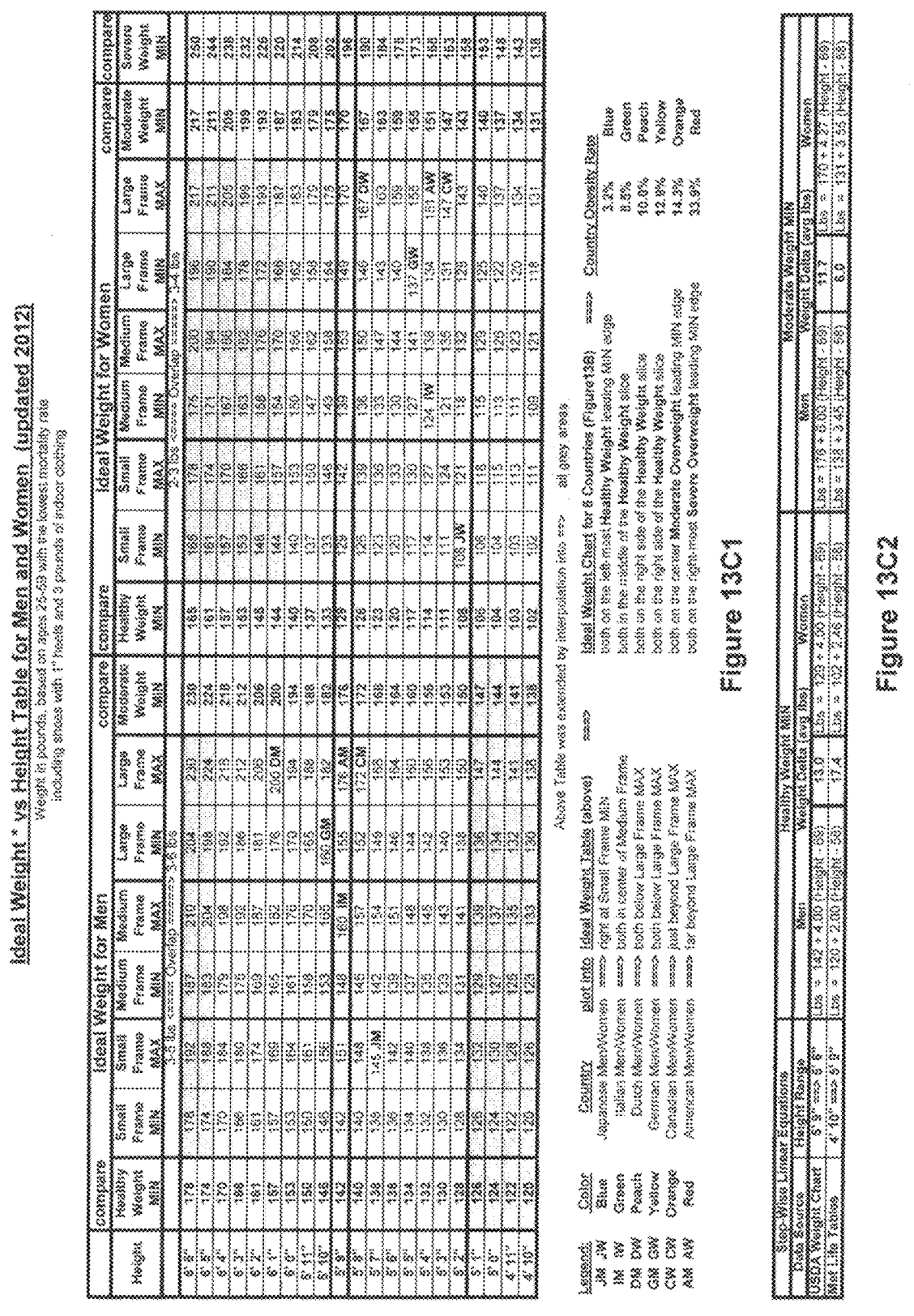

FIG. 13A shows an overlay of the prior art Met Life Table on the prior art USDA Chart that reveals how far apart these 2 baseline standards are for tall Women and all Men. As can be quickly visualized here in FIG. 13A, the Met Life profile for Women (solid black line) roughly matches up with the Chart's healthy weight slice (within +/−1.2%)—whereas, in stark contrast, Met Life's similarly-shaped profile for Men (dotted black line) is uniformly shifted right by 18 pounds at the base. The base spans the entire width of the center moderate weight slice, while the top of the Men's profile shifts left to span the entire healthy weight slice. This chart shows how closely the 1995 USDA chart tracked the original 1983 Met Life data for women and exactly how far up the weight scale men should have been plotted. An average error of +/−1.2% for women and a +8.3% average increase required for men.

This separation of the Men's profile (by 18 pounds upstream) from the Women's profile appears to confirm that the ultra-low healthy weight slice of the USDA Chart is entirely demarcated for Women, and as such is generally beyond the reach of Men. It is noted that the Chart and Table profiles for Women intersect at 5'9."

FIG. 13B shows how Met Life profiles can be rotated 6° around a common pivot point with the Chart (at 5' 9") to yield a more realistic ideal model for all Men and Women. The Met Life plot is better adapted to shorter people form 4 feet, 10 inches to five feet, four inches than the 1995 USDA weight chart. The USDA plot is better adapted to taller people 5 foot, 11 inches to 6 feet, 6 inches than the data in the Met Life plot. In these charts, women benefit most at the low end and men benefit most at the high end. In FIG. 13B, the Met Life data plotted in FIG. 13A is rotated clockwise at a five feet, nine inch pivot point to match up with the USDA chart. The database shown in FIG. 13C absorbs the best of both worlds, from Table to Chart:
  Bottom Half (4' 10"==>5'9") The time-honored independent Met Life profiles for both Women and Men were adopted exactly as shown in FIG. 13A. This new weight regime resolves the worst differences and complaints at both extremes:
  Leading Edge: Studies reveal that Japanese Women still falls within the profile, but now correctly at the leading edge—i.e., the Chart values are so severe at the low end that no one in the world (but Japanese women) can achieve them
  the same holds true for Japanese Men who are now correctly positioned right at the leading edge among all men (with the world-lowest 3.2% obesity)
  Trailing Edge: Studies reveal that Italian Men/Women correctly shifted to the center of their respective healthy weight slices (at a very low 8.5% obesity)
  similarly, the German Men/Women are correctly shifted just inside their respective healthy weight slices (at a reasonable 12.9% obesity)
  the Canadian Men/Women are correctly remained just inside the new, more narrow moderate weight slice (at weighted-average 14.3% obesity)
  the American Men/Women remained unmoved from their precarious perch just inside the severe weight slice (at world-worst 33.9% obesity)
  Top Half (5'9"==>6'6") This half was adopted from the more modern USDA Chart profile for Women, while the wholly independent Met Life profile for Men was adapted to the more relaxed slope of the Chart, exactly as shown in FIG. 13A. This weight regime will resolve the worst differences/complaints at both extremes:

Leading Edge: the worst-case extreme here is the Men's MIN up at 6' 6" (small frame) where, according to the Chart, a 6' 6" male is still healthy at 165 lbs But this weight is not achievable even by tall Dutchmen (at low 10% obesity) who are already up to 195 lbs @ 6' 1" (world's tallest avg height), whereas the Dutch women reach 165 lbs @ 5' 8" (avg), but they're 10 inches shorter than 6' 6"

Thus, the Men's MIN becomes more realistic shifted up by 13 lbs to 178 lbs

Trailing Edge: Only the German Men at 5'10" were affected here by the 6°CW rotation (around the pivot point at 5'9")—the GM is now correctly shifted just inside the trailing edge, which exactly matches the position of GW The upper-level weights are now achievable by tall men. This has been the most contentious area in the Met Life Tables—namely, they do not account for men taller than their 1942 model that are heavier but still healthy e.g., the 1983 Met Life table sets a healthy large-frame 6' 1" US male @ 192 lbs whereas, with the upgraded profile, he can now aim at more achievable 200 lbs.

In fact, the Dutch Men and Dutch Women (cited above) actually confirm the validity of both new profiles for Men/Women since, at their very low obesity rate (10%) they clearly qualify to appear in the Healthy Weight slice of the USDA Chart. This can be easily visualized by comparing where they map into the new profiles (overlaid on FIG. 13B) to where they'd plot in the old profiles (FIG. 13A):

database relating a user's height to a healthy "ideal" weight for a range of small, medium, and large frame minimum and maximum weight values for both men and women. The illustrative weight, nutrition, and exercise tracking system that is dedicated to helping today's users get healthier and/or lose weight presents a unique answer to the age-old question . . . exactly what is an "ideal" weight for a given user height? The database shown in FIG. 13C1 takes into account various generic factors that may affect the user's weight, such as gender, body frame (small/medium/large) and relative level of obesity. In an illustrative implementation, the database is advantageously designed to assist in calculating small increments of weight loss that can eventually lead an overweight user to a goal within his or her reach. The database shown in FIG. 13C1 is accessed in part by using wrist size to differentiate body frame and waist size to differentiate obesity level.

This new database has been derived by selectively reconciling and integrating the most historically reliable sources of height vs. weight data still in widespread use today:

Metropolitan Life Table (Met Life table), from their 1942 life expectancy data (updated 1983)

But, this aging data falls short of today's taller, heavier bodies that are still healthy USDA CNPP center Chart, from their 1995 obesity data (and Met Life Table).

The Met Life table has become a standard that is still widely used for determining recommended body weights. This table has been criticized for varied reasons:

Insured people tend to be healthier than uninsured people

The people included were predominantly white and middle-class

| Case in Point for Tall Men: Comparison of 2012 Profiles with earlier Profiles (based on BMI) | | | | | | |
|---|---|---|---|---|---|---|
| Extreme Example: Very Low Obesity | Extreme Example: Tallest in the World | | Earlier Men/Women Profiles FIG. 13A | | 2012 Profiles FIGS. 13B/13C | |
| The Netherlands | Height* | Weight | BMI** | Weight | Slice | Weight | Slice |
| Dutch Men (DM) | 6' 1" * | 195 lbs | 25.7** | >192 | Moderate | <200 | Healthy |
| Dutch Women (DW) | 5' 8" * | 165 lbs | 22.6 | =165 | Healthy (?) | <167 | Healthy |

\* Dutch Men and Women are the tallest in the world (passed the US 50 years ago)
\*\*At their very low obesity rate (10%), both DM/DW easily qualify as Healthy but Dutch Men get a Moderate ranking due to their skewed BMI @ 25.7 because BMI can't distinguish any natural weight increase due to muscle mass in tall men By embracing this extreme—the tallest healthy Men/Women in the world—this case in point confirms another significant way the newly-configured profiles for Men and Women have improved over the USDA Chart and Met Life Table. Moreover, this upgrade for taller men becomes all the more significant in light of the spiraling growth of sports, from recreational to competitive, worldwide—and the parallel explosion of fit athletes who play the sports, but are rated obese.

Unique Database (DB) to Calculate Ideal Weight Vs. Height

In accordance with an illustrative implementation, a user's weight goal may be selected based upon the ideal weight database shown in FIG. 13C1. In an illustrative implementation, the system may select a weight goal for the user based upon the FIG. 13C1 ideal weight database described below using user profile entries of height, weight, gender, and frame size (taking into account waist and wrist size (see FIGS. 12A/12B)) as illustrated in FIG. 8A).

In determining a user's goal weight, FIG. 13C1 depicts in a table format an illustrative new and improved system Frame size was not consistently measured Some people were actually weighed, some were not The table did not consider percentage of body fat or distribution The table is considered okay for people in their forties, but the weights are too heavy for younger people and too light for older people.

Yet despite all these caveats, the table has continued to serve as a worldwide standard together with updated versions of this table.

The database of FIG. 13C1 has been designed to take into account such criticisms of the Met Life table and to accommodate taller, healthy men and women, in that the Table has been extended up to 6'2" for women and up to 6'6" (and down to 4' 10") for men by interpolation. Further, the present DB has been designed to classify large/small-bone people in their correct frame size, which becomes important in taking into account the differences between men and women. Thus, the ideal weight database has been customized by the melding of Met Life tables, demographic data, frame size, body mass index, etc. While this approach has not been clinically proven or tested, it is presented as an illustrative implementation of a highly useful tool in determining a user's ideal weight that is tailored to individual users in a unique manner.

FIG. 13C1 ties together the above Tables/Charts into a single 2012 DB that integrates MIN/MAX frames (scaled up from 1983 Met Life Table) within MIN healthy/moderate edges (rotated/shifted from 1995 USDA Chart) that allows the system to provide an ideal weight (nearest lb) matched precisely to a user's exact height (nearest 1/4") for both Men (left side) and Women (right side). This Table reflects Ideal Weight per Body Frame according to Met Life data (updated 1983), with new MIN boundaries per FIG. 13B (updated 2012).

Unless separated by their naturally higher weights, men have been improperly lumped into impossible for many to reach lower weight profiles for women. The 2012 updates include reconfigured "healthy weight" slices, now separated for men and women, as redefined in the compare columns in FIG. 13C. The aging Met Life data is still valuable for its min/max ranges that were scaled up to define all 3 body frames within the expanded 2012 weight deltas.

In effect, the Chart of FIG. 13B plus Table 13C1 tie together data, indicators, and lessons learned from published data from various countries taking into account median age, obesity rate, height and weight in the spectrum of healthy to obese data for men and women, the Met Life table, the USDA weight chart and updates thereto.

In effect, Chart 13B/Table 13C1 tie together data:
For 5 Major Countries:
Median Age==>Obesity Rate==>Height and Weight
Ideal Weight vs. Height in the spectrum of Obese==>Healthy
  For individual Men/Women:
    As shown in the table, the 2012 Database Table 13C1 comprises modified primary data values Upon entry into reward processing (250), the routine checks to determine whether a "goal has been met" signal has been received from an identified user by, for example, reward server 16 (252). In an illustrative implementation, any goal being met may trigger an award generation including weight-related goals, exercise-related goals and smoking cessation-related goals. If no such signal has been received from any mobile computing device in the system, the reward processing routine awaits receipt of such a signal.

In the example shown in FIG. 14, it is contemplated that a reward is automatically generated without any selection by user. It should be understood, however, that in other implementations, the user may be involved in selecting a desired reward.

If an identified user's goal has been met, the routine determines the extent to which the goal has been exceeded (254). Such a determination may be made in an illustrative implementation based on data transmitted from server 14 regarding the user's goal achievement.

It should be understood that a reward may be embodied in a wide variety of forms. It is contemplated, without limitation, that, for example, rewards may be in the form of downloaded music, movies, digital versions of TV shows, music videos, cash, discounts at movies, restaurants (particularly those that include a wide range of healthy alternatives), discounts at sporting events, mobile games, mobile gaming currency, other mobile applications, etc.

In an illustrative implementation, a reward is selected based upon the extent to which a goal being exceeded (256). Thus if a user exceeds weight loss goals in a given month by, for example, 20 pounds or has stopped smoking for a predetermined extended, time period, the user may receive a movie as a reward as opposed to receiving downloaded music. In order to provide adequate motivation for users, it is desirable to provide rewards as soon as it is determined that a goal has been exceeded. For example, in an illustrative implementation, if a user exceeds a daily food consumption, smoking cessation, or exercise goal, the system may reward

| 2012 DB | 1995 USDA Chart | | 1983 Met Life Table | |
| --- | --- | --- | --- | --- |
| Upgrades | Men | Women | Men | Women |
| Separate Sexes into 2 Distinct Profiles | Heavier Profile (entirely new) | Lighter Profile (existing) | — (existing) | — (existing) |
| Expand Height Up/Down (per FIG. 13C) | — (existing) | — (existing) | Up to 6' 6" Down to 4' 10" | Up to 6' 6" — |
| Discriminate Height on Tall/Medium/Short (per FIG. 13B) | Rotate Medium and short −8° to Heavier Weight | Rotate Medium and short −8° to Heavier Weight | Rotate Tall 6° to Heavier Weight (NA below) | Rotate Tall 6° to Heavier Weight (NA below) |
| Distinguish Body Frame on Small/Medium/Large (per FIG. 12A) | Add 2 more ranges between Min/Max edges | Add 2 more ranges between Min/Max edges | (existing) scale values up per FIG. 13C | (existing) scale values up per FIG. 13C |
| Determine Body Frame Small/Medium/Large | via Wrist/elbow (per FIG. 12A) | via Wrist/elbow (FIG. 12A) | via Wrist/elbow (elbow existing) | via Wrist/elbow (elbow existing) |
| Determine Obesity Level Healthy/Moderate/Severe | via Waist Size (per FIG. 12C) | via Waist Size (FIG. 12C) | via Waist Size (per FIG. 12C) | via Waist Size (per FIG. 12C) |

FIG. 13C2 is a chart showing boundary equations that may be used to identify the ideal weight for men and women shown in FIG. 13C. More particularly, FIG. 13C2 shows step-wise linear equations for both men and women that identify the boundaries in the ideal weight chart of FIG. 13C for a healthy weight minimum and moderate weight minimum based on the two height ranges of 5 feet, 9 inches to 6 feet, 6 inches and 4 feet, 10 inches to 5 feet, 9 inches.

FIG. 14 is a flowchart delineating the sequence of operations in an illustrative implementation of reward processing.

such performance, by automatically downloading music of the type to which the user has shown an inclination to listen.

In accordance with an illustrative implementation, the system accesses one or more of the user's playlists (258). For example, users of the iPhone often utilize the iTunes application to download music of their choice. Accessing of the playlist associated with the user's use of iTunes will reveal a great deal of information regarding the user's listening and viewing preferences. For example, by accessing such a playlist or the like, it may be determined that the user has a particular preference for '90's music, classical music, music videos together with the particular selections within those and other categories. Moreover, it may be determined which selections are the user's top-rated, recently added, top 25 and most recently played selections. Further, the user's preferences with respect to movies, TV shows and other entertainment preferences may be determined.

Based upon an analysis of such data from iTunes, the routine may select a particular song which is likely to be appreciated by the user since, for example, it is performed by an artist who has been identified in the playlist as the performer of one of the user's top-rated songs (260). In this example, such a song may be downloaded upon the user meeting a daily goal. In other implementations, the routine may select up to three songs for the user to choose from; a similar approach may be used for TV shows, movies, or other reward options. If, for example, a user meets a weekly or monthly goal, a selected TV show or movie may be downloaded to the user as a reward. Alternatively, one of the other above identified wide range of rewards, such as a discount coupon to an entertainment or sporting event may be downloaded.

If for example, a song has been selected for downloading, the routine may interact with the iTunes store to trigger downloading such a song to the user to provide the user's reward for goal achievement (262). Thereafter, the routine returns to the mainline routine of FIG. 2A for further processing (263).

While the invention has been described in connection with what is presently considered to be the most practical and preferred embodiment, it is to be understood that the invention is not to be limited to the disclosed embodiments, but on the contrary, is intended to cover various modifications and equivalent arrangements included within the spirit and scope of the submitted claims.

The invention claimed is:

1. A method of operating a mobile weight and exercise tracking computing system, having a processing subsystem, a storage subsystem, and a touchscreen display, for enhancing user goal achievement comprising:
   storing, in said storage subsystem, health information about a user, including a first weight loss-related goal for a first time window spanning a relatively short period of time, and a second weight loss-related goal for a second time window spanning a relatively longer period of time than that of said first time window;
   acquiring, via said touchscreen display, data indicative of a first food of a first set of foods constituting a first meal consumed by said user during said first time window in response to said user identifying said first food;
   generating, by said processing subsystem, data indicative of the calories consumed by said user as a result of eating said first food and said first meal;
   acquiring data, via said touchscreen display, indicative of an exercise performed during said first time window, in response to said user identifying a first exercise;
   determining, by said processing subsystem, the calories burned by said user as a result of performing said first exercise;
   determining, by said processing subsystem, the amount of calories that may be consumed by said user during a second meal expected to occur within said first time window in order to meet said first weight loss-related goal, based upon the current calorie total during said first time window, including calories consumed by said user as a result of eating said first meal and the calories burned by said user as a result of performing exercise during said first time window including said first exercise; and
   displaying, via said touchscreen display, the amount of calories that may be consumed by said user during said second meal in order to meet said first weight loss-related goal.

2. A method of operating a mobile weight and exercise tracking computing system according to claim 1, further including assigning an ideal weight for said user taking into account the user's height, gender and frame size; and
   storing said ideal weight for said user in said storage subsystem.

3. A method of operating a mobile weight and exercise tracking computing system according to claim 1, further including storing a desired weight database in said storage subsystem relating user height to a desired weight for a range of body frame sizes for both men and women.

4. A method of operating a mobile weight and exercise tracking computing system according to claim 1, wherein said first weight loss-related goal relates to a daily goal and said displaying step includes displaying to the user the amount of calories that may be consumed at dinner in order to meet said first weight loss-related goal, based upon the calories consumed at breakfast and lunch minus the calories burned during exercise performed in said first time window.

5. A method of operating a mobile weight and exercise tracking computing system according to claim 1, further including the steps of determining if at least one of said first weight loss-related goal and said second weight loss-related goal has been met, accessing an ideal weight database to determine an ideal weight of said user, wherein said step of determining at least one of said first weight loss-related goal and said second weight loss-related goal has been met includes the step of assessing the progress made by the user in reaching said ideal weight over successive time windows.

6. A method of operating a mobile weight and exercise tracking computing system according to claim 1, further including associating a digital value indicative of a first color code associated with a first health-related rating of said first food and a second digital value indicative of a second color code associated with a second health-related rating of said first food, wherein said first health-related rating and said second health-related rating relate, respectively, to the amount of first and second nutrients contained in said first food.

7. A method of operating a mobile weight and exercise tracking computing system according to claim 1, wherein said mobile weight and exercise tracking computing system includes a GPS receiver, and said data indicative of an exercise performed by said user is generated in part based upon device location data generated by said GPS receiver.

8. A method of operating a mobile weight and exercise tracking computing system according to claim 1, wherein said processing subsystem includes a behavioral subsystem, further including generating at least one question about the user's diet, receiving input in response to said at least one question from said user relating to the user's diet, and generating recommendations in response to the user's input via said touchscreen.

9. A method of operating a mobile weight and exercise tracking computing system according to claim 1, further including determining if a food or exercise-related goal has been met by said user based at least in part on calories consumed and/or calories burned by said user, wherein said processing subsystem includes a reward generating subsystem, and wherein said method further includes automatically selecting digital entertainment content to be downloaded to said mobile computing system based data relating to expected calories consumed and/or calories burned by said user.

10. A method of operating a mobile weight and exercise tracking computing system for enhancing user goal achievement comprising:
   storing, in a first set of storage locations, health information about a user including a user's food and exercise data during a first time window and a first intermediate weight loss-related goal for said first time window covering a first period of time;
   storing, in a second set of storage locations, a user's food and exercise data during a second time window and a second intermediate weight loss-related goal covering a second period of time subsequent to said first period of time;
   storing, in a third set of storage locations, a third weight loss-related loss goal;
   acquiring data indicative of food expected to be consumed by said user during said first time window;
   generating data indicative of the calories consumed by said user as a result of eating said food, and storing said data indicative of calories consumed in said first set of storage locations;
   acquiring data indicative of exercises performed by said user during said first time window;
   determining the calories burned by said user as a result of performing said exercises during said first time window and storing said calories burned in said first set of storage locations;
   prompting the user to enter a current weight at the end of the first time window; and
   determining if at least one of said first intermediate weight loss-related goal, said second intermediate weight loss-related goal, or said third weight loss-related goal has been met.

11. A method according to claim 10, further including the step of assessing the user's performance with respect to achievement of said first intermediate weight loss-related goal, and changing said first intermediate weight loss-related goal depending in part on said assessing step.

12. A method of operating a mobile weight and exercise tracking computing system according to claim 10, further including providing feedback to the user relating to progress towards achieving each of said first weight loss-related goal and said second weight loss-related goal.

13. A method according to claim 10, further including maintaining a daily record relating to foods consumed during said first time window.

14. A method of operating a mobile weight and exercise tracking computing system according to claim 10, further including associating a digital value indicative of a first color code associated with a first health-related rating of said first food, and a second digital value indicative of a second color code associated with a second health-related rating of said first food, wherein said first health-related rating and said second health related rating relate, respectively, to the amount of first and second nutrients contained in said first food.

15. A method of operating a mobile weight and exercise tracking computing system according to claim 10, wherein said mobile weight and exercise tracking computing system includes a GPS receiver, and data indicative of at least one exercise performed by said user is generated in part based upon device location data generated by said GPS receiver.

16. A method of operating a mobile weight and exercise tracking computing system for enhancing user goal achievement comprising:
   storing, in at least one storage system, health information about a user including multiple weight loss-related goals;
   acquiring data indicative of a first food in response to said user identifying a first food expected to be consumed by said user;
   associating a digital value indicative of a health-related color code rating of said first food using multiple colors to distinguish between multiple categories of foods, including a very healthy food category covering foods having a very high nutrient-related rating and a good food category covering foods with a good nutrient-related rating but which are rated lower than the very healthy foods with a very high nutrient-related rating;
   determining whether said first food expected to be consumed by the user has an associated color code from a category other than said very healthy food category;
   recommending to said user at least one food associated with a color code in a healthier color code category than said first food, if said determining step indicates that said first food has an associated color code that is not as high as said very healthy food category;
   acquiring data indicative of a first exercise in response to said user identifying a first exercise expected to be performed by said user;
   determining the calories expected to be burned by said user during said first exercise;
   determining if at least one of said multiple weight loss-related goals has been met; and
   displaying to said user information about calories expected to be consumed, or calories expected to be burned, and at least one color code.

17. A method according to claim 16, further including the step of associating a digital value indicative of a health-related color code rating of said first exercise using multiple colors to distinguish between multiple health-related categories of exercises, including a very healthy exercise category covering exercises with a very high health-related rating and a good exercise category covering exercises that have a good health-related rating but which are rated lower than exercises with a very high health-related rating, and further including:
   determining whether said first exercise expected to be performed by the user has an associated color code other than the color code for a very healthy exercise, and
   recommending to said user at least one exercise associated with a color code that is in a healthier color code category than the color code associated with said first exercise, if said first exercise was determined to be in a category other than said very healthy exercise category.

18. A method according to claim 16, further including:
   inputting by said user a first set of foods constituting a meal;
   associating each food that has been input as part of a meal with a digital color code using multiple colors to distinguish between categories of very healthy foods and moderately healthy foods;
   determining whether any of the foods expected to be consumed by the user had an associated color code from a category other than a very healthy food category, recommending to said user at least one food associated with a color code that is in a healthier color code category if it is determined that a food expected to be consumed as part of said meal had an associated color code indicative of other than a very healthy food.

19. A method according to claim 16, further including associating a first color code with said first food, if said food identified is determined to be one of a small number of top foods having a superior nutrient-related rating and associating a different color code if said food identified has a nutrient-related rating higher than other foods with a good nutrient-related rating but lower than the superior nutrient-related rating of said top foods.

* * * * *